(12) United States Patent (10) Patent No.: US 7,853,241 B1
Harrison (45) Date of Patent: Dec. 14, 2010

(54) REMOTE ACCESS MANAGEMENT SYSTEMS

(76) Inventor: Tammy L. Harrison, 2616 Alvord La., Redondo Beach, CA (US) 90278

( * ) Notice: Subject to any disclaimer, the term of this patent is extended or adjusted under 35 U.S.C. 154(b) by 589 days.

(21) Appl. No.: 11/874,785

(22) Filed: Oct. 18, 2007

Related U.S. Application Data

(60) Provisional application No. 60/862,042, filed on Oct. 18, 2006, provisional application No. 60/882,131, filed on Dec. 27, 2006.

(51) Int. Cl.
*H04W 88/02* (2009.01)
(52) U.S. Cl. ..................................... 455/406
(58) Field of Classification Search .............. 455/424, 455/406, 557
See application file for complete search history.

(56) References Cited

U.S. PATENT DOCUMENTS

| | | | |
|---|---|---|---|
| 6,022,315 A | 2/2000 | Ilif | |
| 6,149,440 A | 11/2000 | Clark et al. | |
| 6,272,470 B1 | 8/2001 | Teshima | |
| 6,397,224 B1 | 5/2002 | Zubeldia et al. | |
| 6,415,295 B1 | 7/2002 | Feinberg | |
| 6,934,698 B2 | 8/2005 | Judd et al. | |
| 6,961,586 B2 | 11/2005 | Barbosa et al. | |
| 7,099,896 B2 | 8/2006 | Fields et al. | |
| 7,110,955 B1 | 9/2006 | Barhnart et al. | |
| 7,379,605 B1 | 5/2008 | Tiesa | |
| 2002/0010679 A1 | 1/2002 | Felsher | |
| 2003/0154110 A1 | 8/2003 | Walter et al. | |
| 2004/0148194 A1 | 7/2004 | Wellons et al. | |
| 2004/0204961 A1 | 10/2004 | Rensimer et al. | |
| 2004/0220830 A1 | 11/2004 | Moreton et al. | |
| 2005/0055244 A1 | 3/2005 | Mullen et al. | |
| 2005/0125258 A1 | 6/2005 | Yellin et al. | |
| 2006/0036471 A1 | 2/2006 | Sanjay-Gopal et al. | |
| 2006/0080151 A1 | 4/2006 | Barbash | |
| 2007/0027715 A1 | 2/2007 | Gropper et al. | |
| 2009/0252480 A1 | 10/2009 | Wright et al. | |

*Primary Examiner*—Diane Mizrahi
(74) *Attorney, Agent, or Firm*—Stoneman Law Patent Group; Martin L. Stoneman; Thomas V. DelRosario

(57) ABSTRACT

The Remote Access Management System is a patient scheduling and superbill generator with cross migration between PDAs, cell phones and any wireless device linking to medical practice management software. It is a web based application any provider can use to schedule patient appointments and generate a superbill for a patient's visit. The Remote Access Management System links to medical practice support software (medical practice management systems, electronic medical records systems). There is no double data entry. A provider can view and create new appointments from any wireless device with access to the internet. Any appointments created in the medical practice management software can be viewed online in real time. The provider can add new appointments, patients, and superbills directly. This information will automatically be transferred into the medical practice support software.

2 Claims, 74 Drawing Sheets

| Clear | | | | | | | [ 1 - 4 of 4 ] |
|---|---|---|---|---|---|---|---|
| Select All None | LastName FirstName | Chart No | Date of Birth | Address | Gender | SSN | View |
| ☐ | mon, gee | MON0000 | 01/12/1977 | | Male | | ✓ |
| ☐ | kalis, Jag | KALIS0000 | 02/26/1979 | Cambridge town Cambridge town Cambridge town Cambridge town | Male | 123-12-1234 | ✓ |
| ☐ | Daniel, Kenny | DANIEL0000 | 12/12/2002 | 4th Block, Richard Street | Male | | ✓ |
| ☐ | Waugh, Steve | WAUGH0000 | 07/18/1967 | | Male | | ✓ |

| Select All None | Patient | Chart No | Date | Start Time | Provider | Status | View | Edit | Delete |
|---|---|---|---|---|---|---|---|---|---|
| | Don S Nelson | NEL001 | 03/29/2007 | 08.15 AM | Dr. Michelle Lynn | Pending | 🔍 | ✏️ | X |
| | D Muthu Raja | MUTHU 0000 | 03/29/2007 | 11.30 AM | Dr. Michelle Lynn | Completed | 🔍 | ✏️ | X |
| | Kiran Raghu | RAGHU0000 | 03/29/2007 | 10.30 AM | Dr. Michelle Lynn | Recall | 🔍 | ✏️ | X |
| | DONNA L MAM | MMMMM0000 | 03/29/2007 | 03.15 AM | Dr. Michelle Lynn | Confirmed | 🔍 | ✏️ | X |

[1 - 4 of 4]

Clear

FIG. 52

Total Amount: $ 2030.00

| Select All None | Billing No | Chart No | Date From | POS | CPT | Units | Billing Amount | View | Rules | Edit |
|---|---|---|---|---|---|---|---|---|---|---|
| | 32 | GREGG0000 | 10/01/2004 | 11 | 90718 | 10 | $ 180.00 | 🔍 | | ✏️ |
| | 32 | GREGG0000 | 10/01/2004 | 11 | 5456 | 100 | $ 2000.00 | 🔍 | | ✏️ |
| | 56 | ALDERM0000 | 07/05/2007 | 11 | CASH | 5 | $ -150.00 | 🔍 | ! | ✏️ |

[1 - 3 of 3]

Clear

FIG. 53

| Select All None | Code | Description | Common Code | Edit | Delete |
|---|---|---|---|---|---|
| | | | | | [1 - 4 of 4] |
| ☐ | 232.90 | Fever and Headache | ☑ | ✎ | ✗ |
| ☐ | 567.56 | Stomach Problem with Ulsar | ☐ | ✎ | ✗ |
| ☐ | 878 | Less Eye Sight | | ✎ | ✗ |
| ☐ | 99023 | Blood Test and General Testing. | ☑ | | |

Clear

| Select All None | Code | Description | Common Code | Edit | Delete |
|---|---|---|---|---|---|
| ☐ | 100.01 | Tubar Culosis Diagnosis | ☐ | ✏ | X |
| ☐ | 121.22 | Stomach Problem | ☑ | ✏ | X |
| ☐ | 454.44 | Fever and Head Ache | ☑ | ✏ | X |
| ☐ | 77.21 | Vomit with Blood | ☐ | ✏ | X |

[1 - 4 of 4]

Clear

FIG. 56

Rules Wizard

Rules Wizard

Rules: [    ]

Search    Reset

Add Rule

FIG. 57

Search Rule

[1 - 2 of 2]

| CPT Code | POS | Units | Modifier-OR | Modifier-AND | Diagnosis-OR | Diagnosis-AND | Delete |
|---|---|---|---|---|---|---|---|
| 99213 | 11 | | | | | | X |

FIG. 58

Place of Service

Search Place of Service

Code: _____  Name: _____

[Search] [Reset]

[Add POS]

FIG. 59

Place of Service

Search Place of Service

Code: _____    Name: _____

[Search]  [Reset]

[Add POS]

Search Result

| Code | Name | Edit | Delete |
|------|------|------|--------|
| 11 | POS1 | ✎ | X |
| 12 | POS2 | ✎ | X |
| 13 | POS3 | ✎ | X |

Place of Service

Search Place of Service

Code: _____    Name: _____

[Search]  [Reset]

[Add POS]

FIG. 61

Place of Service

Search Place of Service

Code: [ 14 ]    Name: [          ]

[Search]  [Reset]

[Add POS]

Search Result

[ 1 - 1 of 1 ]

| Code | Name | Edit | Delete |
|------|------|------|--------|
| 14   | POS4 | ✎    | X      |

Place of Service

Search Place of Service

Code: [     ]   Name: [     ]

[ Search ]  [ Reset ]

[ Add POS ]

Search Result

| Code | Name | | Edit | Delete |
|------|------|---|------|--------|
| 11 | POS1 | | ✎ | X |
| 12 | POS2 | | ✎ | X |
| 13 | POS3 | | ✎ | X |

| ACCOUNT | POS | UNIT | MODIFIER | CATEGORY | CUSTOMIZE |

Patient Category

Search Category

Category Name: [____]      Description

[Search]  [Reset]

[Add Category]

FIG. 68

| ACCOUNT | POS | UNIT | MODIFIER | CATEGORY | CUSTOMIZE |

Patient Category

Search Category

Category Name: [____]    Description [____]

[ Search ]  [ Reset ]

[ Add Category ]

Search Result    [1-2 of 2]

| Category Name | Description | Edit | Delete |
|---|---|---|---|
| AET000 | Active Patient | ✎ | X |
| EMG001 | Emergency Patient | ✎ | X |

| ACCOUNT | POS | UNIT | MODIFIER | CATEGORY | CUSTOMIZE |

Patient Category

Search Category

Category Name: [         ]   Description [         ]

[ Search ]  [ Reset ]

[ Add Category ]

Patient Category

Search Category

| Category Name: | Description | |
|---|---|---|
| Search | Reset | |
| Add Category | | |

Search Result [1-of 1]

| Category Name | Description | Edit | Delete |
|---|---|---|---|
| ALLERGIC | description | ✎ | X |

Edit Patient Category

Category Name: ALLERGIC

Description: description

Category For: Provider Only

Save   Close

FIG. 73

| ACCOUNT | POS | UNIT | MODIFIER | CATEGORY | CUSTOMIZE |

Patient Category

Search Category

Category Name: [____]     Description [____]

[ Search ]   [ Reset ]

[ Add Category ]

Search Result

| Category Name | Description | Edit | Delete |
|---|---|---|---|
| | | | [1-2 of 2] |
| AET000 | Active Patient | ✎ | X |
| EMG001 | Emergency Patient | ✎ | X |
| | | | [1-2 of 2] |

FIG. 74

Customize View Superbill in Mobile

| ACCOUNT | POS | UNIT | MODIFIER | CATEGORY | CUSTOMIZE |

Location
Created Date
Copay
Facility
Insurance Company Name
Date To
Diagnosis Code 1
Diagnosis Code 2

Billing No
CPT Code
Date From

Transaction Lines in View Superbill: 5

Other Options
- ☑ Turn on CPT pull downs
- ☑ Turn on Diagnosis pull downs
- ☑ Turn on POS pull downs
- ☑ Turn on Units pull downs
- ☑ Turn on Modifier pull downs
- ☑ Automatically add Diagnosis Codes from Patient to Superbill Save    Cancel

FIG. 75

REMOTE ACCESS MANAGEMENT SYSTEMS

CROSS-REFERENCE TO RELATED APPLICATIONS

The present application is related to and claims priority from prior provisional application Ser. No. 60/862,042, filed Oct. 18, 2006, entitled "PRACTICE MANAGEMENT REMOTE ACCESS SYSTEMS", and is related to and claims priority from prior provisional application Ser. No. 60/882,131, filed Dec. 27, 2006, entitled "REMOTE ACCESS MANAGEMENT SYSTEMS", the contents both of which are incorporated herein by this reference and are not admitted to be prior art with respect to the present invention by the mention in this cross-reference section.

BACKGROUND

This invention relates to providing a system for improved remote access to physician's practice support systems. More particularly this invention relates to providing a system for enabling physicians and other authorized persons to remotely complete certain activities, such as patient scheduling, related to practice management and related software systems.

Increasingly, physicians must maintain contact with their offices on a real-time basis, but, even with the advent of the Internet and cellular technologies, it is still difficult to manage patient information at times when the office is closed or when it is not possible to call the office.

Thus, it is highly desirable to provide a system for providing improved access to physician's practice management systems to remotely complete certain activities, such as patient scheduling and billing and similar activities related to practice management.

OBJECTS AND FEATURES OF THE INVENTION

A primary object and feature of the present invention is to provide a system that permits use of a cellular-based device for remote access to a medical provider's practice support system which is otherwise not enabled for web-browser-based remote access.

It is a further object and feature of the present invention to provide such a system that enables use of a cellular-based device for remote access to a medical provider's practice management system, electronic medical records system, and other related medical support systems otherwise not enabled for web-browser-based remote access.

It is a further object and feature of the present invention to provide such a system that permits use of a mobile device (frequently cellular-based) for remote access to a medical provider's practice management system to create, edit and view patients' appointment schedules.

It is a further object and feature of the present invention to provide such a system that permits use of a mobile device (frequently cellular-based) for remote access to a medical provider's practice support system to create, edit and view patients' information (name and address, etc.).

It is a further object and feature of the present invention to provide such a system that permits use of a mobile device (frequently cellular-based) for remote access to a medical provider's practice management system to create, edit and view patients' superbills.

It is a further object and feature of the present invention to provide such a system that permits use of a mobile device (frequently cellular-based) for remote access to a medical provider's practice management system to create, edit and view diagnosis codes.

It is a further object and feature of the present invention to provide such a system that permits use of a mobile device (frequently cellular-based) for remote access to a medical provider's practice management system to create, edit and view CPT codes [Current Procedural Terminology is a list maintained by the American Medical Association to provide unique billing codes for services rendered by physicians and other medical practitioners.]

It is a further object and feature of the present invention to provide such a system that permits use of a mobile device (frequently cellular-based) for remote access to a medical provider's practice management system to create, edit and view CPT codes.

It is a further object and feature of the present invention to provide such a system that permits real-time mobile use of a medical provider's practice management system.

It is a further object and feature of the present invention to provide such a system wherein the display of information on a cellular-based device may be customized to the preferences of a practitioner or system administrator.

A further primary object and feature of the present invention is to provide such a system that is efficient, inexpensive, and handy. Other objects and features of this invention will become apparent with reference to the following descriptions.

SUMMARY OF THE INVENTION

In accordance with a preferred embodiment hereof, this invention provides a method comprising the steps of: offering, by at least one software provider, relating to at least one medical practice support system, at least one web-browser-based communications software system to at least one user of at least one wireless-access-protocol-enabled cellular-based device; wherein such at least one medical practice support system is not otherwise web-browser-accessible using the Internet by using such at least one wireless-access-protocol-enabled cellular-based device; communicatively coupling such at least one web-browser-based communications software system to such at least one medical practice support system; permitting access to such at least one web-browser-based communications software system by such at least one user; enabling receiving, by such at least one web-browser-based communications software system, at least one function request relating to such at least one medical practice support system from such at least one wireless-access-protocol-enabled cellular-based device; enabling transmitting, by such at least one web-browser-based communications software system, such at least one function request to such at least one medical practice support system; enabling receiving, by such at least one web-browser-based communications software system, results of such at least one function request from such at least one medical practice support system; and enabling transmitting such results of such at least one function request to such at least one wireless-access-protocol-enabled cellular-based device. Moreover, it provides such a method, further comprising the steps of: enabling detecting, by such at least one web-browser-based communications software system, at least one wireless-access-protocol-enabled cellular-based device type used by such at least one user to send such at least one function request; enabling determining, by such at least one web-browser-based communications software system, at least one user interface format compatible with such detected at least one wireless-access-protocol-enabled cellular-based device type; enabling input, by such at least one user, of such at least one function request using such determined at least one user interface format compatible with such at least one wireless-access-protocol-enabled cellular-based device; and enabling display, by such at least one web-browser-based communications software system, of such results of such at least one function request using such determined at least one user interface format. Additionally, it provides such a method, wherein such step of enabling receiving, by such at least one web-browser-based communications software system, at least one function request relating to such at least one medical practice support system from such at least one wireless-access-protocol-enabled cellular-based device, comprises the steps of: enabling receiving, by such at least one web-browser-based communications software system, at least one search request relating to patient demographic data from such at least one wireless-access-protocol-enabled cellular-based device; and enabling receiving, by such at least one web-browser-based communications software system, at least one view request relating to such patient demographic data from such at least one wireless-access-protocol-enabled cellular-based device. Also, it provides such a method, wherein such step of enabling receiving, by such at least one web-browser-based communications software system, at least one function request relating to such at least one medical practice support system from such at least one wireless-access-protocol-enabled cellular-based device, comprises the steps of: enabling receiving, by such at least one web-browser-based communications software system, at least one modification request relating to such patient demographic data from such at least one wireless-access-protocol-enabled cellular-based device; enabling receiving, by such at least one web-browser-based communications software system, at least one add request relating to such patient demographic data from such at least one wireless-access-protocol-enabled cellular-based device; and enabling receiving, by such at least one web-browser-based communications software system, at least one delete request relating to such patient demographic data from such at least one wireless-access-protocol-enabled cellular-based device. In addition, it provides such a method, wherein such at least one medical practice support system comprises at least one medical practice management system. And, it provides such a method, wherein such step of enabling receiving, by such at least one web-browser-based communications software system, at least one function request relating to such at least one medical practice management system from such at least one wireless-access-protocol-enabled cellular-based device comprises the steps of: enabling receiving, by such at least one web-browser-based communications software system, at least one search request relating to patient appointment data from such at least one wireless-access-protocol-enabled cellular-based device; and enabling receiving, by such at least one web-browser-based communications software system, at least one view request relating to such patient appointment data from such at least one wireless-access-protocol-enabled cellular-based device. Further, it provides such a method, wherein such step of enabling receiving, by such at least one web-browser-based communications software system, at least one function request relating to such at least one medical practice management system from using such at least one wireless-access-protocol-enabled cellular-based device comprises the steps of: enabling receiving, by such at least one web-browser-based communications software system, at least one modification request relating to such patient appointment data from such at least one wireless-access-protocol-enabled cellular-based device; enabling receiving, by such at least one web-browser-based communications software system, at least one add request relating to such patient appointment data from such at least one wireless-access-protocol-enabled cellular-based device; and enabling receiving, by such at least one web-browser-based communications software system, at least one delete request relating to such patient appointment data from such at least one wireless-access-protocol-enabled cellular-based device. Even further, it provides such a method, wherein such step of enabling receiving, by such at least one web-browser-based communications software system, at least one function request relating to such at least one medical practice management system from using such at least one wireless-access-protocol-enabled cellular-based device, comprises the steps of: enabling receiving, by such at least one web-browser-based communications software system, at least one search request relating to patient superbill data from such at least one wireless-access-protocol-enabled cellular-based device; and enabling receiving, by such at least one web-browser-based communications software system, at least one view request relating to such patient superbill data from such at least one wireless-access-protocol-enabled cellular-based device. Moreover, it provides such a method, wherein such step of enabling receiving, by such at least one web-browser-based communications software system, at least one function request relating to such at least one medical practice management system from using such at least one wireless-access-protocol-enabled cellular-based device, comprises the steps of: enabling receiving, by such at least one web-browser-based communications software system, at least one modification request relating to such patient superbill data from such at least one wireless-access-protocol-enabled cellular-based device; enabling receiving, by such at least one web-browser-based communications software system, at least one add request relating to such patient superbill data from such at least one wireless-access-protocol-enabled cellular-based device; and enabling receiving, by such at least one web-browser-based communications software system, at least one delete request relating to such patient superbill data from such at least one wireless-access-protocol-enabled cellular-based device. Additionally, it provides such a method, wherein such step of enabling receiving, by such at least one web-browser-based communications software system, at least one function request relating to such at least one medical practice management system from using such at least one wireless-access-protocol-enabled cellular-based device, comprises the steps of: enabling receiving, by such at least one web-browser-based communications software system, at least one search request relating to procedure code data from such at least one wireless-access-protocol-enabled cellular-based device; and enabling receiving, by such at least one web-browser-based communications software system, at least one view request relating to such procedure code data from such at least one wireless-access-protocol-enabled cellular-based device. Also, it provides such a method, wherein such step of enabling receiving, by such at least one web-browser-based communications software system, at least one function request relating to such at least one medical practice management system from using such at least one wireless-access-protocol-enabled cellular-based device, comprises the steps of: enabling receiving, by such at least one web-browser-based communications software system, at least one modification request relating to such procedure code data from such at least one wireless-access-protocol-enabled cellular-based device; enabling receiving, by such at least one web-browser-based communications software system, at least one add request relating to such procedure code data from such at least one wireless-access-protocol-enabled cellular-based device;

and enabling receiving at least one delete request relating to such procedure code data from such at least one wireless-access-protocol-enabled cellular-based device. In addition, it provides such a method, wherein such step of enabling receiving, by such at least one web-browser-based communications software system, at least one function request relating to such at least one medical practice management system from using such at least one wireless-access-protocol-enabled cellular-based device, comprises the steps of: enabling receiving, by such at least one web-browser-based communications software system, at least one search request relating to diagnostic code data from such at least one wireless-access-protocol-enabled cellular-based device; and enabling receiving, by such at least one web-browser-based communications software system, at least one view request relating to such diagnostic code data from such at least one wireless-access-protocol-enabled cellular-based device. And, it provides such a method, wherein such step of enabling receiving, by such at least one web-browser-based communications software system, at least one function request relating to such at least one medical practice management system from using such at least one wireless-access-protocol-enabled cellular-based device, comprises the steps of: enabling receiving, by such at least one web-browser-based communications software system, at least one modification request relating to such diagnostic code data from such at least one wireless-access-protocol-enabled cellular-based device; enabling receiving, by such at least one web-browser-based communications software system, at least one add request relating to such diagnostic code data from such at least one wireless-access-protocol-enabled cellular-based device; and enabling receiving, by such at least one web-browser-based communications software system, at least one delete request relating to such diagnostic code data from such at least one wireless-access-protocol-enabled cellular-based device. Further, it provides such a method, further comprising the steps of: providing at least one usage license to such at least one user; relating such at least one usage license to such at least one user; and restricting access to such at least one web-browser-based communications software to such at least one user related to such provided at least one usage license. Even further, it provides such a method, further comprising the step of receiving payment from such at least one user relating to use of such at least one web-browser-based communications software. Moreover, it provides such a method, further comprising the step of permitting management of usage authorization relating to particular functions, relating to at least one user, by at least one user-manager. Additionally, it provides such a method, further comprising the step of permitting customization of wireless-access-protocol-enabled cellular-based device display preferences by at least one user manager. Also, it provides such a method, wherein such at least one medical practice support system comprises at least one electronic medical record management system. In addition, it provides such a method, further comprising the steps of: enabling detecting, by such at least one web-browser-based communications software system, at least one device type relating to such at least one wireless-access-protocol-enabled cellular-based device used by such at least one user to send such at least one function request; enabling determining, by such at least one web-browser-based communications software system, at least one user interface format compatible with such detected at least one device type; enabling input, by such at least one user, of such at least one function request using such determined at least one user interface format compatible with such at least one wireless-access-protocol-enabled cellular-based device; and enabling display, by such at least one web-browser-based communications software system, of such results of such at least one function request using such determined at least one user interface format. And, it provides such a method, further comprising the steps of: enabling detecting, by such at least one web-browser-based communications software system, at least one device type relating to such at least one wireless-access-protocol-enabled cellular-based device used by such at least one user to send such at least one function request; enabling determining, by such at least one web-browser-based communications software system, at least one user interface format compatible with such detected at least one device type; enabling input, by such at least one user, of such at least one function request using such determined at least one user interface format compatible with such at least one wireless-access-protocol-enabled cellular-based device; and enabling display, by such at least one web-browser-based communications software system, of such results of such at least one function request using such determined at least one user interface format.

In accordance with another preferred embodiment hereof, this invention provides a method comprising the steps of: offering, by at least one software provider, relating to at least one medical practice support system, at least one web-browser-based communications software system to at least one user of at least one at least one wireless-access-protocol-enabled cellular-based device; wherein such at least one medical practice support system is not otherwise web-browser-accessible using the Internet by using such at least one wireless-access-protocol-enabled cellular-based device; communicatively coupling such at least one web-browser-based communications software system to such at least one medical practice support system; permitting access to such at least one web-browser-based communications software system by such at least one user; enabling receiving, by such at least one web-browser-based communications software system, at least one function request relating to such at least one medical practice support system from using such at least one wireless-access-protocol-enabled cellular-based device; enabling transmitting, by such at least one web-browser-based communications software system, such at least one function request to such at least one medical practice support system; enabling receiving, by such at least one web-browser-based communications software system, results of such at least one function request from such at least one medical practice support system; and enabling transmitting such results of such at least one function request to such at least one wireless-access-protocol-enabled cellular-based device; wherein such at least one medical practice support program comprises at least one medical practice management system and at least one electronic medical record software system. Further, it provides such a method, further comprising the steps of: enabling detecting, by such at least one web-browser-based communications software system, at least one device type relating to such at least one wireless-access-protocol-enabled cellular-based device used by such at least one user to send such at least one function request; enabling determining, by such at least one web-browser-based communications software system, at least one user interface format compatible with such detected at least one device type; enabling input, by such at least one user, of such at least one function request using such determined at least one user interface format compatible with such at least one wireless-access-protocol-enabled cellular-based device; and enabling display, by such at least one web-browser-based communications software system, of such results of such at least one function request using such determined at least one user interface format.

In accordance with another preferred embodiment hereof, this invention provides a computer system, relating to assisting web-browser-based communication, by a plurality of users, with a plurality of medical practice management systems not otherwise web-browser-accessible from the Internet, comprising: at least one first computer processor structured and arranged to communicate with at least one first medical practice management system of such plurality of medical practice management systems; at least one first computer interface structured and arranged to permit inputting, by such at least one user of such plurality of users, at least one function request relating to such at least one first medical practice management system from at least one wireless-access-protocol-enabled cellular-based device operated by such at least one user; at least one second computer processor structured and arranged to receive such inputted at least one function request relating to such at least one first medical practice management system; at least one third computer processor structured and arranged to transmit such at least one function request to such at least one first medical practice management system; at least one fourth computer processor structured and arranged to receive results of such at least one function request from such at least one first medical practice management system; at least one fifth computer processor structured and arranged to transmit such results of such at least one function request to such at least one wireless-access-protocol-enabled cellular-based device operated by such at least one user; and at least one second computer interface structured and arranged to present such results of such at least one function request to such at least one user. Even further, it provides such a computer system, further comprising: at least one sixth computer processor structured and arranged to detect at least one wireless-access-protocol-enabled cellular-based device type used by such at least one user to send such at least one function request; at least one seventh computer processor structured and arranged to determine at least one user interface format compatible with such detected at least one wireless-access-protocol-enabled cellular-based device type; at least one third computer interface structured and arranged to permit inputting, by such at least one user, of such at least one function request using such determined at least one user interface format compatible with such at least one wireless-access-protocol-enabled cellular-based device; and at least one fourth computer interface structured and arranged to display such results of such at least one function request using such determined at least one user interface format compatible with such at least one wireless-access-protocol-enabled cellular-based device. Moreover, it provides such a computer system, wherein such inputted at least one function request relating to such at least one first medical practice management system comprises: at least one search request relating to patient demographic data; and at least one view request relating to such patient demographic data. Additionally, it provides such a computer system, wherein such inputted at least one function request relating to such at least one first medical practice management system comprises: at least one search request relating to patient demographic data; at least one view request relating to such patient demographic data; at least one modification request relating to such patient demographic data; at least one add request relating to such patient demographic data; and at least one delete request relating to such patient demographic data. Also, it provides such a computer system, wherein such inputted at least one function request relating to such at least one first medical practice management system comprises: at least one search request relating to patient appointment data; and at least one view request relating to such patient appointment data from such at least one user. In addition, it provides such a computer system, wherein such inputted at least one function request relating to such at least one first medical practice management system comprises: at least one modification request relating to such patient appointment data; at least one add request relating to such patient appointment data; and at least one delete request relating to such patient appointment data. And, it provides such a computer system, wherein such inputted at least one function request relating to such at least one first medical practice management system comprises: at least one search request relating to patient superbill data; and at least one view request relating to such patient superbill data. Further, it provides such a computer system, wherein such inputted at least one function request relating to such at least one first medical practice management system comprises: at least one search request relating to patient superbill data; at least one view request relating to such patient superbill data; at least one modification request relating to such patient superbill data; at least one add request relating to such patient superbill data; and at least one delete request relating to such patient superbill data. Even further, it provides such a computer system, wherein such inputted at least one function request relating to such at least one first medical practice management system comprises: at least one search request relating to procedure code data; and at least one view request relating to such procedure code data. Moreover, it provides such a computer system, wherein such inputted at least one function request relating to such at least one first medical practice management system comprises: at least one modification request relating to such procedure code data; at least one add request relating to such procedure code data; and at least one delete request relating to such procedure code data. Additionally, it provides such a computer system, wherein such inputted at least one function request relating to such at least one first medical practice management system comprises: at least one search request relating to diagnostic code data; and at least one view request relating to such diagnostic code data. Also, it provides such a computer system, wherein such inputted at least one function request relating to such at least one first medical practice management system comprises: at least one modification request relating to such diagnostic code data from; at least one add request relating to such diagnostic code data; and at least one delete request relating to such diagnostic code data. In addition, it provides such a computer system, further comprising: at least one first computer storage structured and arranged to store at least one usage license in at least one usage license database; at least one eighth computer processor structured and arranged to relate such at least one usage license to such at least one user; and at least one ninth computer processor structured and arranged to restrict access to such at least one user related to such stored at least one usage license.

In accordance with another preferred embodiment hereof, this invention provides a computer software program, relating to assisting web-browser-based communication, by a plurality of users, with at least one medical practice support system, comprising: establishing communication with at least one medical practice support system; permitting sending, by at least one user, at least one function request relating to such at least one medical practice support system from at least one wireless-access-protocol-enabled cellular-based device operated by such at least one user; receiving such sent at least one function request relating to such at least one first medical practice support system; transmitting such at least one function request to such at least one first medical practice support system; receiving results of such at least one function request from such at least one first medical practice support system;

transmitting such results of such at least one function request to such at least one wireless-access-protocol-enabled cellular-based device; and presenting such results of such at least one function request to such at least one user. And, it provides such a computer software program, further comprising: detecting at least one device type relating to such at least one wireless-access-protocol-enabled cellular-based device used by such at least one user to send such at least one function request; determining at least one user interface format compatible with such detected at least one device type; permitting inputting, by such at least one user, of such at least one function request using such determined at least one user interface format compatible with such at least one wireless-access-protocol-enabled cellular-based device; and displaying such results of such at least one function request using such determined at least one user interface format compatible with such at least one wireless-access-protocol-enabled cellular-based device.

In accordance with another preferred embodiment hereof, this invention provides a method, relating to providing, by at least one software provider, assistance relating to web-browser-based communication, by a plurality of users, with at least one of a plurality of medical practice management systems not otherwise web-browser-accessible from the Internet, comprising the steps of: offering at least one web-browser-based communications software system to at least one first user of such plurality of users; assisting identifying at least one medical practice management system of such plurality of medical practice management systems; communicatively coupling such at least one web-browser-based communications software system to such identified at least one medical practice management system; permitting access to such web-browser-based communications software system by such at least one user; enabling receiving, by such at least one web-browser-based communications software system, at least one function request relating to such identified at least one medical practice management system from at least one input/output device operated by such at least one user; enabling transmitting, by such at least one web-browser-based communications software system, such at least one function request to such identified at least one medical practice management system; enabling receiving, by such at least one web-browser-based communications software system, results of such at least one function request from such identified at least one medical practice management system; and enabling transmitting such results of such at least one function request to such at least one input/output device operated by such at least one user.

In accordance with another preferred embodiment hereof, this invention provides a method comprising the steps of: offering, by at least one software provider, relating to at least one medical practice support system, at least one web-browser-based communications software system to at least one user of at least one at least one wireless-access-protocol-enabled cellular-based device; wherein such at least one medical practice support system is not otherwise web-browser-accessible using the Internet by using such at least one wireless-access-protocol-enabled cellular-based device; communicatively coupling such at least one web-browser-based communications software system to such at least one medical practice support system; permitting access to such at least one web-browser-based communications software system by such at least one user; enabling receiving, by such at least one web-browser-based communications software system, at least one function request relating to such at least one medical practice support system from using such at least one wireless-access-protocol-enabled cellular-based device; enabling transmitting, by such at least one web-browser-based communications software system, such at least one function request to such at least one medical practice support system; enabling receiving, by such at least one web-browser-based communications software system, results of such at least one function request from such at least one medical practice support system; and enabling transmitting such results of such at least one function request to such at least one wireless-access-protocol-enabled cellular-based device; enabling detecting, by such at least one web-browser-based communications software system, at least one device type relating to such at least one wireless-access-protocol-enabled cellular-based device used by such at least one user to send such at least one function request; enabling determining, by such at least one web-browser-based communications software system, at least one user interface format compatible with such detected at least one device type; enabling input, by such at least one user, of such at least one function request using such determined at least one user interface format compatible with such at least one wireless-access-protocol-enabled cellular-based device; and enabling display, by such at least one web-browser-based communications software system, of such results of such at least one function request using such determined at least one user interface format; wherein such step of enabling receiving, by such at least one web-browser-based communications software system, at least one function request relating to such at least one medical practice support system from such at least one wireless-access-protocol-enabled cellular-based device, comprises the steps of enabling receiving, by such at least one web-browser-based communications software system, at least one search request relating to patient demographic data from such at least one wireless-access-protocol-enabled cellular-based device operated by such at least one user; and enabling receiving, by such at least one web-browser-based communications software system, at least one view request relating to such patient demographic data from such at least one wireless-access-protocol-enabled cellular-based device operated by such at least one user; enabling receiving, by such at least one web-browser-based communications software system, at least one modification request relating to such patient demographic data from such at least one wireless-access-protocol-enabled cellular-based device operated by such at least one user; enabling receiving, by such at least one web-browser-based communications software system, at least one add request relating to such patient demographic data from such at least one wireless-access-protocol-enabled cellular-based device operated by such at least one user; and enabling receiving, by such at least one web-browser-based communications software system, at least one delete request relating to such patient demographic data from such at least one wireless-access-protocol-enabled cellular-based device operated by such at least one user. enabling receiving, by such at least one web-browser-based communications software system, at least one search request relating to patient appointment data from such at least one wireless-access-protocol-enabled cellular-based device; and enabling receiving, by such at least one web-browser-based communications software system, at least one view request relating to such patient appointment data from such at least one wireless-access-protocol-enabled cellular-based device. enabling receiving, by such at least one web-browser-based communications software system, at least one modification request relating to such patient appointment data from such at least one input/output device operated by such at least one user; enabling receiving, by such at least one web-browser-based communications software system, at least one add request relating to such patient appointment data from such at least one input/output device operated by such at least one user; and enabling receiving, by such at least one web-browser-based communications software system, at least one delete request relating to such patient appointment data from such at least one input/output device operated by such at least one user. enabling receiving, by such at least one web-browser-based communications software system, at least one search request relating to patient superbill data from such at least one wireless-access-protocol-enabled cellular-based device; and enabling receiving, by such at least one web-browser-based communications software system, at least one view request relating to such patient superbill data from such at least one wireless-access-protocol-enabled cellular-based device. enabling receiving, by such at least one web-browser-based communications software system, at least one modification request relating to such patient superbill data from such at least one user; enabling receiving, by such at least one web-browser-based communications software system, at least one add request relating to such patient superbill data from such at least one wireless-access-protocol-enabled cellular-based device; and enabling receiving, by such at least one web-browser-based communications software system, at least one delete request relating to such patient superbill data from such at least one wireless-access-protocol-enabled cellular-based device. enabling receiving, by such at least one web-browser-based communications software system, at least one search request relating to procedure code data from such at least one wireless-access-protocol-enabled cellular-based device; and enabling receiving, by such at least one web-browser-based communications software system, at least one view request relating to such procedure code data from such at least one wireless-access-protocol-enabled cellular-based device; enabling receiving, by such at least one web-browser-based communications software system, at least one modification request relating to such procedure code data from such at least one wireless-access-protocol-enabled cellular-based device; enabling receiving, by such at least one web-browser-based communications software system, at least one add request relating to such procedure code data from such at least one wireless-access-protocol-enabled cellular-based device; and enabling receiving at least one delete request relating to such procedure code data from such at least one wireless-access-protocol-enabled cellular-based device. enabling receiving, by such at least one web-browser-based communications software system, at least one search request relating to diagnostic code data from such at least one wireless-access-protocol-enabled cellular-based device; and enabling receiving, by such at least one web-browser-based communications software system, at least one view request relating to such diagnostic code data from such at least one wireless-access-protocol-enabled cellular-based device. enabling receiving, by such at least one web-browser-based communications software system, at least one modification request relating to such diagnostic code data from such at least one wireless-access-protocol-enabled cellular-based device; enabling receiving, by such at least one web-browser-based communications software system, at least one add request relating to such diagnostic code data from such at least one wireless-access-protocol-enabled cellular-based device; and enabling receiving, by such at least one web-browser-based communications software system, at least one delete request relating to such diagnostic code data, from such at least one wireless-access-protocol-enabled cellular-based device.

DEFINITIONS AND ACRONYMS

The following terms and acronyms are explained below as background and are used throughout the detailed description:

Cascading Style Sheet (CSS). In computing, Cascading Style Sheets (CSS) is a style sheet language used to describe the presentation of a document written in a markup language. It's most common application is to style web pages written in HTML and XHTML. The CSS specifications are maintained by the World Wide Web Consortium (W3C). CSS is used by both the authors and readers of web pages to define colors, fonts, layout, and other aspects of document presentation. It is designed primarily to enable the separation of document content (written in HTML or a similar markup language) from document presentation (written in CSS). Multiple style sheets can be imported, and alternative style sheets can be specified so that the user can choose between them. Different styles can be applied depending on the output device being used. For example, the screen version may be quite different from the printed version. This allows authors to tailor the presentation appropriately for each kind of media.

Client-Server. A model of interaction in a distributed system in which a program at one site sends a request to a program at another site and waits for a response. The requesting program is called the "client," and the program that responds to the request is called the "server." In the context of the World Wide Web, the client is typically a "Web browser" that runs on a user's computer; the program that responds to Web browser requests at a Web site is commonly referred to as a "Web server."

Current Procedural Terminology (CPT Codes). The list maintained by the American Medical Association to provide unique billing codes for services rendered by physicians and other medical practitioners. The current version is the CPT-4. It currently is used as Level 1 of the Health Care Procedure Coding System. The American Medical Association states that these codes are "the most widely accepted medical nomenclature used to report medical procedures and services under public and private health insurance programs."

Database. One or more large structured sets of persistent data maintained upon a computer system organized and structured according to a software system defining rules for organization as well responding to queries to read, write or modify data as well as provide statistical information regarding the contained data. As used herein for purposes of discussion, a database may be either a single unified system or a distributed system wherein certain database elements are located upon different systems, acting in harmony to appear as one unified database.

Diagnostic codes. In medicine, Diagnostic codes are used to group and identify diseases, disorders, symptoms, and medical signs, and are used to measure morbidity and mortality. A widely used set of diagnostic codes is ICD (International Statistical Classification of Diseases and Related Health Problems) which is a detailed description of known diseases and injuries. Every disease (or group of related diseases) is described with its diagnosis and given a unique code, up to six characters long. ICD is published by the World Health Organization and is used world-wide for morbidity and mortality statistics, reimbursement systems and automated decision support in medicine. The system is designed to promote international comparability in the collection, processing, classification, and presentation of these statistics. It is revised periodically and is currently in its tenth edition—ICD-10.

Domain Name. The "www.domain.com" portion of the URL is called a "domain name." The domain name is a unique Internet alphanumeric address that identifies the virtual location of Internet resources related to a particular organization. For example, URLs containing the domain name "www.realtorXYZ.com" might include resources related to a company fictionally named Realtor XYZ.

Domain Name System (DNS). An Internet service that translates domain names (which are alphabetic identifiers) into IP addresses (which are numeric identifiers for machines on a TCP/IP network).

Extensible Markup Language (XML). XML describes a class of data objects known as XML documents and partially describes the behavior of computer programs which process these documents. More specifically, XML is a restricted form of the Standard Generalized Markup Language (also known as SGML). XML documents are made up of storage units defined as entities which in turn comprise either parsed or unparsed data in the form of characters or simply a character. XML is designed and intended to improve the functionality of the Internet by providing more flexible and adaptive forms of information. XML can be used to store any kind of structured information and in such encapsulated form, pass it between different computer systems which would otherwise be unable to communicate.

File Transport Protocol (FTP). The protocol used on the Internet for exchanging files. FTP is most commonly used to download a file from a server using the Internet or to upload a file to a server (e.g., uploading a Web page file to a server).

Hypertext Markup Language (HTML). A standard coding convention and set of codes for attaching presentation and linking attributes to informational content within documents. During a document authoring stage, the HTML codes (referred to as "tags") are embedded within the informational content of the document. When the Web document (or "HTML document") is subsequently transferred from a Web server to a Web browser, the codes are interpreted by the Web browser and used to parse and display the document. In addition to specifying how the Web browser is to display the document, HTML tags can be used to create links to other websites and other Web documents (commonly referred to as "hyperlinks") For more information on HTML, see Ian S. Graham, The HTML Source Book, John Wiley and Sons, Inc., 1995 (ISBN 0471-11894-4).

Hypertext Transport Protocol (HTTP). The standard World Wide Web client-server protocol used for the exchange of information (such as HTML documents and client requests for such documents) between a Web browser and a Web server. HTTP includes a number of different types of messages that can be sent from the client to the server to request different types of server actions. For example, a "GET" message, which has the format GET, causes the server to return the document or file located at the specified Universal Resource Locator (URL).

HTTPS. HTTP over SSL (Secure Sockets Layer) can be best understood as a secure form of HTTP communication. Specifically, SSL is a protocol utilized for the authentication and encryption of HTTP traffic. In operation, the server and client exchange a set of encryption keys that are used to create a unique encryption key used to encrypt all data exchanged during the session.

Internet. A collection of interconnected (public and/or private) networks that are linked together by a set of standard protocols to form a distributed network. While this term is intended to refer to what is now commonly known as the Internet, it is also intended to encompass variations that may be made in the future, including changes and additions to existing standard protocols.

LAN. A Local Area Network of computer systems, typically within a building or office, permitting networking, the associated sharing of resources and files, such as application software, printers and client information, in an inter-office setting.

Meta-tag. Meta-tags are HTML elements used to provide structured metadata about a web page. Such elements are placed as tags in the head section of an HTML document. The two most common uses of meta-tags on the web are to provide a description and to provide keywords for a webpage. This data may then be used by search engines to generate and display a list of search results matching a given query. Meta-tags such as these have been the focus of a field of marketing research known as search engine optimization (SEO). In the mid to late 1990s, search engines were reliant on meta-tag data to correctly classify a web page.

Microsoft IIS (Internet Information Services) Server. A set of Internet-based services for servers using Microsoft Windows.

Microsoft.net Framework. Commonly known as simply the .NET Framework, is a software development platform created by Microsoft. .NET Framework is a Microsoft technology that allows cross-language development and provides a large standard library. Other competing approaches are cross-platform languages, i.e. Perl, using a cross-platform runtime like the Java Virtual Machine, or compile standard ANSI C to each platform.

PHP. (The initials come from the earliest version of the program, which was called "Personal Home Page Tools") A server-side, cross-platform, HTML-embedded scripting language used to create dynamic web pages. PHP is Open Source software.

Secure Sockets Layer (SSL)/Transport Layer Security (TLS). Cryptographic protocols which provide secure communications on the Internet for such things as web browsing, e-mail, Internet faxing, and other data transfers. There are slight differences between SSL 3.0 and TLS 1.0, but the protocol remains substantially the same. The SSL/TLS protocol(s) allow client/server applications to communicate in a way designed to prevent eavesdropping, tampering, and message forgery. SSL/TLS provides endpoint authentication and communications privacy over the Internet using cryptography.

Session ID. In the case of transport protocols which do not implement a formal session layer sessions are maintained by a higher level program using a method defined in the data being exchanged. For example, an HTTP exchange between a browser and a remote host may include an HTTP cookie which identifies state, such as a unique session ID, information about the user's preferences or authorization level.

Structured Query Language (SQL). SQL is a standard language used to communicate with relational database management systems (such as Oracle, Sybase, Microsoft SQL Server, Access, etc.) for the purpose of performing tasks such as data insertion, deletion, update, and general query for the return of data.

Simple Object Access Protocol (SOAP). SOAP is a lightweight XML/HTTP-based protocol for the exchange of information in a decentralized distributed platform-independent environment. Fundamentally, SOAP consists of three parts. The first is an envelope that defines a framework for describing what is contained in the message and how it should be processed. The second is a set of encoding rules for expressing instances of application-defined data types. The third is a normalized convention for representing remote procedure calls and responses.

Superbill. A checklist of procedures and diagnoses used to indicate the procedures that are performed during an office visit. Once completed by the provider, it becomes the basis for entering transactions. Also known as a routing slip Transmission Control Protocol/Internet Protocol (TCP/IP). A standard Internet protocol (or set of protocols) which specifies how two computers exchange data over the Internet. TCP/IP handles issues such as packetization, packet addressing, and handshaking and error correction. For more information on TCP/IP, see Volumes I, II and III of corner and Stevens, Internetworking with TCP/IP, Prentice Hall, Inc., ISBNs 0-13-468505-9 (vol. I), 0-13-125527-4 (vol. II), and 0-13-474222-2 (vol. III).

Uniform Resource Locator (URL). A unique address which fully specifies the location of a file or other resource on the Internet. The general format of a URL is protocol://machine address:port/path/filename. The port specification is optional, and, if not entered by the user, the Web browser defaults to the standard port for whatever service is specified as the protocol. For example, if HTTP is specified as the protocol, the Web browser will use the HTTP default port. The machine address in this example is the domain name for the computer or device on which the file is located.

Universal Serial Bus (USB). USB provides a serial bus standard for connecting devices, usually to a computer, but it also is in use on other devices such as set-top boxes, game consoles. USB can connect peripherals such as mice, keyboards, gamepads and joysticks, scanners, digital cameras, printers, hard disks, and networking components.

Web Browser. A software application that enables a user to display and interact with text, images, and other information typically located on a web page at a website on the World Wide Web or a local area network. Text and images on a web page can contain hyperlinks to other web pages at the same or different websites. Web browsers allow a user to quickly and easily access information provided on many web pages at many websites by traversing these links. Web browsers available for personal computers include Microsoft Internet Explorer, Mozilla Firefox, Apple Safari, Netscape, and Opera. Web browsers are the most commonly used type of HTTP user agent. Although browsers are typically used to access the World Wide Web, they can also be used to access information provided by web servers in private networks or content in file systems.

WAN. A Wide Area Network, such as the Internet.

Wireless Application Protocol (WAP). An open international standard for applications that use wireless communication. Its principal application is to enable access to the internet from a mobile phone or PDA (personal digital assistant). A WAP browser is designed to provide all of the basic services of a computer based web browser but simplified to operate within the restrictions of a mobile phone. WAP is now the protocol used for the majority of the world's mobile internet sites, known as WAP sites. Mobile internet sites, or WAP sites, are websites written in, or dynamically converted to, WML (Wireless Markup Language) and accessed via the WAP browser.

World Wide Web ("Web"). Used herein to refer generally to both (1) a distributed collection of interlinked, user-viewable hypertext documents (commonly referred to as "Web documents", "Web pages", "electronic pages" or "home pages") that are accessible via the Internet, and (2) the client and server software components that provide user access to such documents using standardized Internet protocols. Currently, the primary standard protocol for allowing applications to locate and acquire Web documents is the Hypertext Transfer Protocol (HTTP), and the electronic pages are encoded using the Hypertext Markup Language (HTML). However, the terms "World Wide Web" and "Web" are intended to encompass future markup languages and transport protocols that may be used in place of or in addition to the Hypertext Markup Language (HTML) and the Hypertext Transfer Protocol (HTTP).

BRIEF DESCRIPTION OF THE DRAWINGS

FIG. 51 shows an example of the Patient New Entries Search Results screen of the Admin Doctor Application according to a preferred embodiment of the present invention.

FIG. 52 shows an example of the Appointment New Entries Search Results screen of the Admin Doctor Application according to a preferred embodiment of the present invention.

FIG. 53 shows an example of the Superbill New Entries Search Results screen of the Admin Doctor Application according to a preferred embodiment of the present invention.

FIG. 54 shows an example of the CPT New Entries Search Results screen of the Admin Doctor Application according to a preferred embodiment of the present invention.

FIG. 55 shows an example of the Diagnosis New Entries Search Results screen of the Admin Doctor Application according to a preferred embodiment of the present invention.

FIG. 56 shows an example of the Rules Wizard screen of the Admin Doctor Application according to a preferred embodiment of the present invention.

FIG. 57 shows an example of the results of a CPT Code search of the Rules of the Admin Doctor Application according to a preferred embodiment of the present invention.

FIG. 58 shows an example of the Add Rule screen of the Admin Doctor Application according to a preferred embodiment of the present invention.

FIG. 59 shows an example of the Search Place of Service screen of the account settings of the Admin Doctor Application according to a preferred embodiment of the present invention.

FIG. 60 shows an example of the results of a search performed with the Search Place of Service screen of FIG. 59.

FIG. 61 shows an example of the Add Place of Service feature of the account settings of the Admin Doctor Application according to a preferred embodiment of the present invention.

FIG. 63 shows an example of the Edit Place of Service feature of the account settings of the Admin Doctor Application according to a preferred embodiment of the present invention.

FIG. 65 shows an example of the Delete Place of Service screen of the account settings of the Admin Doctor Application according to a preferred embodiment of the present invention.

FIG. 68 shows an example of the Search Patient Category feature of the account settings of the Admin Doctor Application according to a preferred embodiment of the present invention.

FIG. 69 shows an example of the results of a search performed with the Search Patient Category feature shown in FIG. 68.

FIG. 70 shows an example of the Add Patient Category feature of the account settings of the Admin Doctor Application according to a preferred embodiment of the present invention.

FIG. 71 shows an example of the Add Patient Category Screen of the Admin Doctor Application according to a preferred embodiment of the present invention.

FIG. 72 shows an example of the Edit Patient Category feature of the Admin Doctor Application according to a preferred embodiment of the present invention.

FIG. 73 shows an example of the Edit Patient Category Screen of the Admin Doctor Application according to a preferred embodiment of the present invention.

FIG. 74 shows an example of the Delete Patient Category feature of the Admin Doctor Application according to a preferred embodiment of the present invention.

FIG. 75 shows an example of a Customize View Superbill in Mobile screen of the Admin Doctor Application according to a preferred embodiment of the present invention.

DETAILED DESCRIPTION OF THE BEST MODES AND PREFERRED EMBODIMENTS OF THE INVENTION

Figure 1:
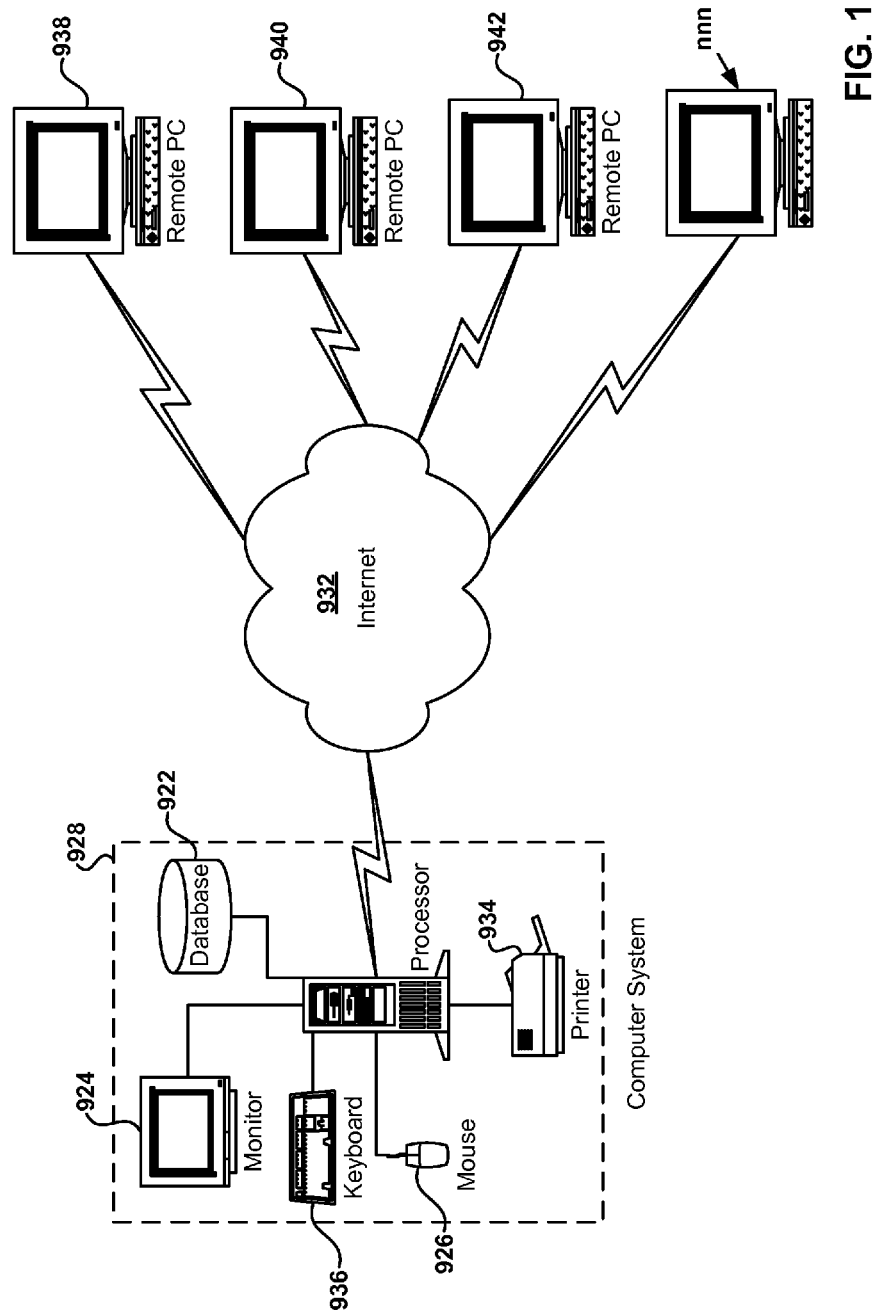
FIG. 1 shows an overview schematic representation of the computer hardware and Internet environment utilized by the Remote Access Management System according to a preferred embodiment of the present invention.

Referring to FIG. 1, an overview schematic representation of the computer hardware and Internet environment utilized by Remote Access Management System 200 according to a preferred embodiment of the present invention is shown. The computer hardware environment comprises Computer System 928. Computer System 928 comprises input and output devices as is well known in the art. For example, Computer System 928 preferably comprises a display screen, or Monitor 924, Keyboard 936, Printer 934, Mouse 926, etc. Computer System 928 further preferably comprises Database 922 for storage of the data and software comprising preferred embodiments of the present invention. Computer System 928 is preferably connected to Internet 932 which serves as the presently preferred communications medium. Internet 932, as previously discussed, comprises a global network connecting local and regional networks and computers, public and private. The Internet 932 is the preferable connection method by Remote PC 938, Remote PC 940, Remote PC 942 and Remote PC nnn to Computer System 928 in preferred embodiments of the present invention.

Figure 2:
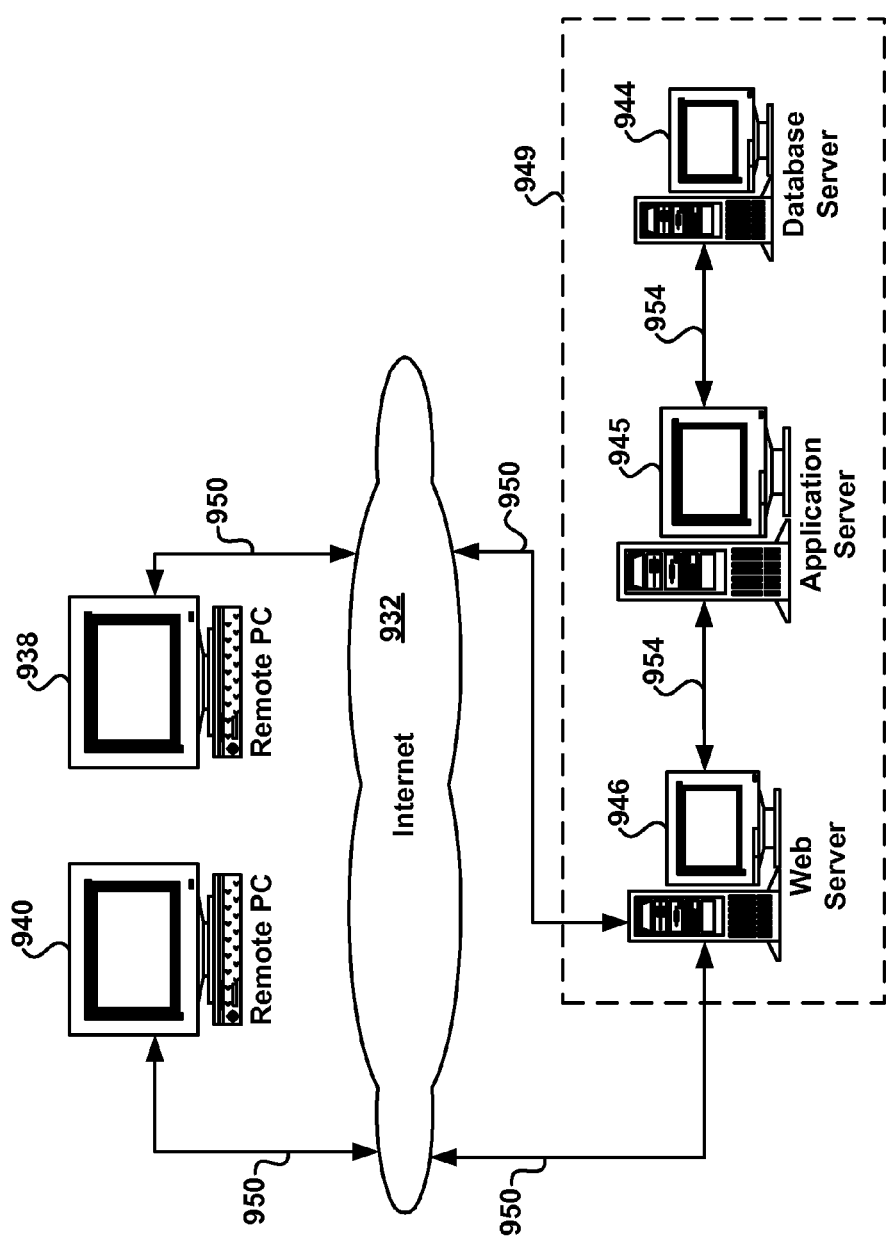
FIG. 2 shows a simplified functional diagram illustrating a preferred web server implementation for operating the Remote Access Management System according to a preferred embodiment of the present invention.

Referring to FIG. 2, a simplified functional diagram illustrating a preferred web server implementation for operating the Remote Access Management System 200 according to a preferred embodiment of the present invention is shown. This figure shows the preferred relationships between Remote PC 938 (as an example of any number of Remote PCs 940, 942, nnn), Internet 932, Web Server 946, Application Server 945 and Database server 944. As shown, a Remote PC 938 requests a page from the Web Site 949 where a preferred embodiment of the present invention is preferably located. Remote PC 938 is preferably connected via Internet 932 to Web Server 946, which receives the web page request and initiates a call to Application Server 945. A preferred embodiment of the present invention installed on Application Server 945 then makes at least one request to Database Server 944 and generates an HTML page for transmission to Remote PC 938 following completion of a request and transmission of the requested data back to the Application Server 945 by Database Server 944. Web Server 946 then transmits the completed HTML page containing the data requested by Remote PC 938 through Internet 932 to Remote PC 938. Connection 954 is typically a TCP-IP connection, or other connection which permits communication between Application Server 945 and Database Server 944 and between Application Server 945 and Web Server 946. Connection 950 is typically TCP-IP and permits Remote PC 938 and Remote PC 940 to communicate with Web Server 946.

Referring again to FIG. 2, access from the Internet to Web Server 946 is preferably via the HTTP or HTTPS protocol and is restricted to a specific port (e.g., port 8080) on the machine running the web server 946. (Note: when using SSL this is port 8083). Using a hardware firewall, the first point of entry preferably can be further restricted to a specific port (e.g., port 80) and a set of IP ranges. The database may run on the same server as the application server. Alternatively, preferably a cluster of two or more servers may run the application server along with a separate server for the database. A similar configuration is preferably needed at a provider's data center.

Preferably, application logic is divided into components according to function; and the various application components are installed on different machines depending on the tier on which the application component belongs:

1. Preferably, client-tier components run on a client machine.
2. Preferably, web-tier components and business-tier components run on a web server and an application server. (As noted, the web-tier and business-tier components may both be run on a single server which acts as both a web server and an application server.)
3. Preferably, enterprise information system (EIS)-tier components run on the database server.

Although a web application can consist of three or four tiers, multi-tiered applications are generally three-tiered applications because they are distributed over different locations: client machines, the application server machine, and the database machines at the back end. Three-tiered applications that run in this way extend the standard two-tiered client/server model by placing a multithreaded application server between the client application and back-end storage server.

The preferred user interface for standard desktop web browsers are preferably developed as rich Internet applications (RIA), providing the user with a much more vivid experience that is similar to desktop applications. Preferably, this is accomplished using client-side JavaScript and/or DHTML using an asynchronous JavaScript and XML (AJAX) technology.

Figure 3:
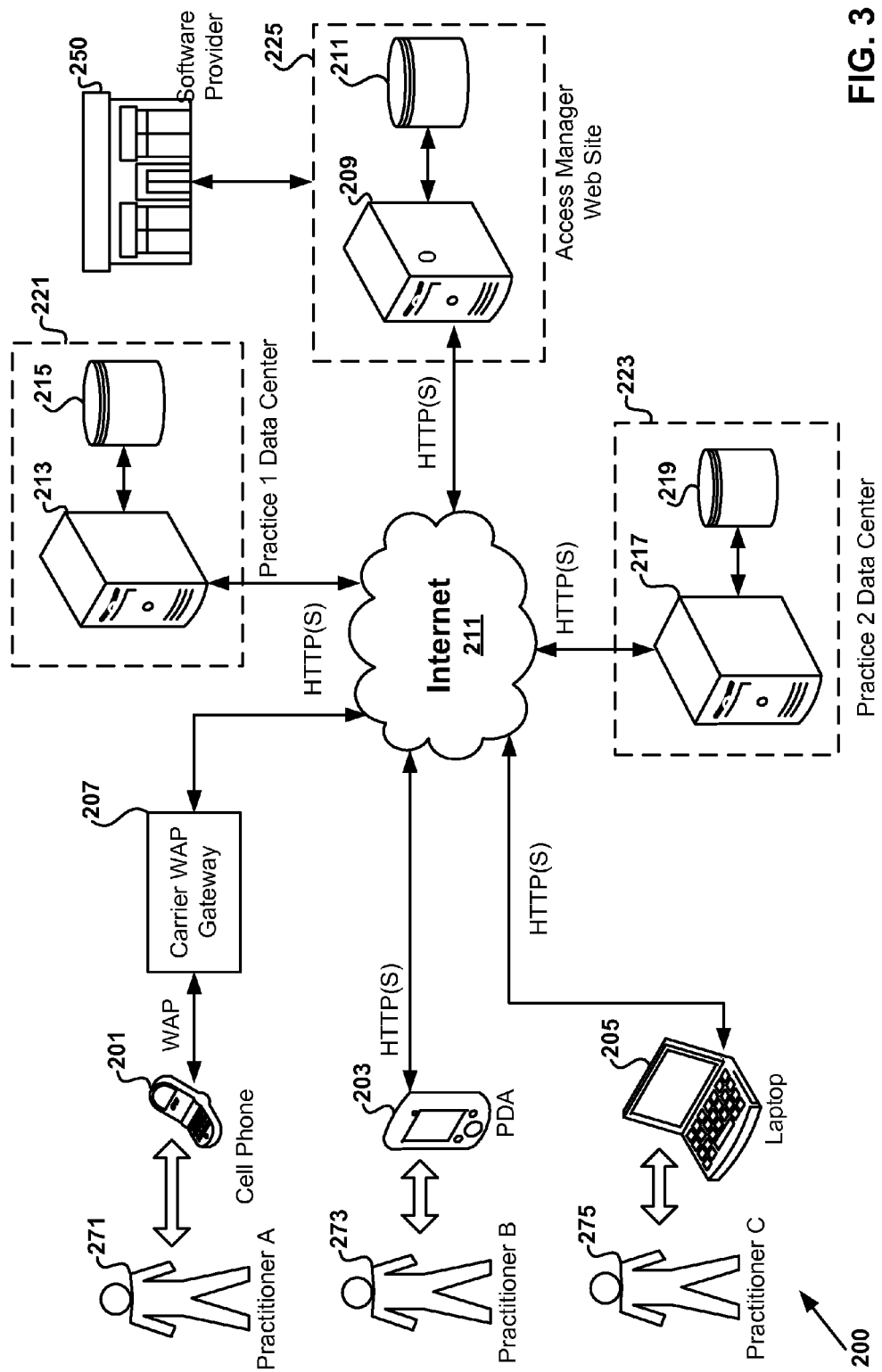
FIG. 3 shows a simplified schematic of the overall communications and control architecture used by the Remote Access Management System according to a preferred embodiment of the present invention.
Figure 4A:
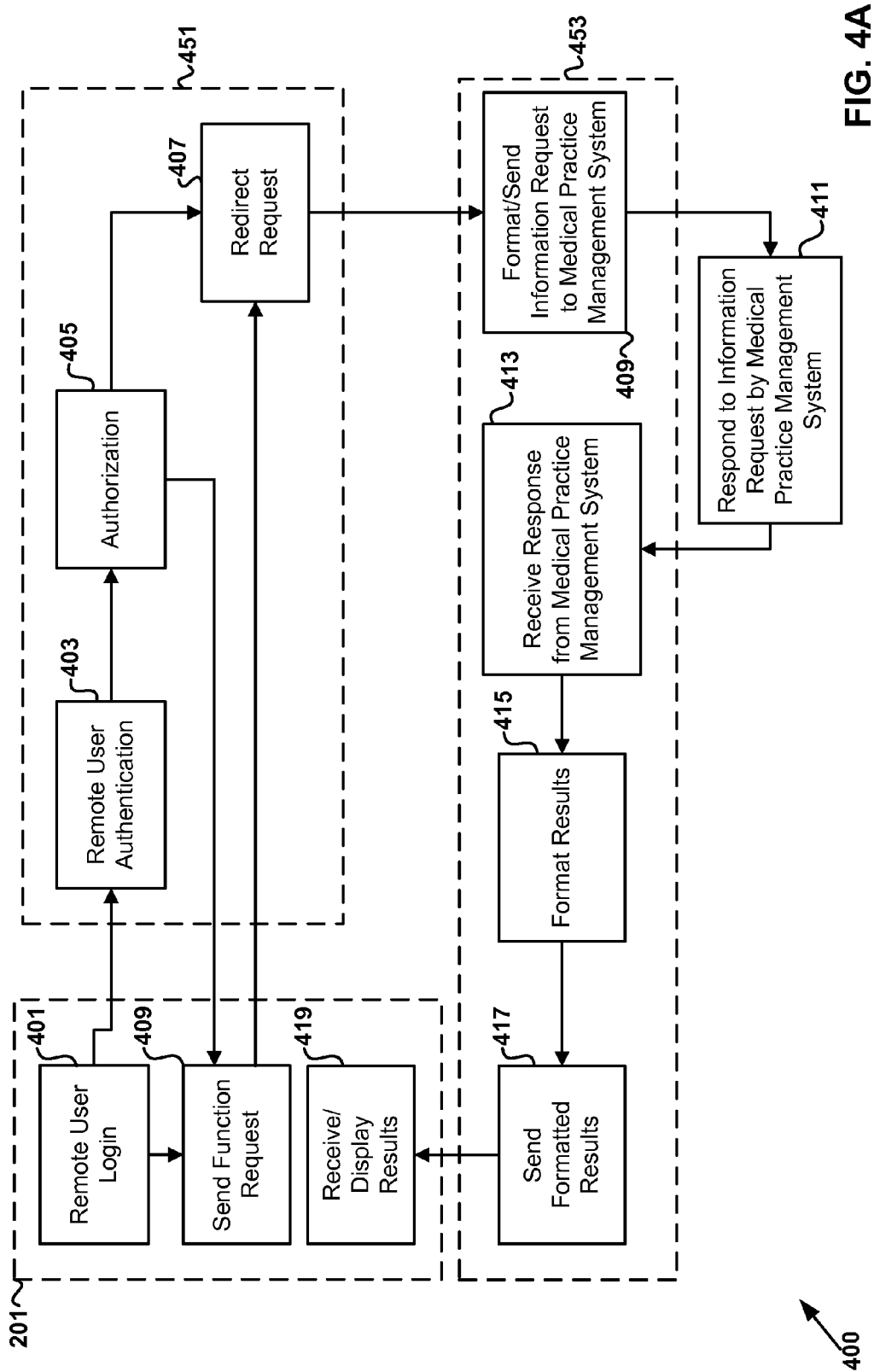
FIG. 4A shows a simplified schematic illustration of the preferred primary computer-related operations associated with use of the Remote Access Management System according to a preferred embodiment of the present invention.

Referring to FIG. 3, which shows a simplified schematic of the overall communications architecture used by Remote Access Management System 200 according to a preferred embodiment of the present invention, the preferred architecture uses a multi-tiered distributed application model. Preferably, Software Provider 250 implements the software modules comprising Access Manager 451 (shown in FIG. 4A) on Access Manager Server 209 and manages information relating to licensing and authorizations relating to Medical Practice 1 503 (shown in FIG. 4B). Preferably, the licensing and authorization information relating to Medical Practice 1 503 is stored on Access Manager Database 211 for reference and update by Access Manager 451. Preferably, Access Manager Server 209 is connected to Internet 211 using standard TCP-IP and HTTP or HTTPS protocols to permit communication between Access Manager 451 and Practice Management System Interface Module 453. Preferably, Practice Management System Interface Module 453 (as shown in FIG. 4A) is implemented on Practice 1 Computer 213 and on Practice 2 Computer 217 and preferably manages communication between the medical practice management system and various remote devices that are web enabled such as Cell Phone 201 (at least herein embodying at least one wireless-access-protocol-enabled cellular-based device), PDA 203 and Laptop 205. Preferably, no software components specifically relating to Remote Access Management System 200 are required to be permanently installed on any remote device; thus remote access to a medical practice support system may be accomplished from any web-browser-enabled or WAP-enabled device capable of using the Internet 211. For the purposes of this disclosure, the term medical practice support system is defined herein to mean medical practice management systems and electronic medical record software systems. Medical practice management systems are designed to assist doctors and physicians (and related individuals) to manage a medical practice (billing, scheduling, etc.). Electronic medical record software systems assist in the tracking medical information of patients and may be used to electronically fill prescriptions or electronically write to the medical record of a patient. For the purposes of discussion with respect to FIG. 4A to FIG. 75, reference is made to a medical practice management system. It is understood that the preferred methods and preferred embodiments disclosed herein may also apply to electronic medical records systems as shown with respect to FIG. 76.

Typically, Practice 1 Data Center 221 comprises at least Practice 1 Computer 213 and Practice 1 Database 215. Typically medical practice management system, which is not web-browser enabled for remote access, is implemented on Practice 1 Computer 213 and uses Practice 1 Database 215 to store information relating to the operation of medical practice management system on behalf of Medical Practice 1. Similarly, Practice 2 Data Center 223 comprises at least Practice 2 Computer 217 and Practice 2 Database 219. Typically, medical practice management system which is not web-browser enabled for remote access is implemented on Practice 2 Computer 217 and uses Practice 2 Database 219 to store information relating to the operation of medical practice management system. Examples of medical practice management systems which are not web-browser enabled for remote access include Lytec software and Medisoft software offered by Per-Se Physician Services. Upon reading the teachings of this specification, those with ordinary skill in the art will now understand that, under appropriate circumstances, considering such issues as agreements with other providers of medical practice management systems, user preferences, changes in the competitive environment, user location, etc., other medical practice management systems products, such as DrWorks offered by MedStar Systems, AccuMed offered by Accumedic Computer Systems, etc., may suffice.

Figure 6:
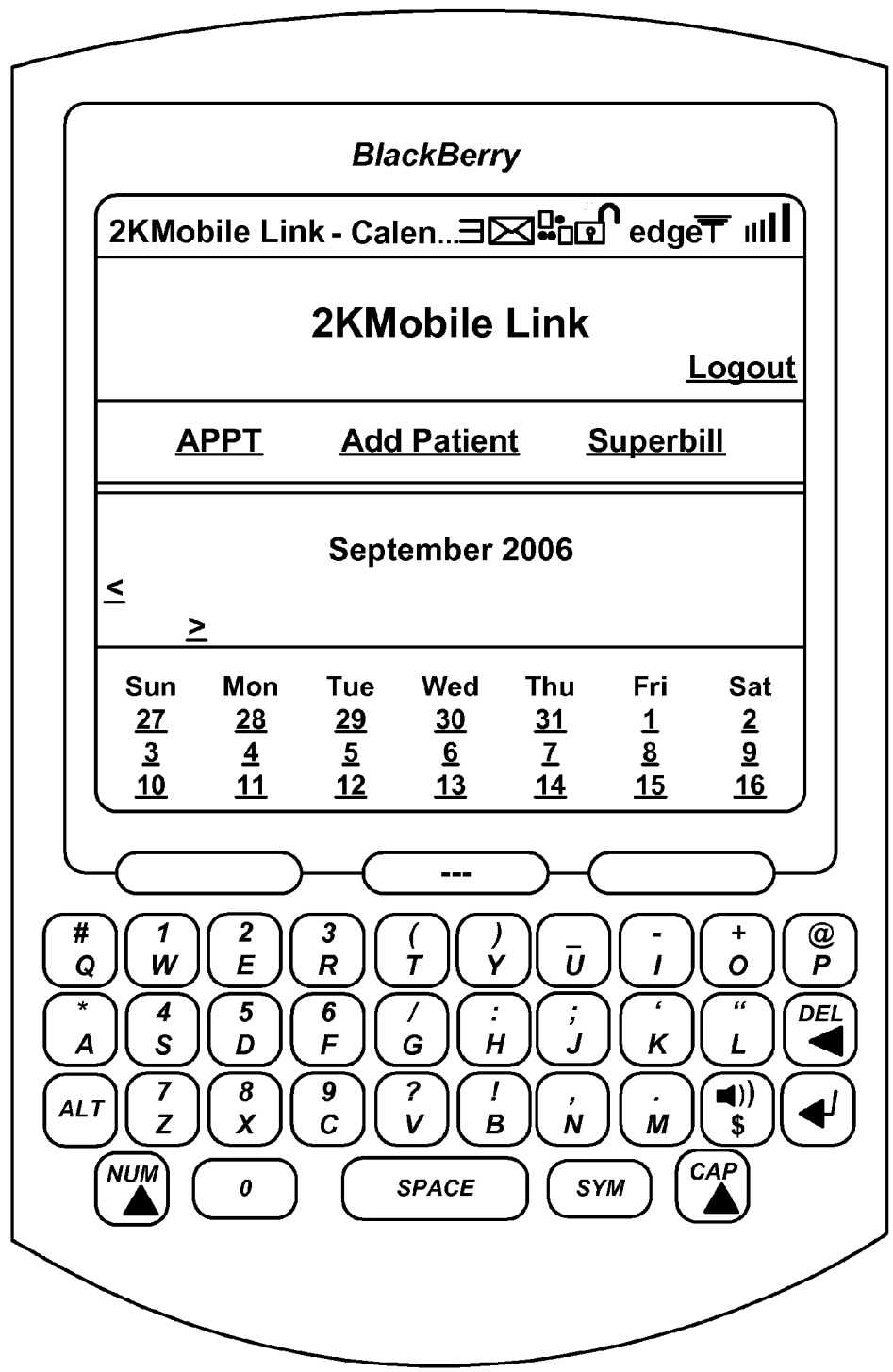
FIG. 6 shows an example of the first portion of a mobile device calendar screen presented to a user by Remote Access Management Systems according to a preferred embodiment of the present invention.
Figure 7:
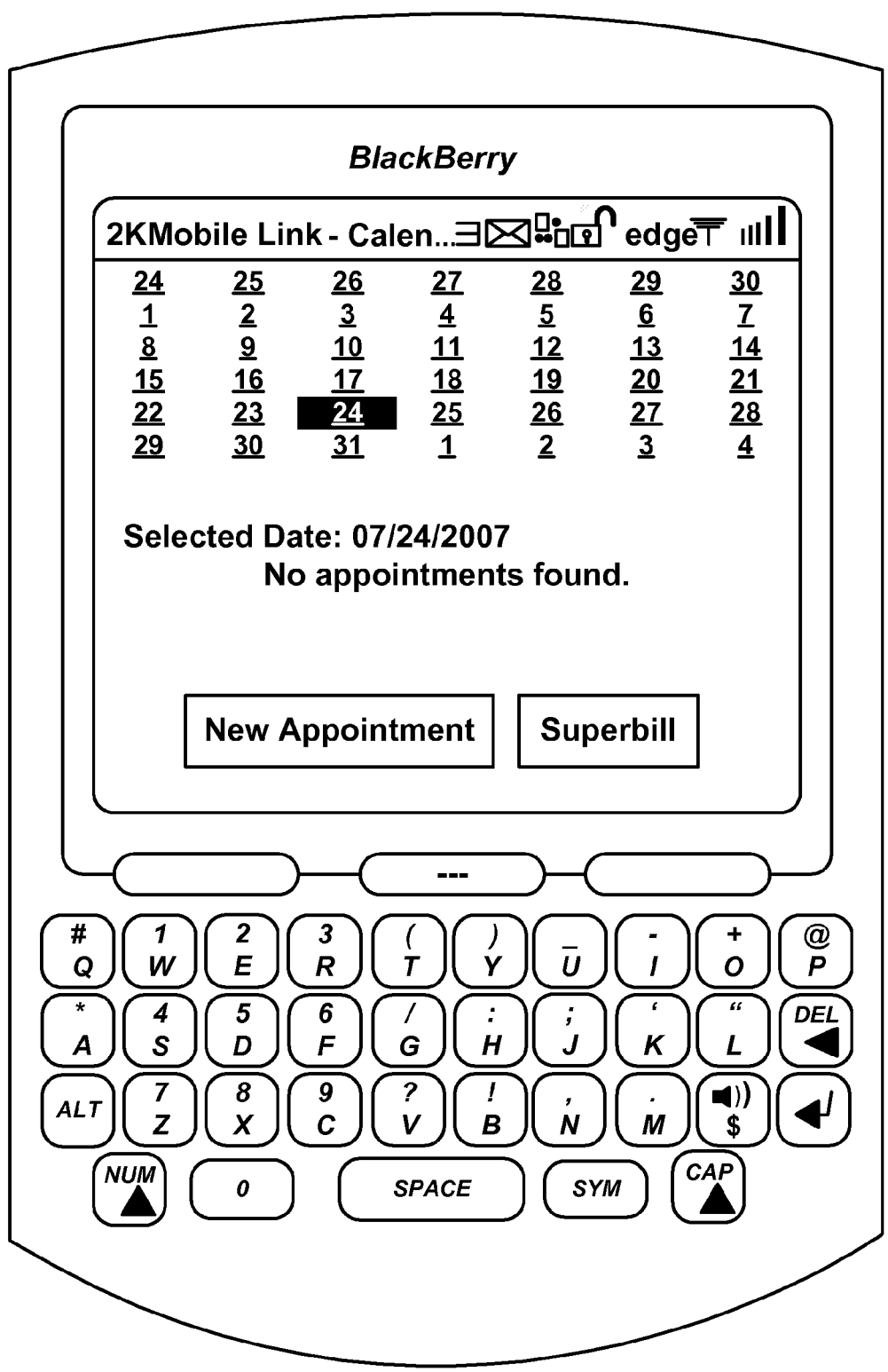
FIG. 7 shows an example of the second portion of a mobile device calendar screen presented to a user by Remote Access Management Systems according to a preferred embodiment of the present invention.

Preferably, Practitioner A 271 may access the medical practice management system implemented within Practice 1 Data Center 221 by first using Cell Phone 201, which is WAP-enabled through use of wireless markup language (WML) to utilize Internet 211 through Carrier WAP Gateway 207, to navigate to a remote-access URL associated with Medical Practice 1 503 (at least herein embodying such at least one web-browser-enabled mobile device comprises at least one wireless-access-protocol-enabled cellular-based device). Preferably, each authorized user (such as Practitioner A 271, Practitioner B 273 or Practitioner C 275) has been established and associated with Medical Practice 1 503 by a System Operator. Preferably, navigation to the remote-access URL by Practitioner A 271 invokes the login process for Medical Practice 1 503 which first determines the device type (Cell Phone 201, PDA 203, laptop 205, etc.) from which the login request originated and then presents a properly formatted login screen for the determined originating device type (at least herein embodying enabling detecting, by such at least one web-browser-based communications software system, at least one device type relating to such at least one input/output device used by such at least one user to send such at least one function request; and at least herein embodying enabling determining, by such at least one web-browser-based communications software system, at least one user interface format compatible with such detected at least one device type). Preferably, navigation to the remote-access URL activates the login module within Access Manager 451 which verifies authorization for Practitioner A 271 to view and/or update medical practice management information for Medical Practice 1 503, completes the verification, and re-directs the browser in use by Practitioner A 271 to a secondary URL associated specifically with Practice Management System Interface Module 453 implemented within Practice 1 Data Center 221 for Medical Practice 1 503. Preferably, on receipt of the notification of successful login relating to Practitioner A 271 Practice Management System Interface Module 453 completes login to the medical practice management system and receives the information and links to be displayed for mobile device calendar screen (as shown in FIG. 6 and FIG. 7). Preferably, Practice Management System Interface Module 453 re-formats the information and links to be displayed for the type of remote device (Cell Phone 201, PDA 203 or Laptop 205) from which the remote-access login request originated (at least herein embodying enabling display, by such at least one web-browser-based communications software system, of such results of such at least one function request using such determined at least one user interface format compatible with such at least one input/output device). Preferably, Practitioner A 271 may then use Cell Phone 201 to use the available functions for medical practice management system as described with respect to FIG. 5 through FIG. 47 (at least herein embodying enabling input, by such at least one user, of such at least one function request using such determined at least one user interface format compatible with such at least one input/output device). Preferably, all function requests originating from Cell Phone 201 are managed by Practice Management System Interface Module 453 as described with respect to FIG. 4A.

Upon reading the teachings of this specification, those with ordinary skill in the art will now understand that, under appropriate circumstances, considering such issues as advances in technology, competitive considerations, customer preferences, user location, etc., future browser enablement methods for portable devices, may suffice.

Referring to FIG. 4A, which shows a simplified schematic illustration of the preferred primary computer-related operations associated with use of the Remote Access Management System according to a preferred embodiment of the present invention, in Communications Method 400 preferably remote access by Practitioner A 271 utilizing cell phone 201 (representative of Practitioner B 273 utilizing PDA 203 and Practitioner C 275 utilizing Laptop 205), begins by logging in to Access Manager 451 as shown in step Remote User Login 401. Preferably, Access Manager 451 operating on Access Manager Server 209 of Access Manager Web Site 225, first completes authentication of the remote user by determining that Practitioner A 271 is an authorized user and the medical practice with which the user is associated based on information previously stored in Access Manager Database 211. Preferably, in step Authorization 405, Access Manager 451 then determines which functions Practitioner A 271 is authorized to request and responds to cell phone 201 that the login attempt was successful (or not successful as appropriate) (at least herein embodying permitting access to such web-browser-based communications software system by such at least one user). Preferably, Practitioner A 271 may then create and transmit any of a variety of function requests as shown in step Send Function Request 409 (at least herein embodying enabling receiving, by such at least one web-browser-based communications software system, at least one function request relating to such identified at least one medical practice management system from at least one input/output device operated by such at least one user). (Examples of the types of function requests and related activities are further described below with reference to FIG. 6 through FIG. 47.)

Preferably, Access Manager 451 receives the transmitted function request and redirects the request to a URL associated with Practice 1 Data Center 221 (representative of Practice 2 Data Center 223 and any number of similar practice data centers) stored in Access Manager Database 211. Preferably, the function request is then received by Practice Management System Interface Module 453, and, as shown in step Format/Send Information Request to Medical Practice Management System 409, the information request is formatted properly and transmitted to medical practice management system for interpretation and action, as shown in step Respond to Information Request by Medical Practice Management System 411 (at least herein embodying communicatively coupling such at least one web-browser-based communications software system to such identified at least one medical practice management system; and at least herein embodying enabling transmitting, by such at least one web-browser-based communications software system, such at least one function request to such identified at least one medical practice management system; and at least embodying herein wherein such at least one medical practice support computer system generates at least one result). The medical practice management system will complete the requested action and transmit the generated results to Practice Interface Management System Module 453 as shown in step Receive Response from Medical Practice Management System 413 (at least herein embodying enabling receiving, by such at least one web-browser-based communications software system, results of such at least one function request from such identified at least one medical practice management system; and at least embodying herein wherein such at least one result is received by such at least one web-browser-based communications computer software system). Preferably, in step Format Results 415 the results are formatted properly for display on cell phone 201 and then in step Send Formatted Results 417 the results are transmitted to Cell Phone 201. In turn, Cell Phone 201 will then receive and display the formatted results on Cell Phone 201 as shown in step Receive/Display Results 419 (at least herein embodying enabling transmitting such results of such at least one function request to such at least one input/output device operated by such at least one user).

As can be seen, this approach preferably permits Software Provider 250 to manage and control remote access to Practice 1 Data Center thereby significantly improving a system operator's ability to enforce licensing and subscription provisions. Additionally, this approach permits Software Provider 250 to develop a standardized method of operation for Practitioner A 271 utilizing cell phone 201 (representative of Practitioner B 273, Practitioner C 275 or any number of other practitioners) regardless of the practice management systems used by the practice. Finally, Software Provider 250 may deliver remote access solutions for a variety of practice management systems by making the necessary adjustments to the XML interface within the Practice Management System Interface Module.

Figure 4B:
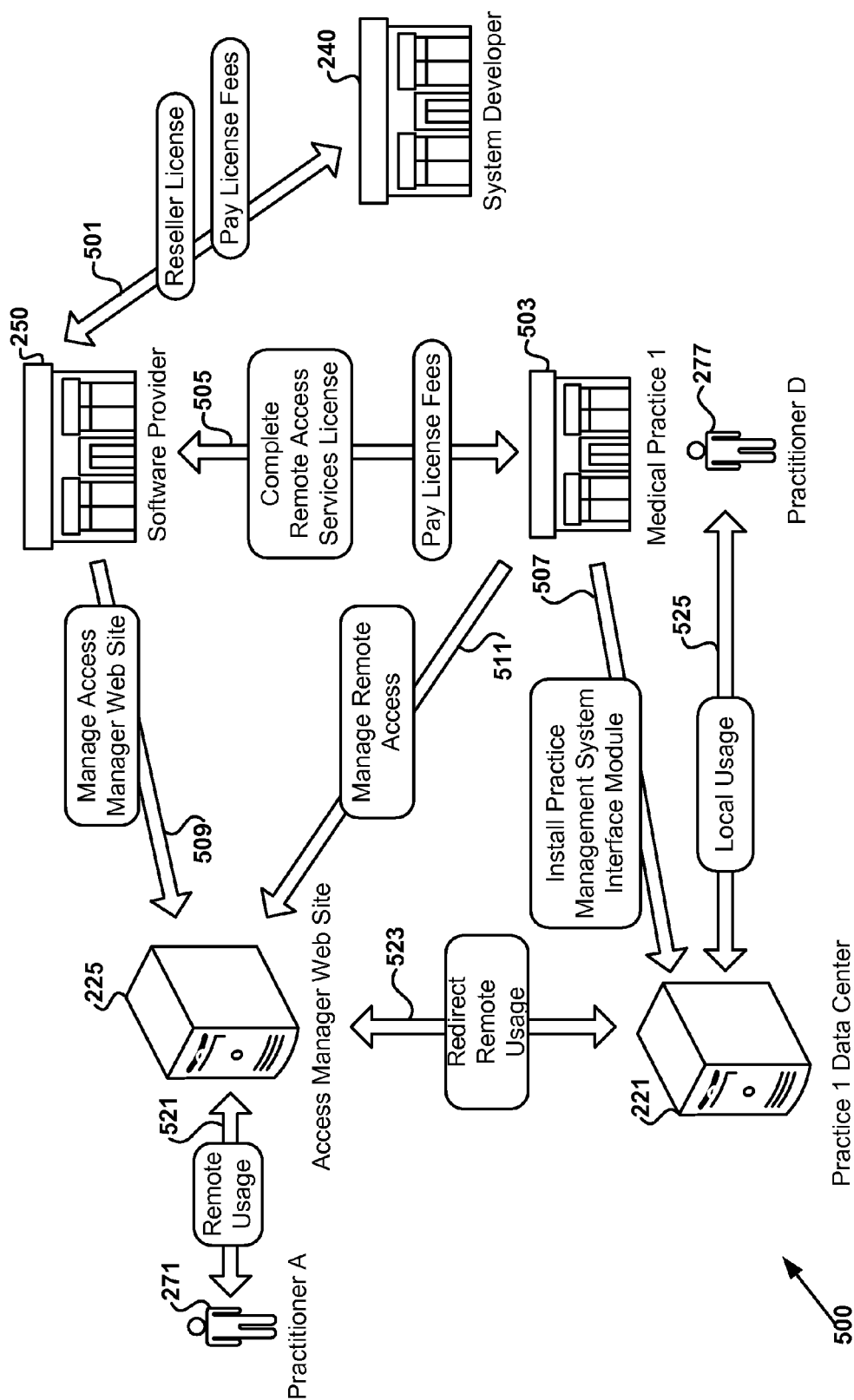
FIG. 4B shows a simplified schematic illustration of the preferred business method relating to the licensing, implementation and use of the Remote Access Management System according to a preferred embodiment of the present invention.

Referring to FIG. 4B, which shows a simplified schematic illustration of the preferred business method relating to the licensing, implementation and use of Remote Access Management System according to a preferred embodiment of the present invention, preferably Remote Access Management Business Method 500 comprises software and business processes.

Preferably, System Developer 240 may offer a reseller license to Software Provider 250 in return for payment of an agreed reseller licensing fee as depicted in Reseller Licensing Process 501. Preferably, the license between System Developer 240 and Software Provider 250 will permit Software Provider 250 to offer Remote Access Management System 200 Medical Practice 1 503 to Medical Practice 1 503 in return for payment of a mutually agreed license fee by Software Provider 250 to System Developer 240.

Preferably, as shown in License Process 505, Software Provider 250 offers Remote Access Management System services to Medical Practice 1 503 to quickly and easily provide Practitioner A 271 secure, remote access to the Practice Management System operated by Medical Practice 503 (at least herein embodying offering at least one web-browser-based communications software system to at least one first user of such plurality of users; and at least herein embodying assisting identifying at least one medical practice management system of such plurality of medical practice management systems). Upon agreement between Software Provider 250 and Medical Practice 1 503, a Remote Access Services License is completed under which Software Provider 250 will permit Practitioner A 271 (and others as authorized by Medical Practice 1 503) remote access via Cell Phone 201 (or any other web-browser-enabled device capable of accessing the Internet) and in return Medical Practice 1 503 agrees to pay an agreed License Fee to System Operator. Preferably, as shown in Local Usage Process 525 local users, such as Practitioner D 277, will access the Practice Management System in the typical manner provided by the particular Practice Management System provider. Local operation and usage are preferably not affected by implementation of Remote Access Management System 200.

Preferably, as shown in Install Practice Management System Interface Module 507 Software Provider 250 provides the necessary program modules and set up and operating instructions for implementation of the Practice Management System Interface Module 453 at Practice 1 Data Center 221. Preferably, Medical Practice 1 503 will complete implementation of Practice Management System Interface Module 453. Preferably, Practice Management System Interface Module 453 provides the necessary interface and formatting and re-formatting functions to facilitate remote access by a variety of web-browser-enabled or WAP-enabled devices. Preferably, Practice Management System Interface Module 453 operates in conjunction with Access Manager 451 to control and provide remote access to the medical practice management system used by Medical Practice 1 503.

Preferably, as shown in Manage Access Manager Web Site Process 509, Software Provider 250 will authorize Medical Practice 1 503 to use Access Manager Web Site 225 to set up users, their related privileges and other operational parameters to control and manage remote access to the Practice Management System for Medical Practice 1 503.

Preferably, after System Operator has established Medical Practice 1 503 as a licensed organization authorized users can be set up on behalf of Medical Practice 1 503 as depicted by Manage Remote Access Process 511. Examples of other functions that may preferably be performed on behalf of Medical Practice 1 503 include selectively enabling or disabling the following functions:

Ability to add, delete, or edit patient files,
Ability to add, delete, or edit diagnosis codes,
Ability to add, delete, or edit CPT codes,
Ability to add, delete, or edit appointments,
Ability to add, delete, or edit superbills,
Ability to automatically check bill to patient and insurance companies (some clients want it already checked and some do not want it checked),
Ability to automatically post charge amounts from fee schedule or post $0 and let the customer enter it later, and
Ability to enable or disable viewing multiple providers' schedules.

Preferably, after completion of the above described processes, Practitioner A 271 may login and complete a variety of real-time interactions with the Practice Management System operated on behalf of Medical Practice 1 503, as shown by Remote Usage Process 521. Preferably, functions that Practitioner A 271 may perform include:

View, Add and Edit Patients,
View, Add and Edit Appointments,
View, Add and Edit Superbill,
Add a CPT to an existing Superbill,
Search, Add and Edit CPT Codes, and
Search, Add and Edit Diagnosis Code.

Preferably, all remote interactions by Practitioner A 271 with the Practice Management System are redirected from Access Manager Web Site 225 to Practice 1 Data Center 221 as depicted by Redirect Remote Usage Process 523. Preferably, all remote interactions are accepted and managed by Practice Management System Interface Module 453 which receives the request, prepares and sends the appropriate XML-based request to the Practice Management System, receives the appropriate response and then formats the output for the type of remote device (laptop, cell phone or PDA, etc.) used by Practitioner A 271 and sends it back to the remote device being used by Practitioner A 271.

Upon reading the teachings of this specification, those with ordinary skill in the art will now understand that, under appropriate circumstances, considering such issues as competition, favorable marketing conditions, advances in technology, user preference, user location, etc., other licensing and operational arrangements, such as operation and management of Remote Access Management System by system developer, providing, by system developer, hosting services for operation of Remote Access Management System to system operator, etc., may suffice.

Figure 5:
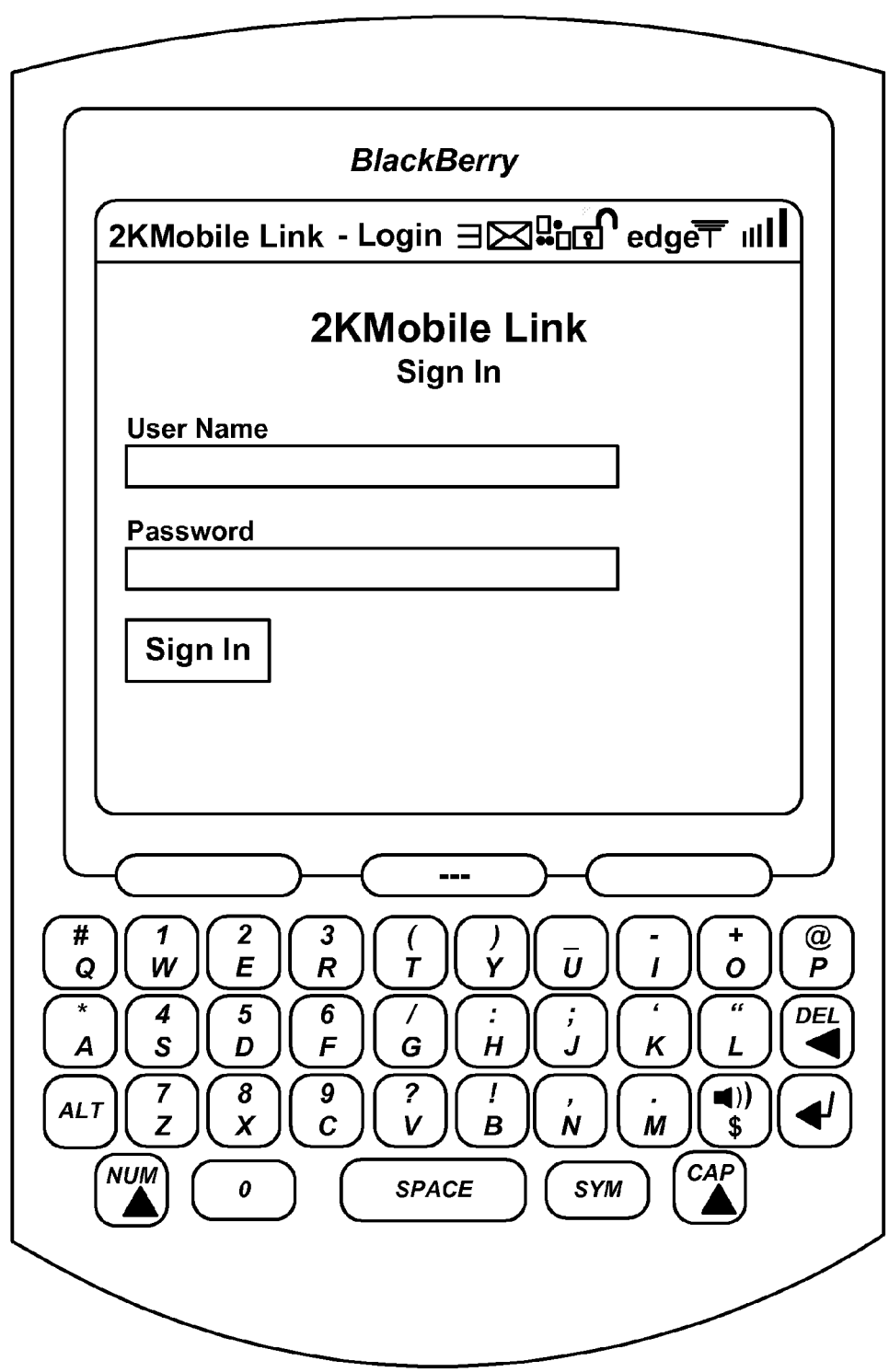
FIG. 5 shows an example mobile device login screen for accessing Remote Access Management Systems according to a preferred embodiment of the present invention.

Referring to FIG. 5, which shows an example mobile device login screen for accessing Remote Access Management Systems according to a preferred embodiment of the present invention, preferably Practitioner A 271 clicks on the browser icon on the menu of a Blackberry (or similar cellular device with cellular-based connectivity to the Internet 211 or PDA or laptop capable of connecting to Internet 211) and selects the Go To option in browser options and enters a URL (e.g., www.2 kmedical.com), which preferably presents the Login screen to Practitioner A 271, as shown. After successful login (as described with respect to FIG. 3 and FIG. 4), the Calendar page (Refer to FIG. 6 and FIG. 7) is preferably shown to Practitioner A 271 which preferably contains a Menu (APPT [appointment], Add Patient and Superbill links, as shown), a Calendar and a Providers (not shown) dropdown list. Preferably, the information provided on the Calendar Page is retrieved from medical practice management system related to Practitioner A 271. Preferably, by default, the current day's date is selected in the Calendar, and the name of Practitioner A 271 is selected and appointments for today's date are displayed (see FIG. 8).

Figure 8:
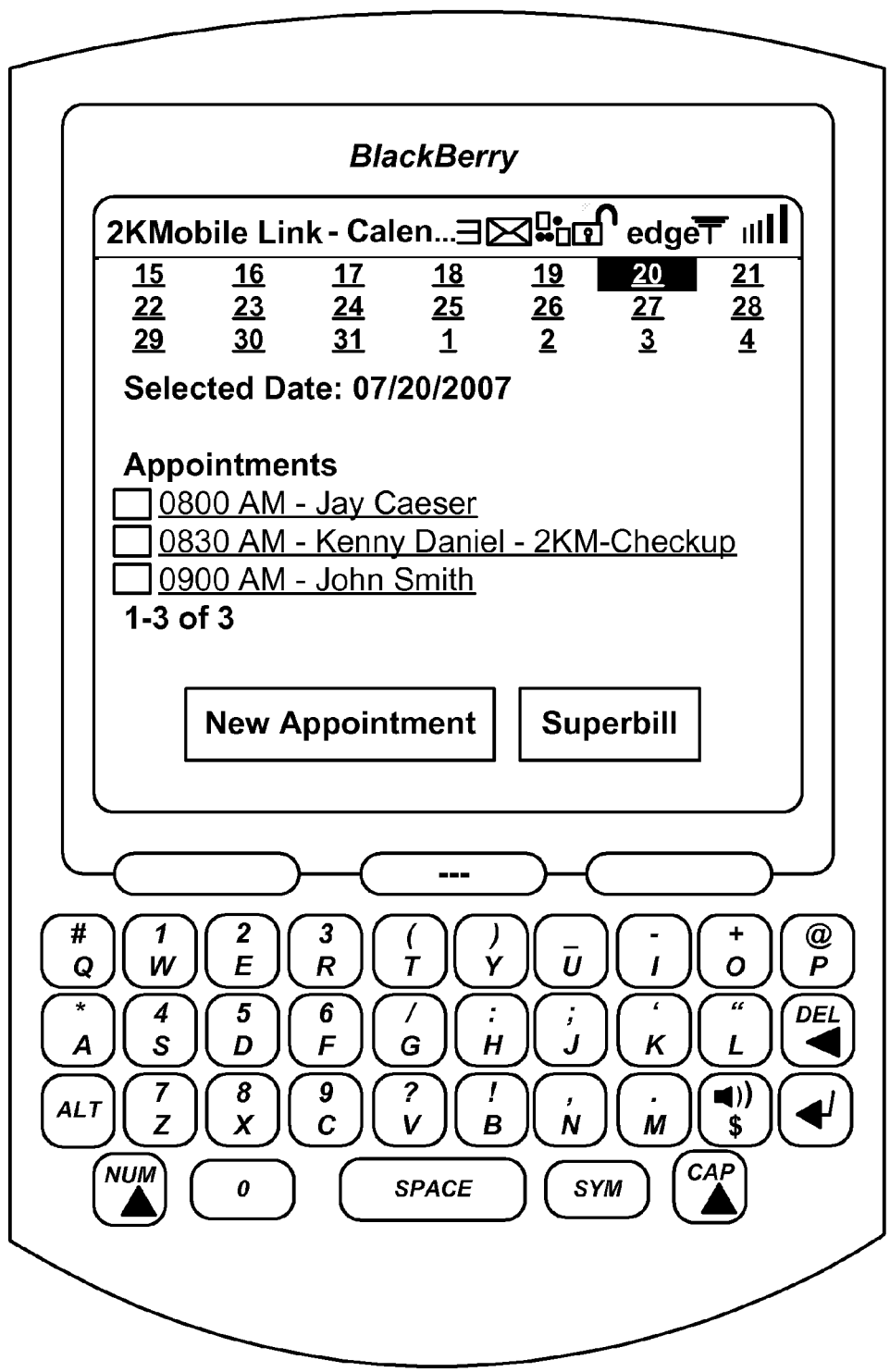
FIG. 8 shows an example mobile device appointments screen presented to a user by Remote Access Management Systems according to a preferred embodiment of the present invention.

Preferably, selecting a date on the Calendar presents the appointments for that date to Practitioner A 271 (as shown in FIG. 8). Preferably, the appointments of other providers for a date may be presented by selecting a provider from the Providers dropdown and clicking on Get button (not shown).

Preferably, the Menu (APPT [Appointment], Add Patient and Superbill links) is common for all the screens. Preferably, clicking on the APPT link presents the Calendar page, preferably clicking on the Add Patient link presents the Add Patient screen, and preferably clicking on the Superbill link presents the Search Patient page to Practitioner A 271 to search for a patient and view the selected patient's Superbill.

Figure 9:
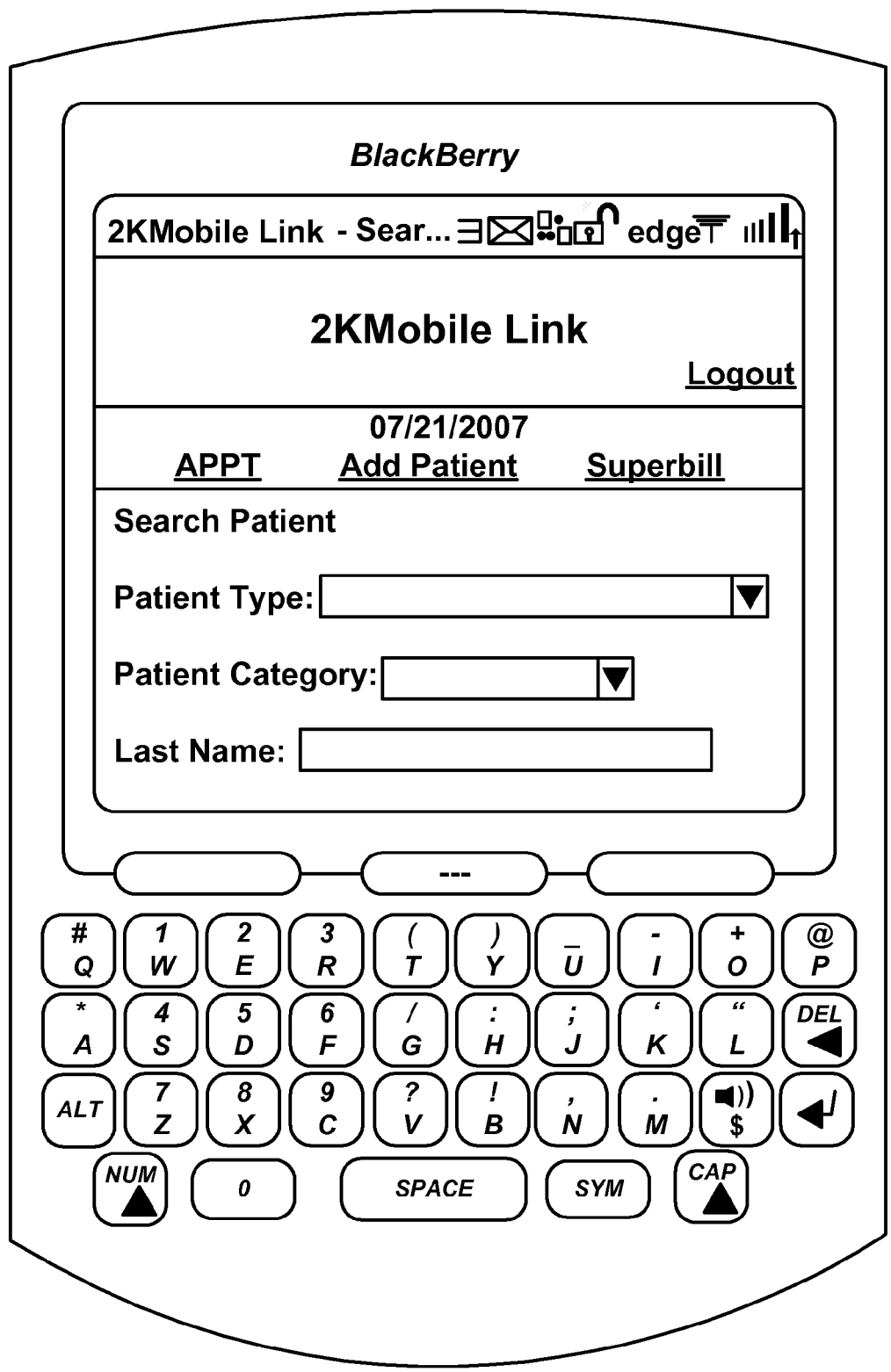
FIG. 9 shows an example of the upper portion of a mobile device patient search screen presented to a user by Remote Access Management Systems according to a preferred embodiment of the present invention.
Figure 10:
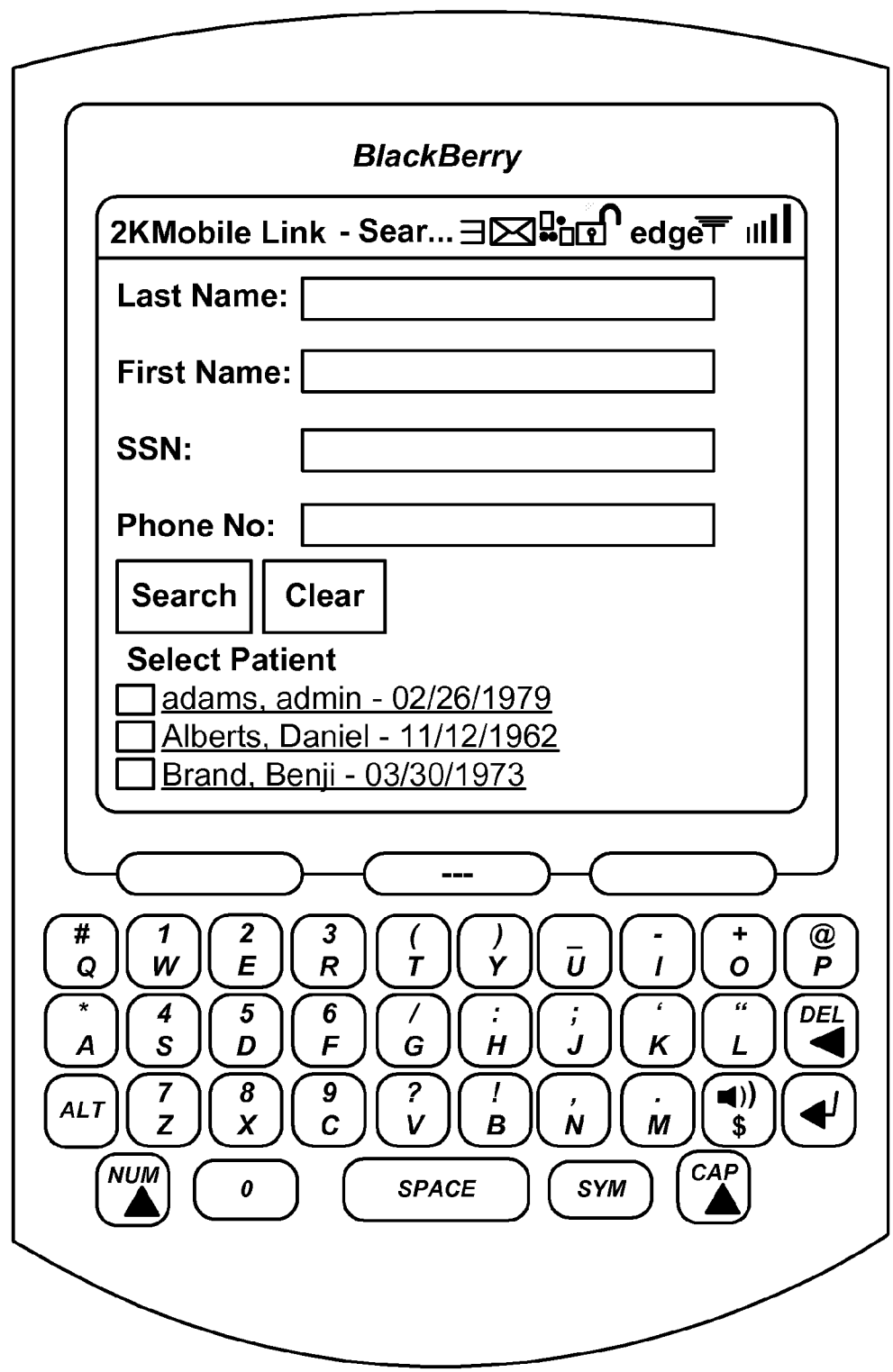
FIG. 10 shows an example of the middle portion of a mobile device patient search screen showing search results presented to a user by Remote Access Management Systems according to a preferred embodiment of the present invention.
Figure 11:
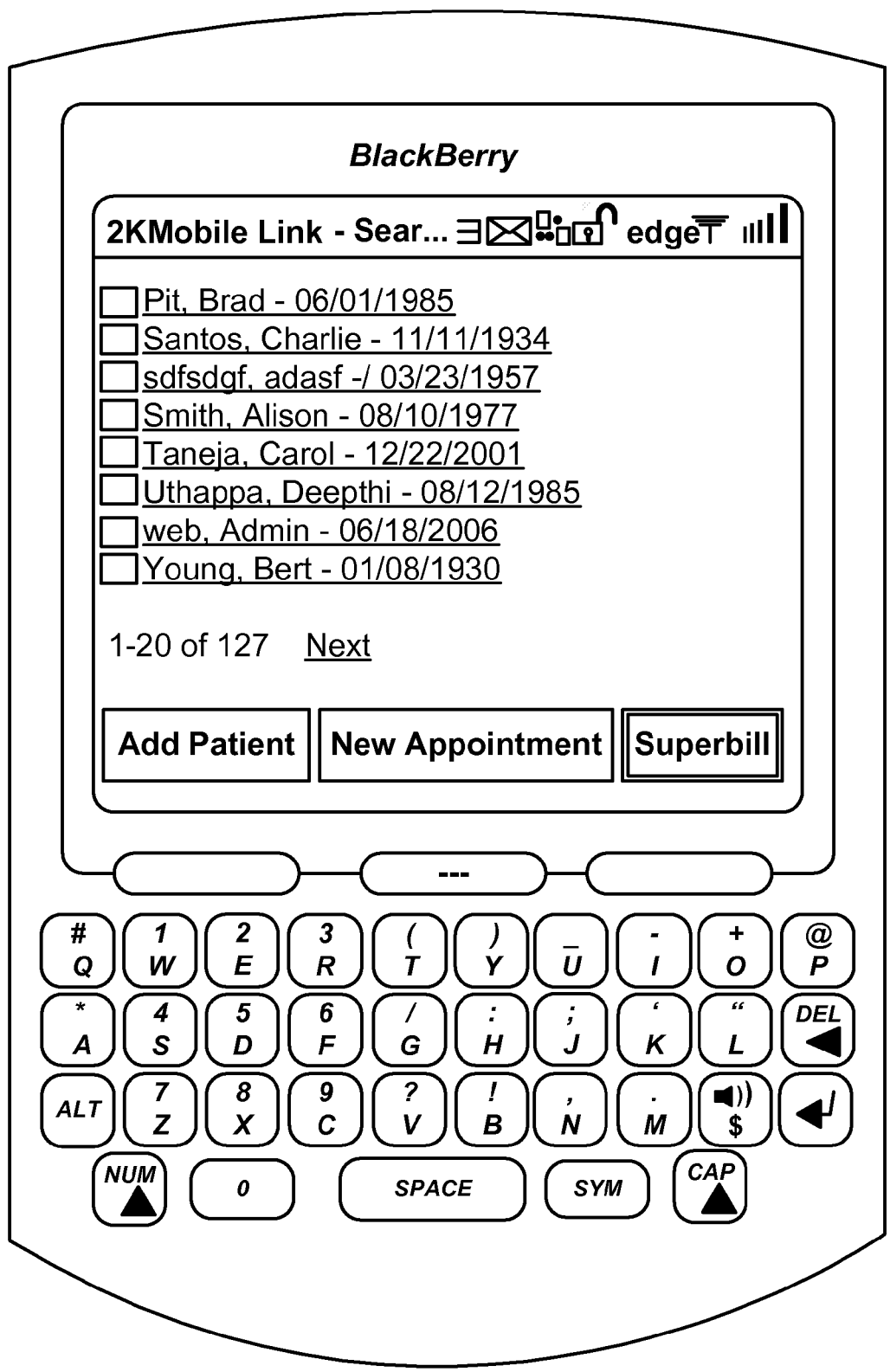
FIG. 11 shows an example of the lower portion of a mobile device patient search screen showing search results presented to a user by Remote Access Management System according to a preferred embodiment of the present invention.
Figure 12:
FIG. 12 shows an example of the upper portion of a mobile device patient add screen presented to a user by Remote Access Management Systems according to a preferred embodiment of the present invention.
Figure 13:
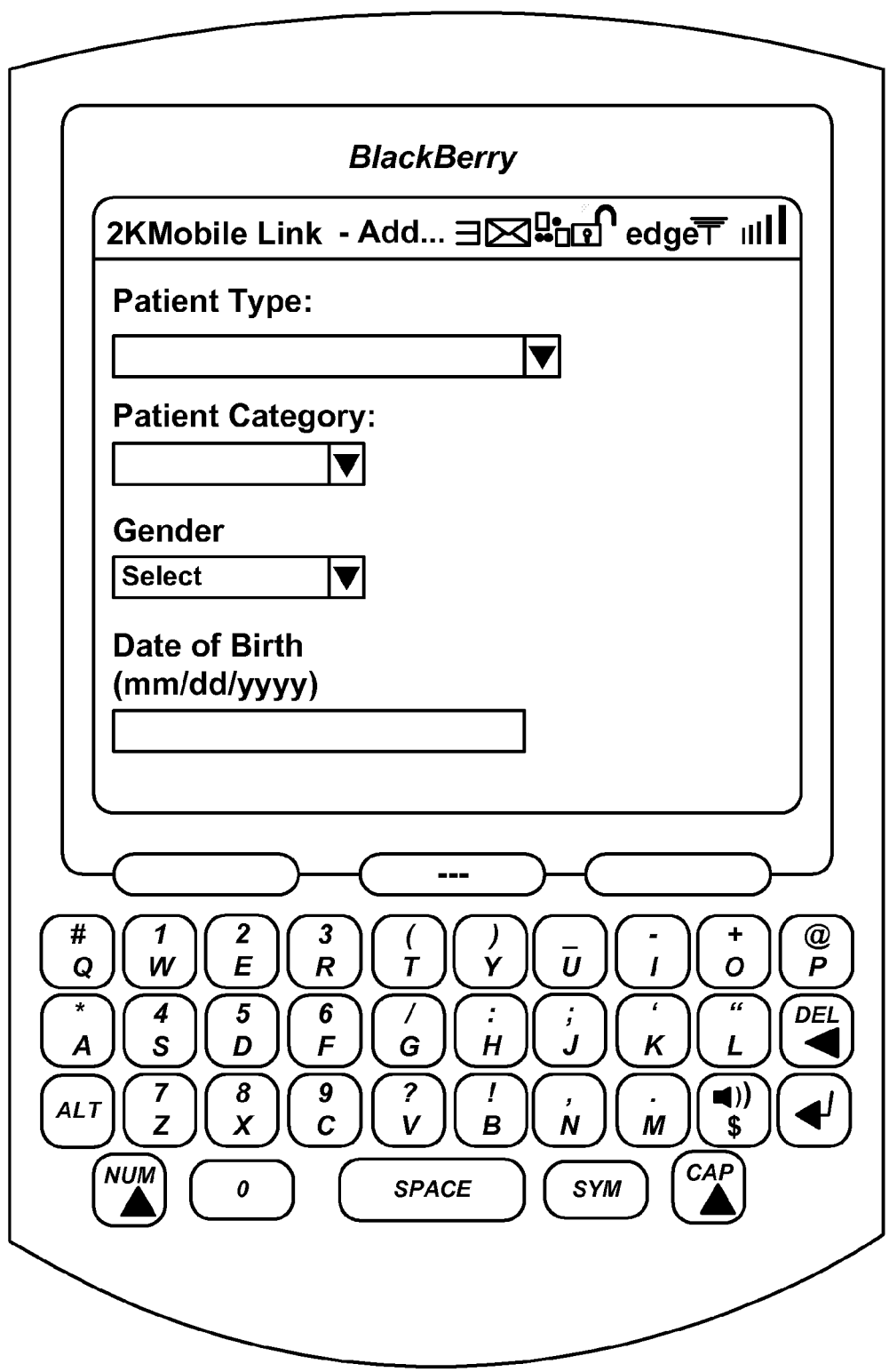
FIG. 13 shows an example of the middle portion of a mobile device patient add screen presented to a user by Remote Access Management Systems according to a preferred embodiment of the present invention.
Figure 14:
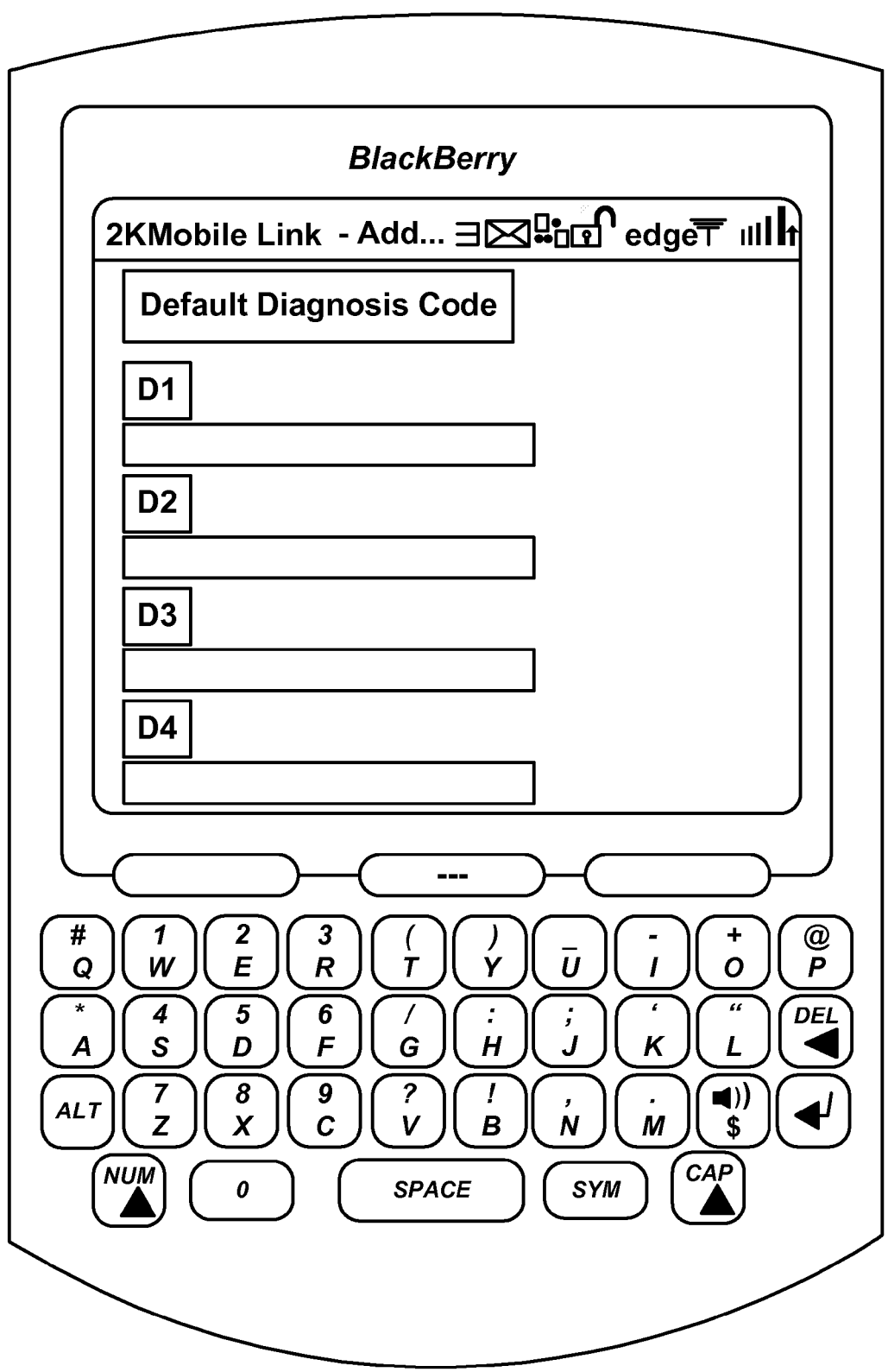
FIG. 14 shows an example of the lower portion of a mobile device patient add screen presented to a user by Remote Access Management Systems according to a preferred embodiment of the present invention.

Referring to FIGS. 9, 10 and 11, which show examples of the upper and lower portions of mobile device patient search screens and search results screens presented to Practitioner A 271 by Remote Access Management Systems according to a preferred embodiment of the present invention, preferably clicking the New Appointment button on the Calendar page (Refer to FIG. 8) displays the Search Patient page. Preferably, clicking the search button presents the search result based on the search criteria given to Practitioner A 271 as shown in FIG. 10 and FIG. 11. FIGS. 9, 10, 12, and 13 show examples of patient information data (also referred to herein as patient demographic data). As shown at least in FIGS. 9, 10, 12, and 13, patient information data may include patient last name, patient middle initial, patient first name, patient gender, patient date of birth, patient social security number, patient phone number, patient type, patient category, patient chart number, etc.

Figure 15:
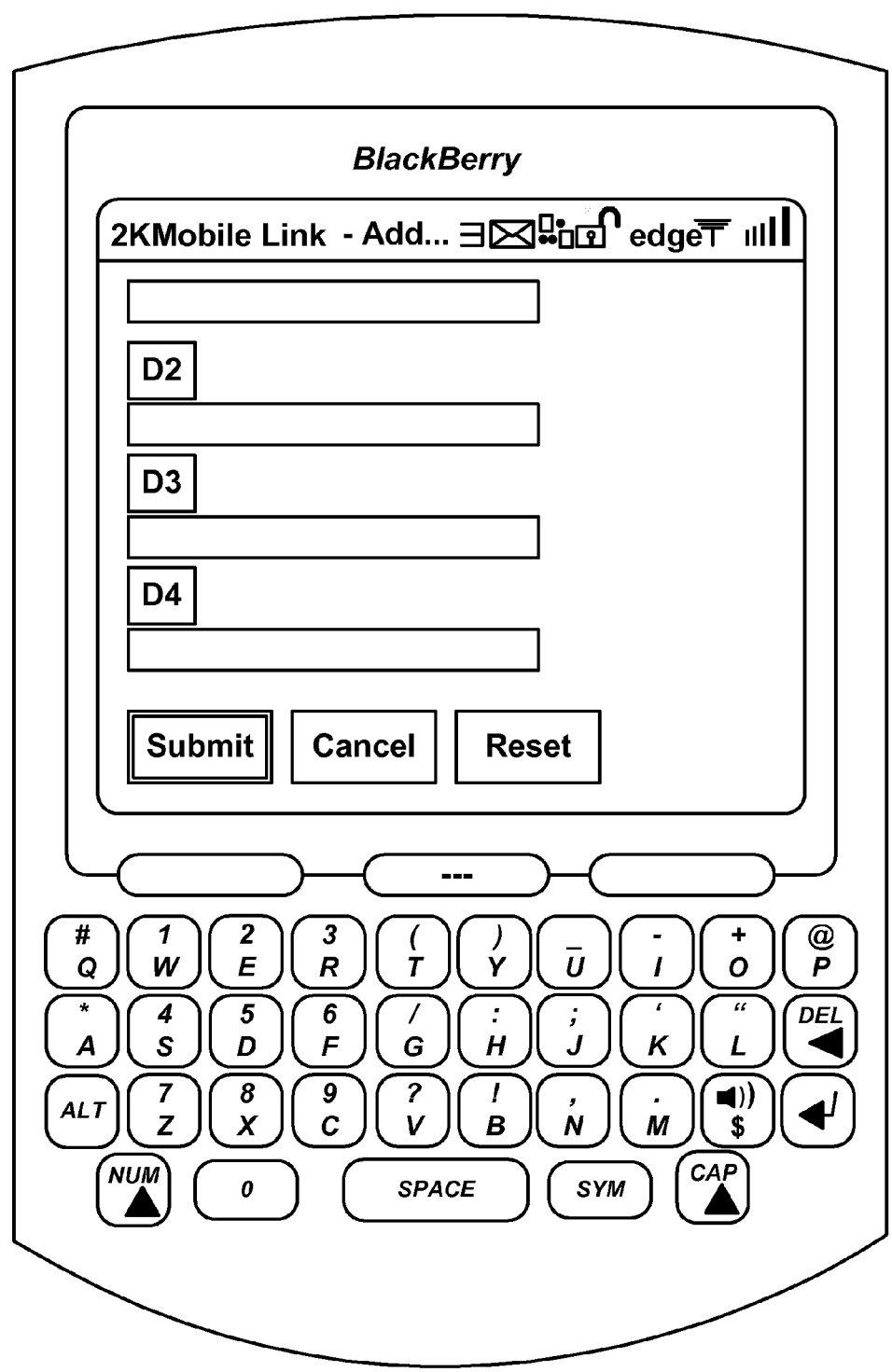
FIG. 15 shows an example of the lower portion of a mobile device patient add screen presented to a user by Remote Access Management Systems according to a preferred embodiment of the present invention.
Figure 16:
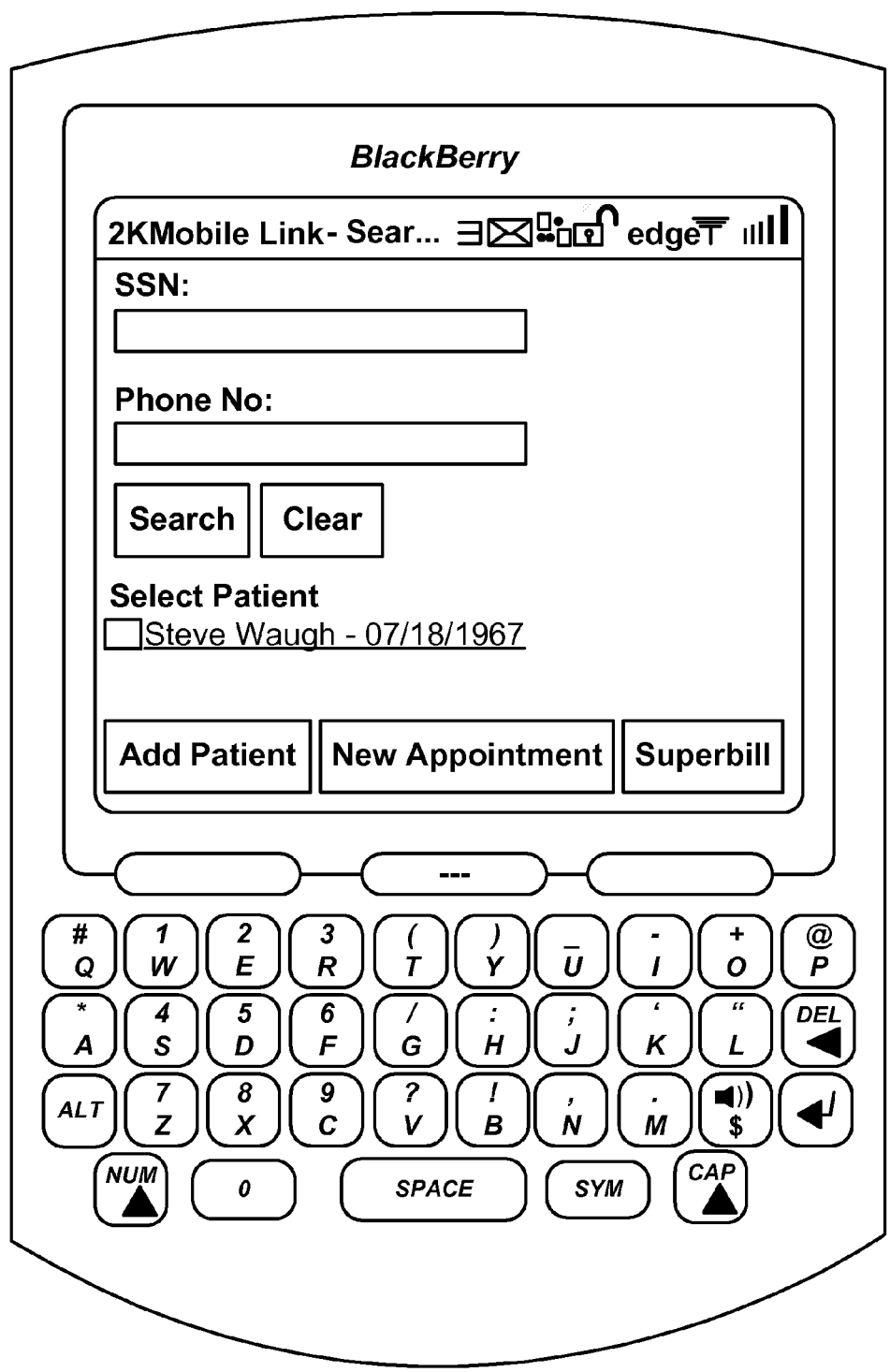
FIG. 16 shows an example of a mobile device patient search screen presented to a user by Remote Access Management Systems after completion of adding a new patient according to a preferred embodiment of the present invention.
Figure 17:
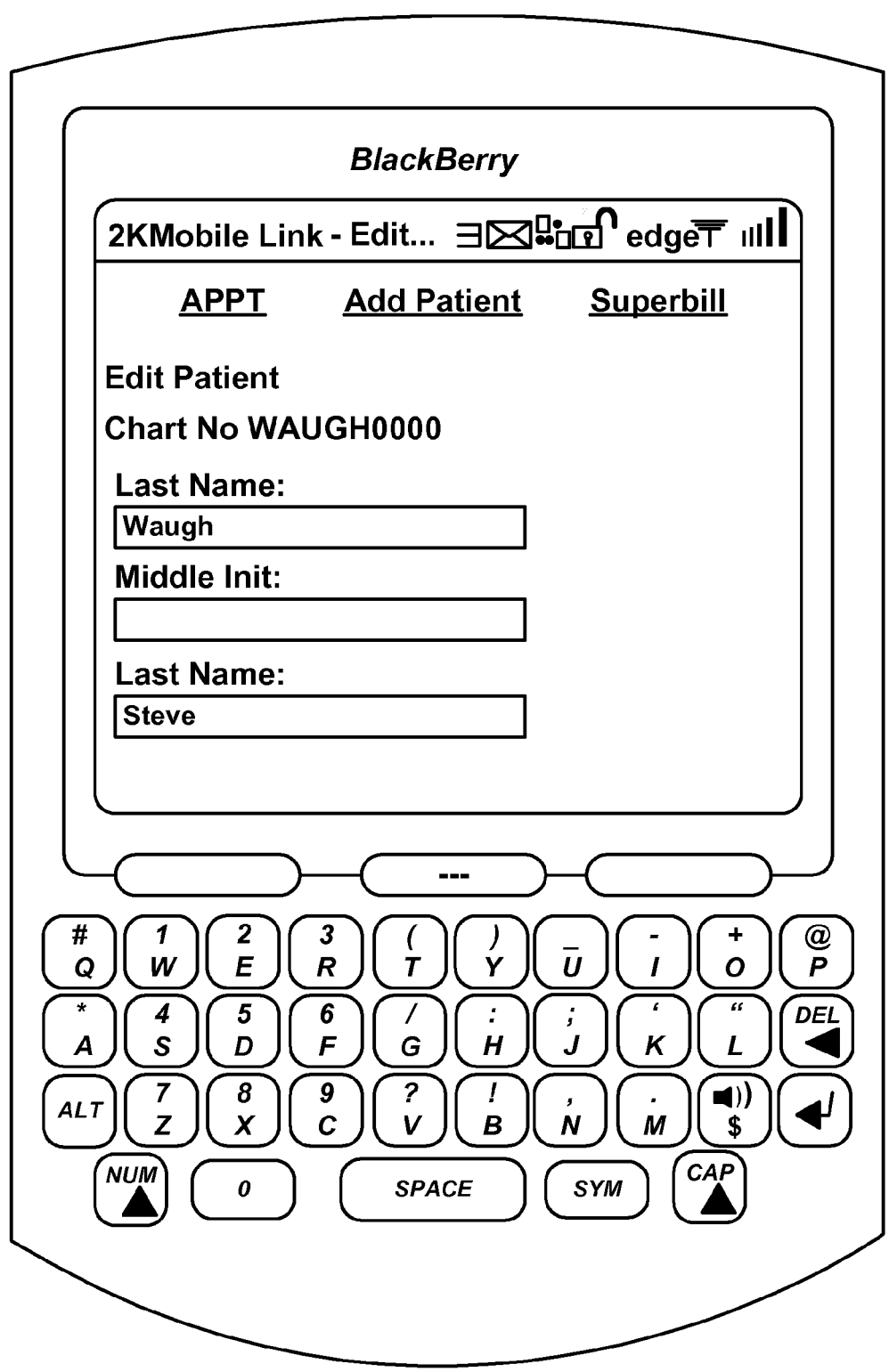
FIG. 17 shows an example of the upper portion of a mobile device patient edit screen presented to a user by Remote Access Management Systems according to a preferred embodiment of the present invention.
Figure 18:
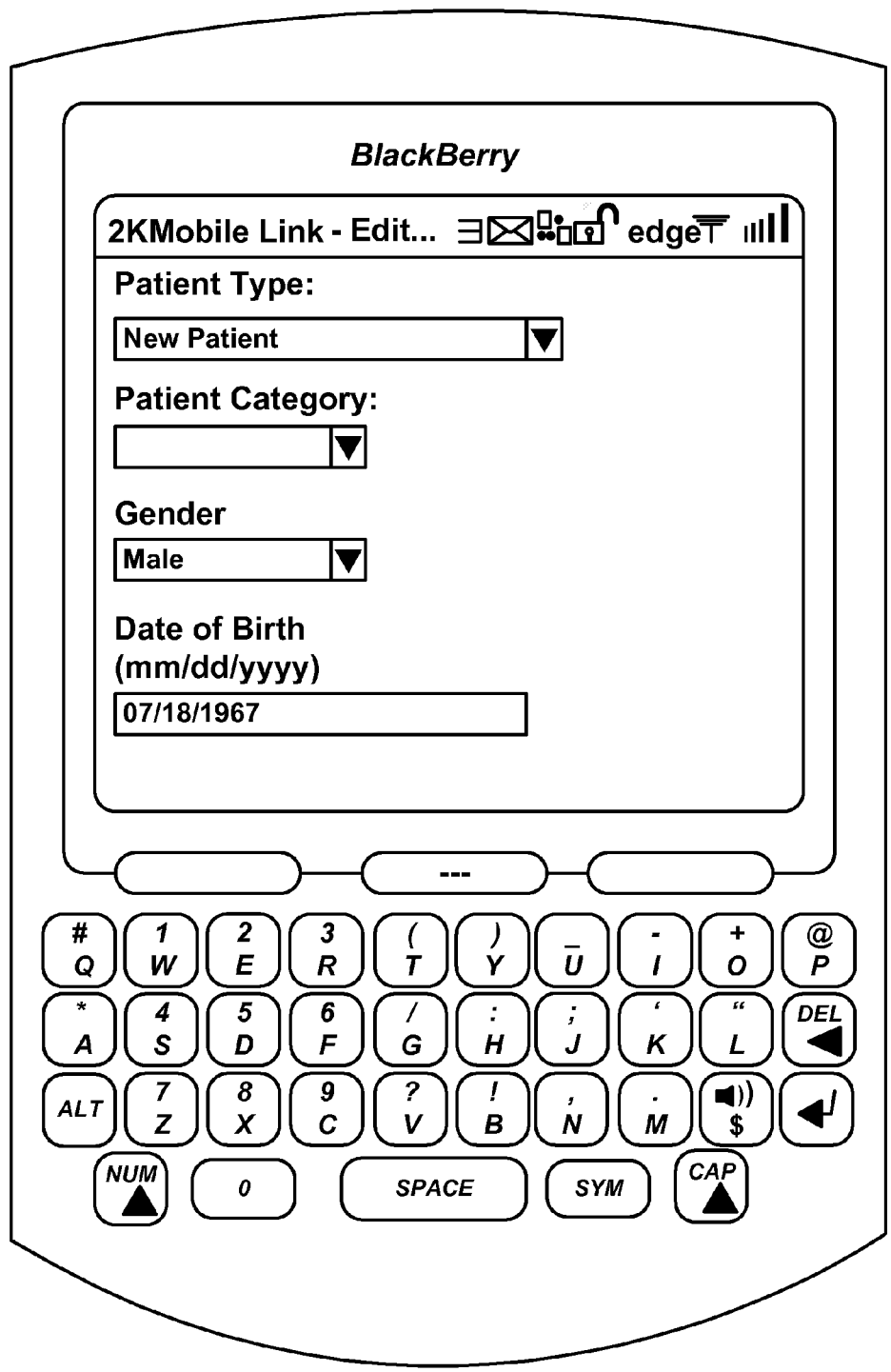
FIG. 18 shows an example of the second portion of a mobile device patient edit screen presented to a user by Remote Access Management Systems according to a preferred embodiment of the present invention.
Figure 19:
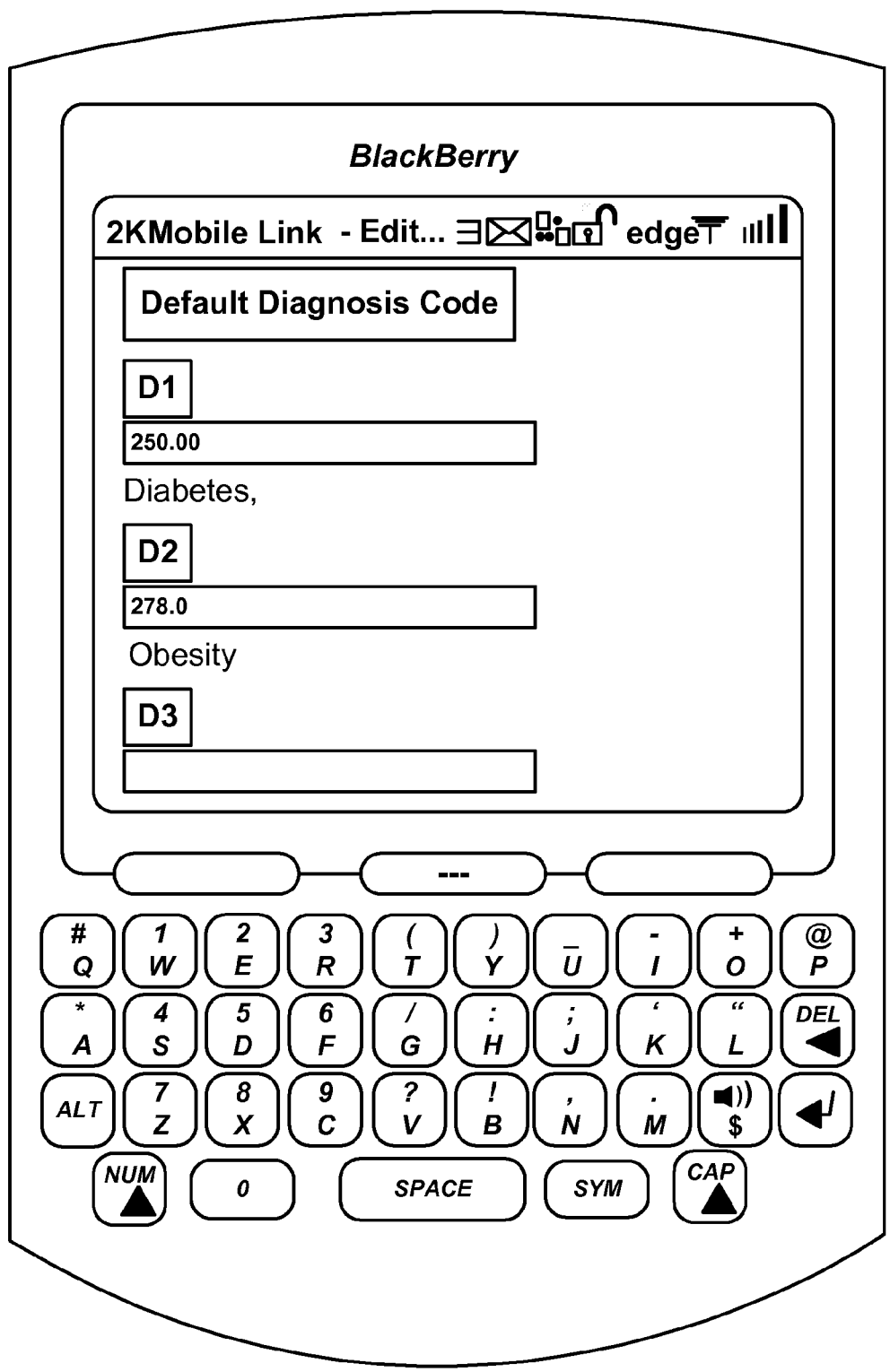
FIG. 19 shows an example of the third portion of a mobile device patient edit screen presented to a user by Remote Access Management Systems according to a preferred embodiment of the present invention.

Referring to FIGS. 12, 13, 14, 15, and 16, which show examples of the mobile device patient add screens presented to a user by Remote Access Management Systems according to a preferred embodiment of the present invention, preferably a patient can be added in the following ways:

Click on the Add Patient link on the menu (See FIG. 5);
From the Calendar page (See FIG. 6) click on the New Appointment button, which preferably presents the Search Patient page (refer to FIG. 9), once the Search Patient page is displayed click on the Add Patient button. Preferably, clicking on the Submit button, as shown in FIG. 15, saves the patient details. The Search Patient page (See FIG. 16) with the recently added patient in the search result is then displayed. Preferably, the chart number is auto generated if it is not entered.
The Diagnosis Code selected/entered are displayed in the Add Superbill section of Superbill page, if the "automatically add Diagnosis Codes from Patient to Superbill" option is selected in the Customize page.

Referring to FIG. 17, FIG. 18, FIG. 19, and FIG. 20, which show examples of mobile device patient edit screens presented to Practitioner A 271 by Remote Access Management Systems according to a preferred embodiment of the present invention, preferably clicking on the New Appointment button on the Calendar page (Refer to FIG. 6), displays the Search Patient page (as shown in FIG. 9). Preferably, clicking on the Search button, displays the search result based on the search criteria given, then clicking on any of the patient links displays the Edit Patient page (See FIG. 17) where the selected patient's details are displayed in editable textboxes.

Figure 21:
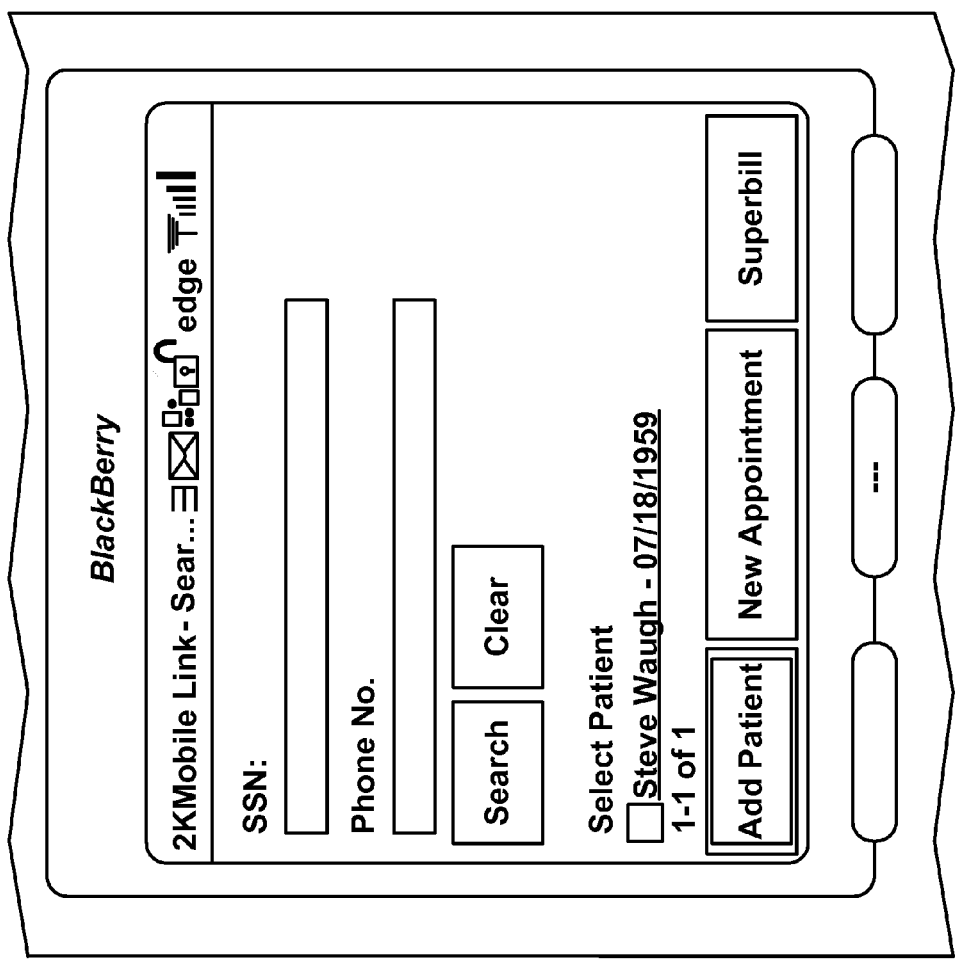
FIG. 21 shows an example of a mobile device patient search screen presented to a user by Remote Access Management Systems after completion of editing a new patient according to a preferred embodiment of the present invention.

FIG. 21 shows an example of a mobile device patient search screen presented to a user by Remote Access Management Systems after completion of editing a patient's data according to a preferred embodiment of the present invention. Preferably, clicking on the Update button updates the patient details and the Search Patient page with the updated patient in the search result is displayed, as shown.

Preferably, clicking on the Appointment button displays the Add Appointment page (See FIG. 22) where an appointment can be scheduled for that patient. Preferably, clicking on the Superbill button displays the View Superbill page (See FIG. 26) where a list of Superbills for that patient can be viewed.

Figure 20:
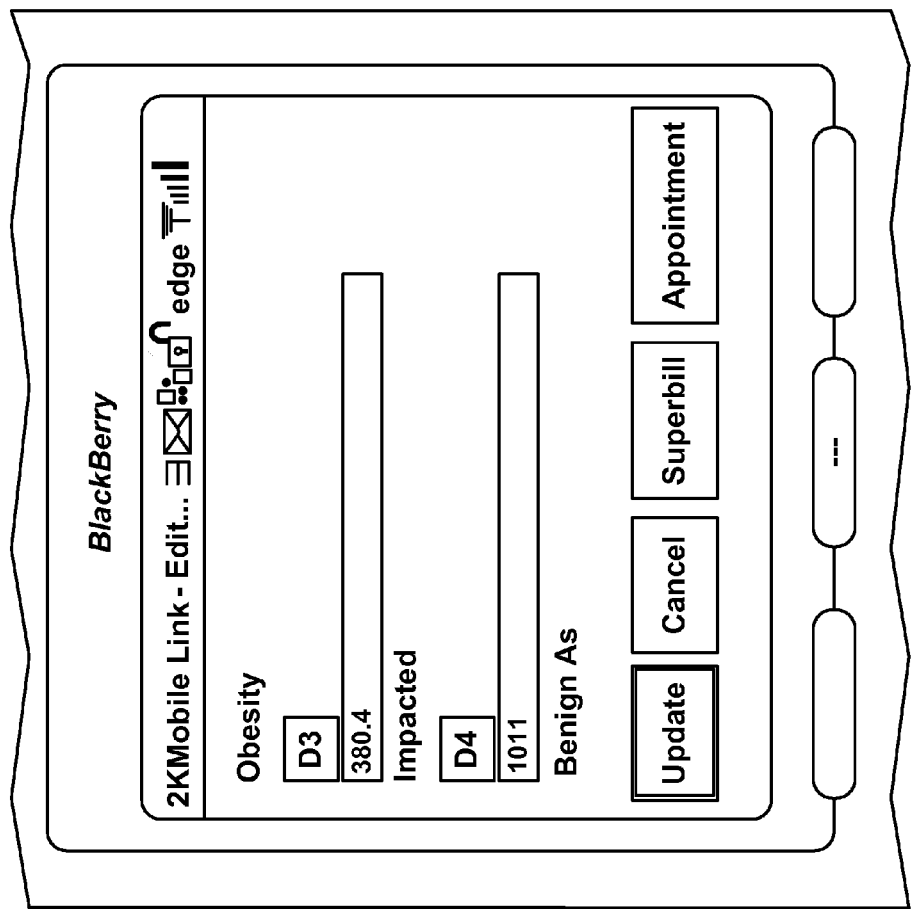
FIG. 20 shows an example of the lower portion of a mobile device patient edit screen presented to a user by Remote Access Management Systems according to a preferred embodiment of the present invention.
Figure 22:
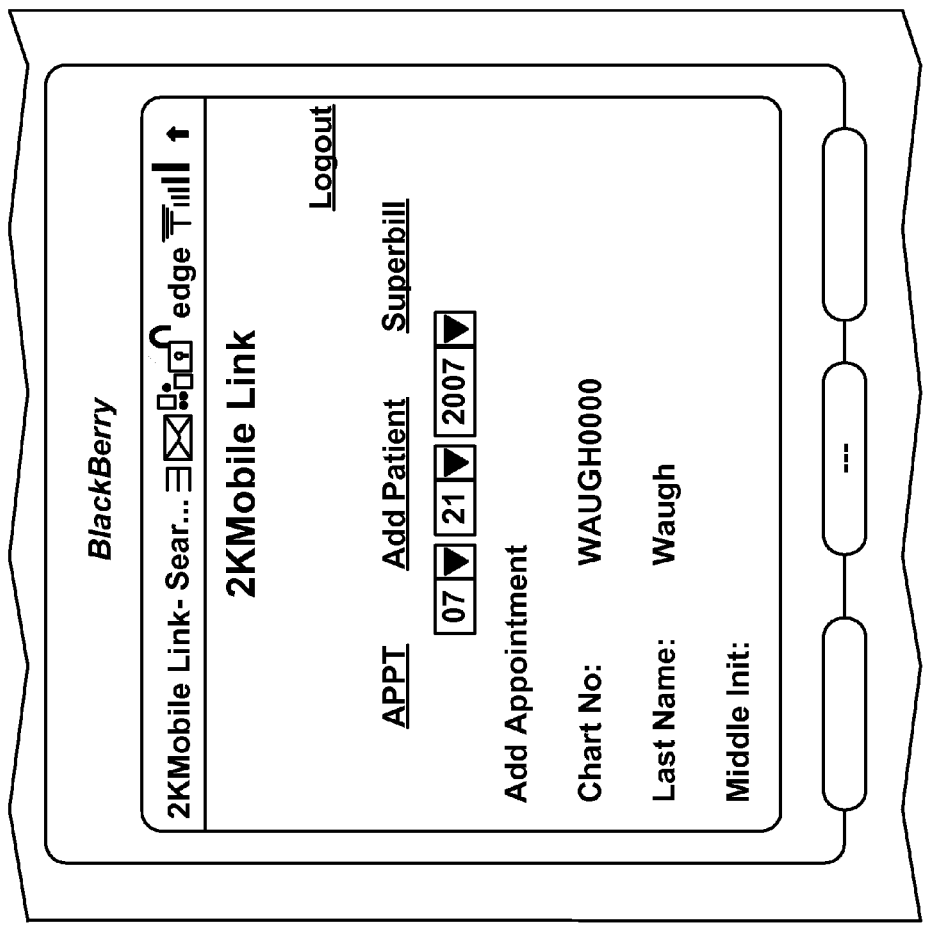
FIG. 22 shows an example of the upper portion of a mobile device add patient appointment screen presented to a user by Remote Access Management Systems according to a preferred embodiment of the present invention.
Figure 23:
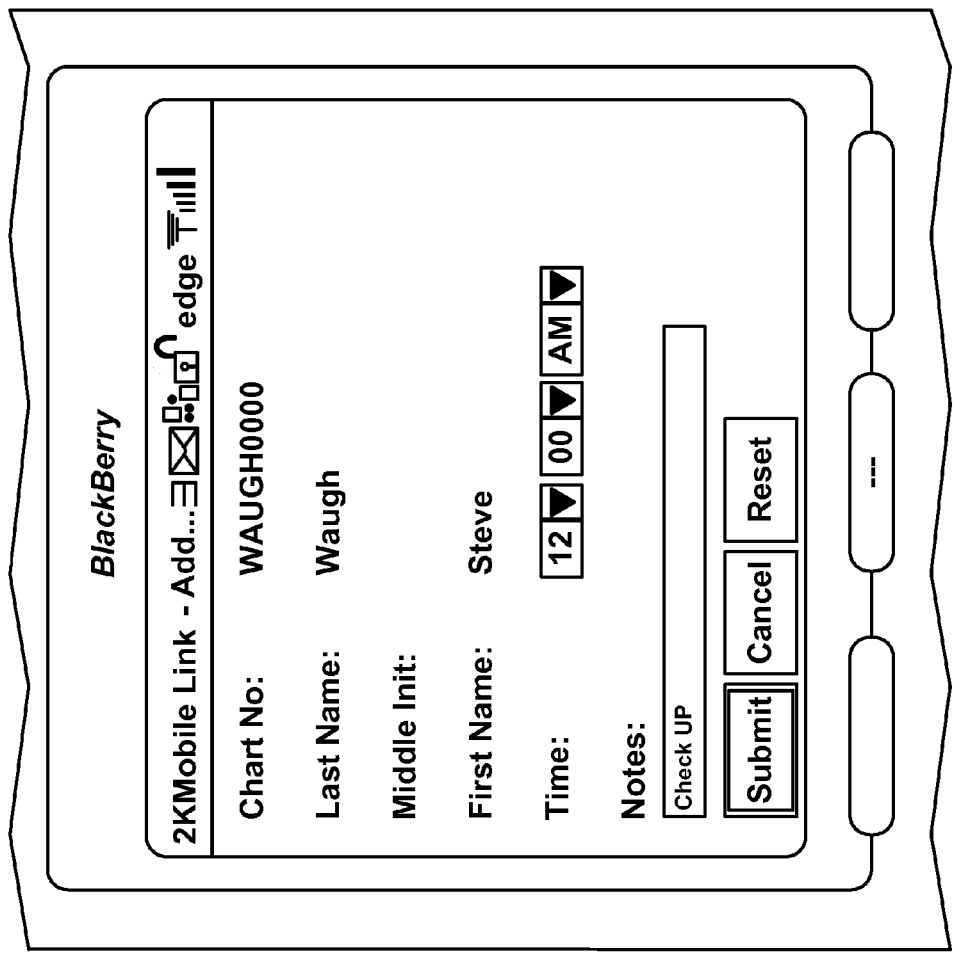
FIG. 23 shows an example of the lower portion of a mobile device add patient appointment screen presented to a user by Remote Access Management Systems according to a preferred embodiment of the present invention.

Referring to FIG. 22 and FIG. 23, which show examples of the mobile device add patient appointment screens presented to Practitioner A 271 by Remote Access Management Systems according to a preferred embodiment of the present invention, preferably an appointment can be scheduled in the following ways:

Go to the Calendar page (Refer to FIG. 7) and click on the New Appointment button, the Search Patient page (as shown in FIG. 9) is displayed and search for a patient and select the desired patient by clicking on the patient's name (Patient link), the Edit Patient pages (as shown in FIG. 17, FIG. 18, FIG. 19 and FIG. 20) are displayed where one may click on the Appointment button as shown on FIG. 20.
Go to Calendar page (Refer to FIG. 7) and click on the New Appointment button to display the Search Patient page (as shown in FIG. 9). Search for a patient and select the Checkbox on the left of the patient's name (Patient link) of the patient for which the appointment has to be scheduled and click on the New Appointment button, which preferably will display the Add Appointment pages (as shown in FIG. 22 and FIG. 23).
On the Calendar page (Refer to FIG. 24), from the appointment list select the Checkbox on the left of the Appointment link of the patient for which the appointment has to be scheduled and click on the New Appointment button, the Add Appointment pages (as shown in FIG. 22 and FIG. 23) are displayed.

Figure 24:
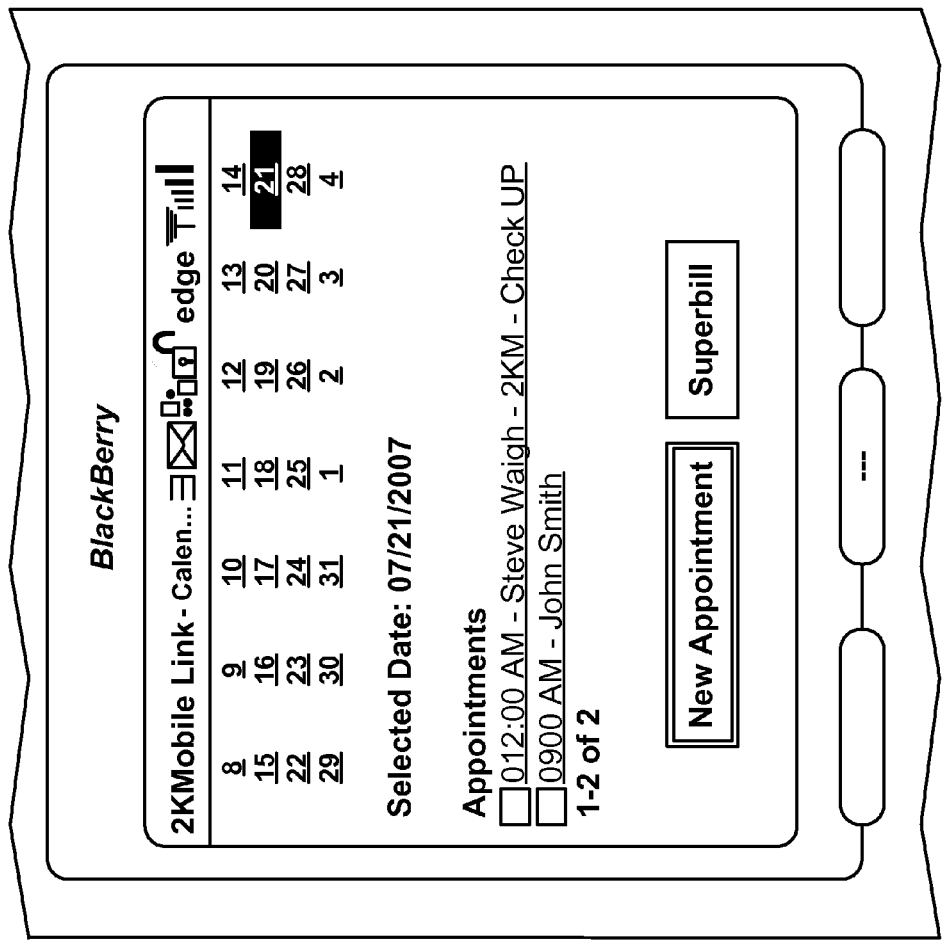
FIG. 24 shows an example of a mobile device calendar screen presented to a user by Remote Access Management Systems after completion of adding a new patient appointment according to a preferred embodiment of the present invention.

Preferably, in the Add Appointment page (as shown in FIG. 22 and FIG. 23) the date selected in the Calendar page is put in the dropdowns (Month, Day, and Year) at the top of the page. To change the date of the appointment, preferably changes are made to the values of the dropdown. FIG. 24 shows an example of a mobile device calendar screen presented to a user by Remote Access Management Systems after completion of adding a new patient appointment according to a preferred embodiment of the present invention. Preferably, clicking the Submit button will save the appointment and display the Calendar page (as shown in FIG. 24) with the appointment scheduled for the recently added appointment date. At least FIGS. 22, 23, 24, and 25 show examples of patient appointment data. As shown at least in FIGS. 22, 23, 24, and 25, patient appointment data may include appointment date, patient appointment time, patient appointment notes, etc.

Figure 25:
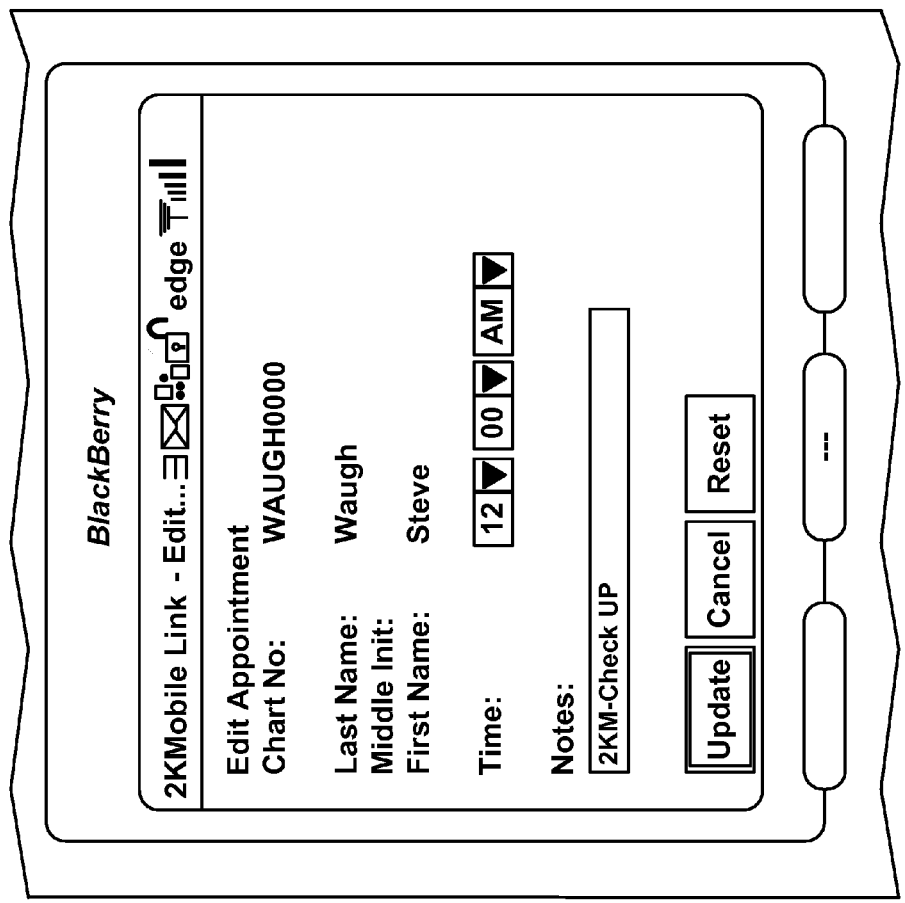
FIG. 25 shows an example of a mobile device edit patient appointment screen presented to a user by Remote Access Management Systems according to a preferred embodiment of the present invention.

Referring to FIG. 25, which shows an example of the mobile device edit patient appointment screen presented to Practitioner A 271 by Remote Access Management Systems according to a preferred embodiment of the present invention, preferably clicking on the Appointment link from the Calendar page (Refer to FIG. 24), displays the Edit Appointment page (See FIG. 25) with the respective appointment displayed. After modifying the appointment clicking on the Update button preferably saves the changes.

Figure 26:
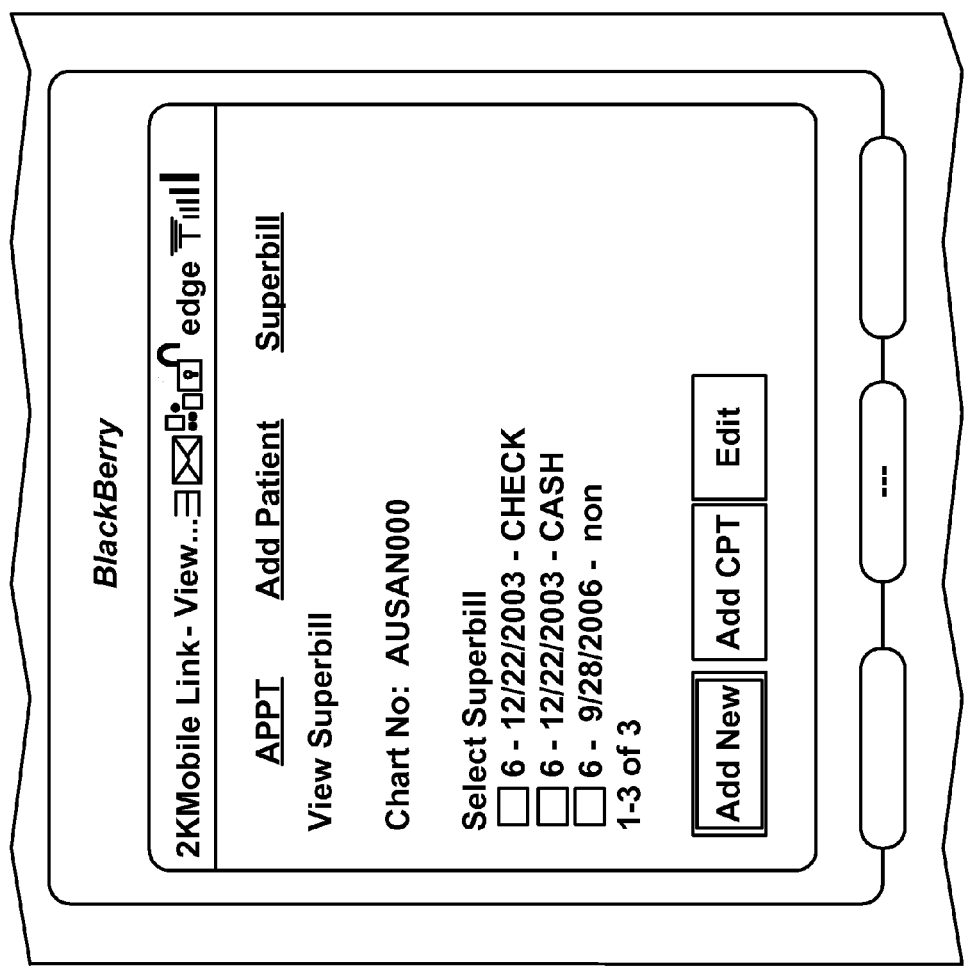
FIG. 26 shows an example of a mobile device view superbill screen presented to a user by Remote Access Management Systems according to a preferred embodiment of the present invention.
Figure 27:
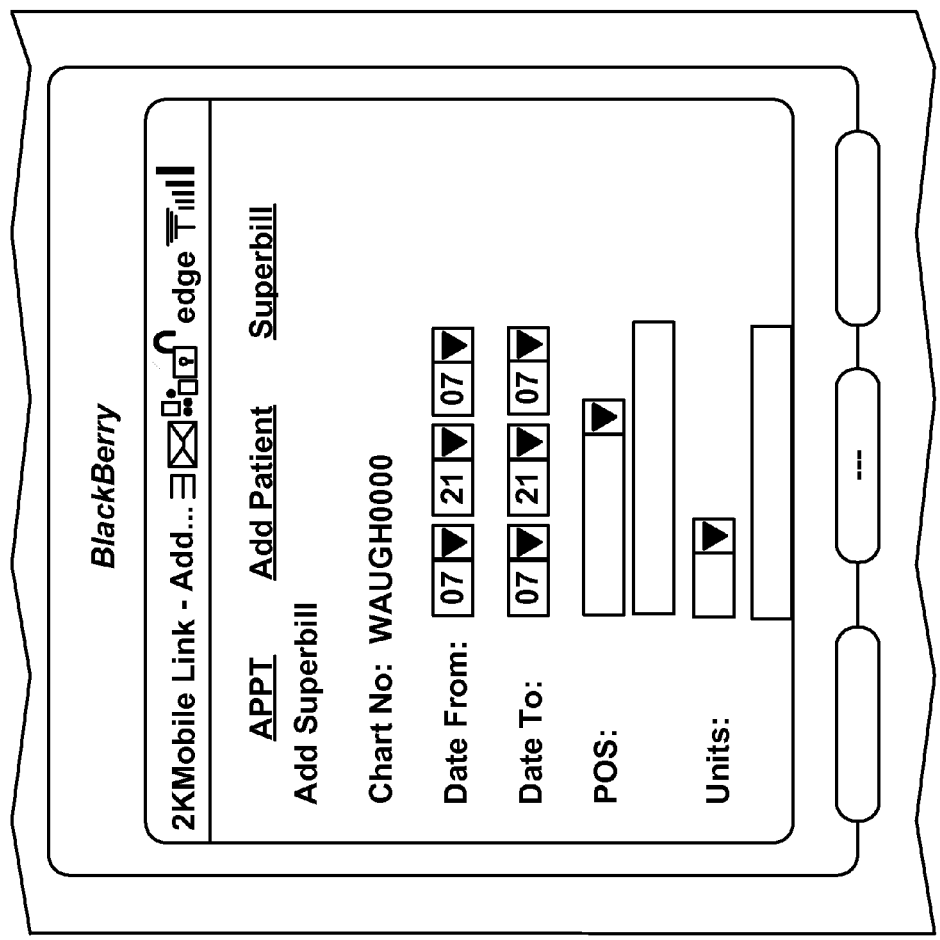
FIG. 27 shows an example of the first portion of a mobile device add patient superbill screen presented to a user by Remote Access Management Systems according to a preferred embodiment of the present invention.

Referring to FIG. 26, which shows an example of the mobile device view superbill screen presented to Practitioner A 271 by Remote Access Management Systems according to a preferred embodiment of the present invention, the Superbill is displayed as—"Billing Number—Service Date—CPT Code" (For example "6—12/22/2003—CHECK") by default. Preferably, the display order may be customized as described below.

Preferably, a Superbill for a patient can be accessed in the following ways:

Clicking on the Superbill link on the menu displays the Search Patient page (as shown in FIG. 9). Search for a patient and click on a patient link to go to View Superbill page (Refer to FIG. 25) for the respective patient.

Clicking on the Superbill button from the Calendar page (Refer to FIG. 7) displays the Search Patient page (as shown in FIG. 9). Search for a patient and click on a patient link to go to View Superbill page (Refer to FIG. 25) for the respective patient.

Selecting a Checkbox on the left of the appointment links in the Calendar page (Refer to FIG. 24) then clicking on the Superbill button displays the Search Patient page (as shown in FIG. 9). Preferably, searching for a patient and clicking on the desired patient's name (Patient link) displays View Superbill page (Refer to FIG. 26) for the respective patient.

Selecting a Checkbox on the left of the patient's name (Patient link) in the Search Patient page (as shown in FIG. 10 and FIG. 11) and clicking on the Superbill button displays the View Superbill page (Refer to FIG. 26) for the respective patient.

Clicking a patient link after searching for patient in the Search Patient page (as shown in FIG. 10 and FIG. 11) displays the Edit Patient page (Refer to FIG. 17, FIG. 18, FIG. 19, and FIG. 20). Preferably, clicking on the Superbill button (as shown in FIG. 20) displays the View Superbill page (Refer to FIG. 26) for the respective patient.

Referring to FIG. 27, FIG. 28, FIG. 29, and FIG. 30, which show examples of the mobile device add patient superbill screens presented to Practitioner A 271 by Remote Access Management Systems according to a preferred embodiment of the present invention, preferably clicking the Add New button, (shown in FIG. 26), displays the Add Superbill page. Preferably, the Date From and Date To fields are populated with the current date unless the navigation to View Superbill is done as shown below. At least FIGS. 27, 28, 29, 30 show examples of patient-related diagnostic and procedure code data (also referred to and related to patient superbill data). As shown at least in FIGS. 27, 28, 29, and 30, patient-related diagnostic and procedure code data includes CPT Code (procedure code data), Diagnosis Code (diagnostic code data), related items, related notes, etc.

Preferably, selecting a Checkbox on the left of the appointment links in the Calendar page (Refer to FIG. 24) and clicking on the Superbill button on the Calendar page (Refer to FIG. 24) displays the View Superbill page (Refer to FIG. 26) for the respective patient.

Preferably, in the above case the Date From and Date To fields are populated with the appointment date of the link which was selected in the Calendar page (Refer to FIG. 24).

Figure 30:
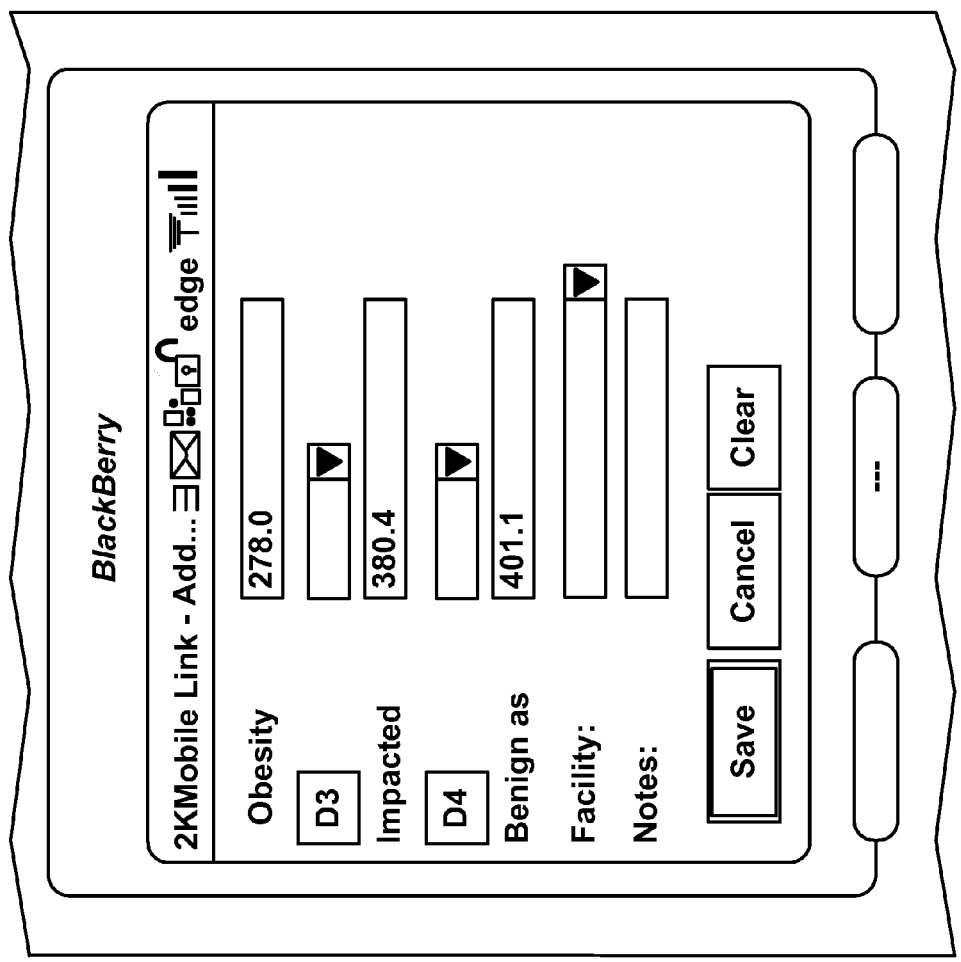
FIG. 30 shows an example of the fourth portion of a mobile device add patient superbill screen presented to a user by Remote Access Management Systems according to a preferred embodiment of the present invention.

Preferably, clicking on the Save button (as shown in FIG. 30) saves the Superbill and displays the View Superbill page (as shown in FIG. 26) with the recently added Superbill on top of the Superbill List.

Preferably, from the View Superbill page (as shown in FIG. 26) selecting a Superbill by selecting the Checkbox on left of the Superbill list and clicking on the Add CPT button displays the Add CPT Code to Superbill page (See FIG. 35, FIG. 36, and FIG. 37) with all the Fields populated from the selected Superbill. Preferably, after making the required changes, clicking on the Save button saves the newly added CPT code to the existing Superbill.

Preferably, adding a CPT to an Existing Superbill can also be done by clicking on the Edit button on the View Superbill page (See FIG. 26).

Preferably, from the View Superbill page (See FIG. 26) selecting a Superbill by selecting the Checkbox and clicking on the Edit button displays the Edit Superbill page. After editing, preferably clicking on the Update button to saves the changes and displays the View Superbill page (See FIG. 26).

Figure 28:
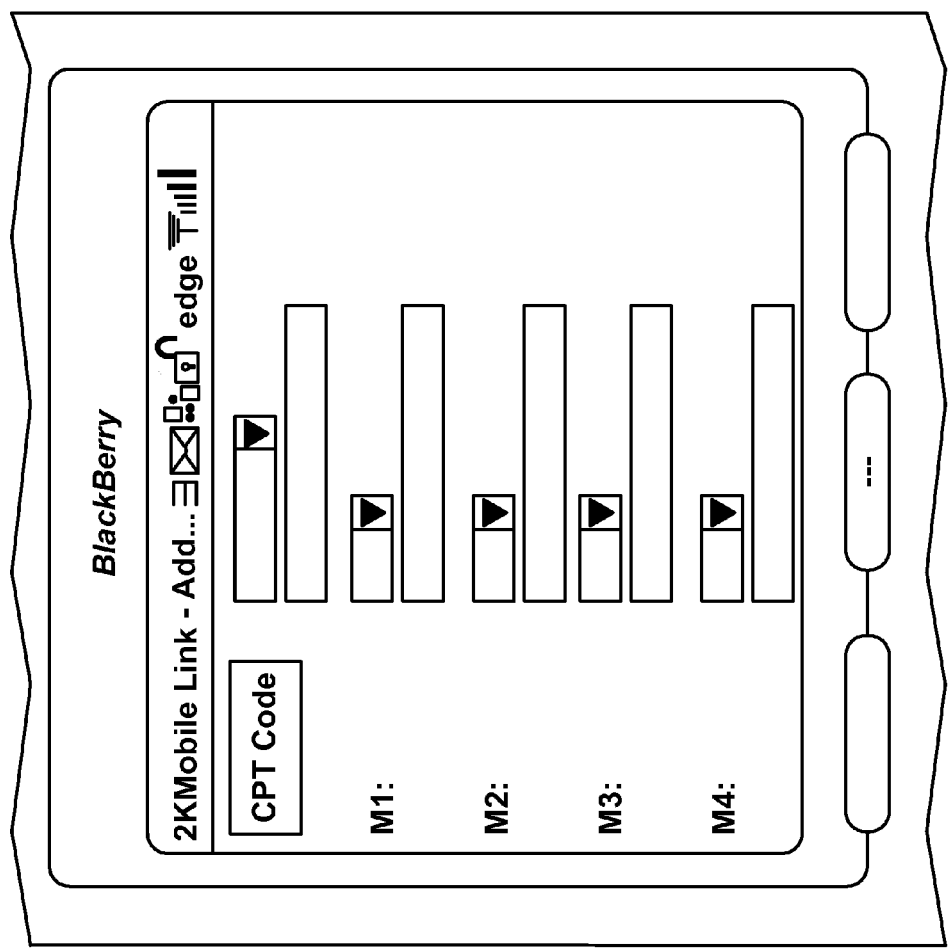
FIG. 28 shows an example of the second portion of a mobile device add patient superbill screen presented to a user by Remote Access Management Systems according to a preferred embodiment of the present invention.
Figure 31:
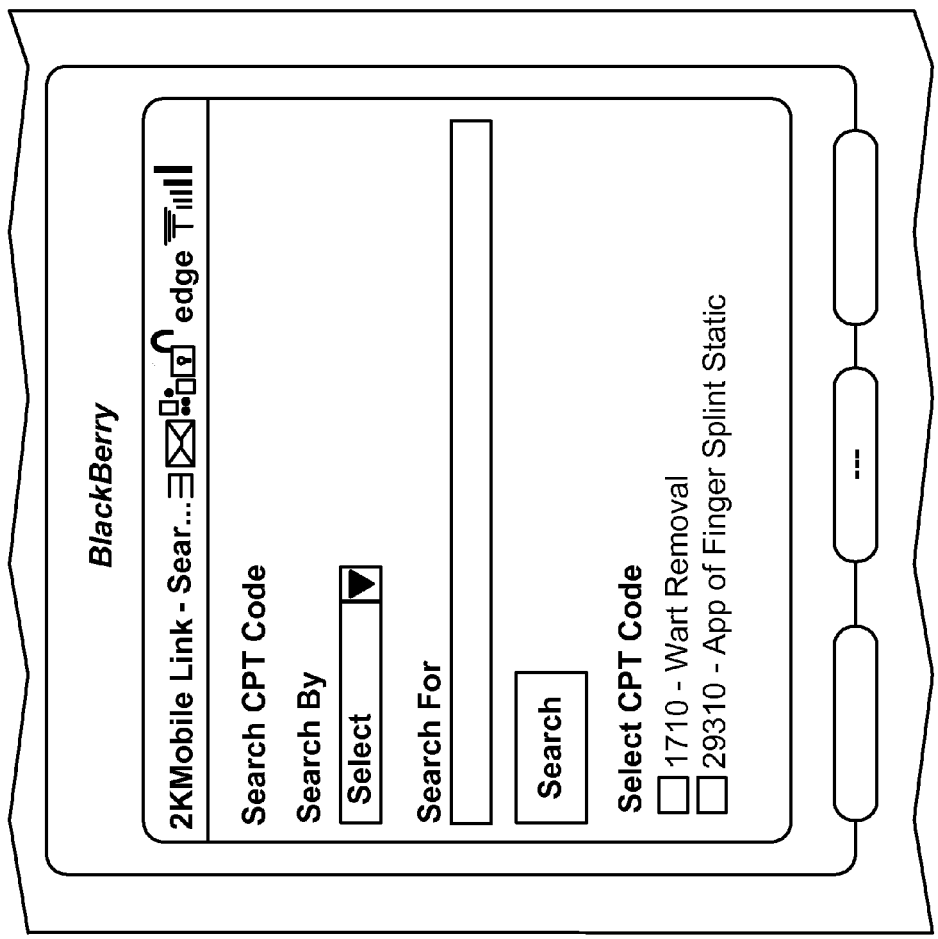
FIG. 31 shows an example of the first portion of a mobile device search CPT Code screen presented to a user by Remote Access Management Systems according to a preferred embodiment of the present invention.
Figure 32:
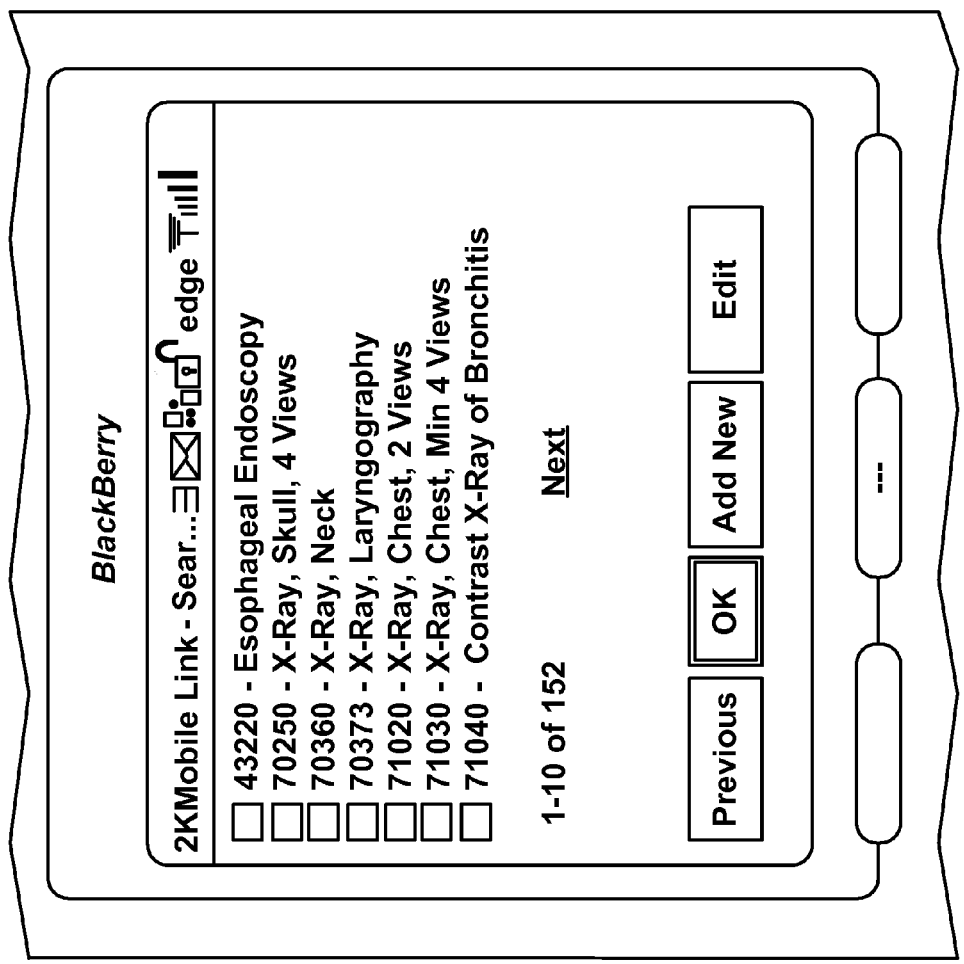
FIG. 32 shows an example of the second portion of a mobile device search CPT Code screen presented to a user by Remote Access Management Systems according to a preferred embodiment of the present invention.

Referring to FIG. 31 and FIG. 32, which show examples of the mobile device search CPT Code screens presented to Practitioner A 271 by Remote Access Management Systems according to a preferred embodiment of the present invention, preferably clicking on the CPT Code (CPT Code and related information at least embodies herein procedure code data) button as shown in FIG. 28 displays the Search CPT Code page as shown in FIG. 31 and FIG. 32. Searching for a CPT Code and selecting a CPT Code by clicking the OK button displays the Add Superbill page (Refer to FIG. 27) with the CPT Code field populated with the selected CPT Code from the Search CPT Code page as shown in FIG. 31 and FIG. 32.

Figure 29:
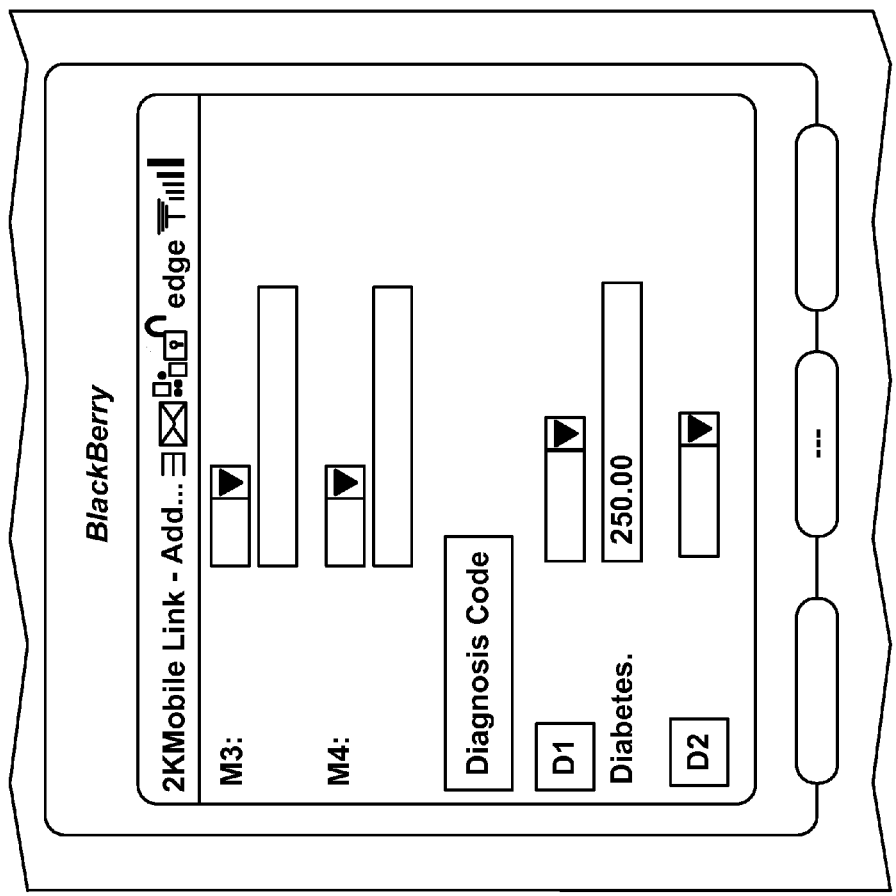
FIG. 29 shows an example of the third portion of a mobile device add patient superbill screen presented to a user by Remote Access Management Systems according to a preferred embodiment of the present invention.
Figure 33:
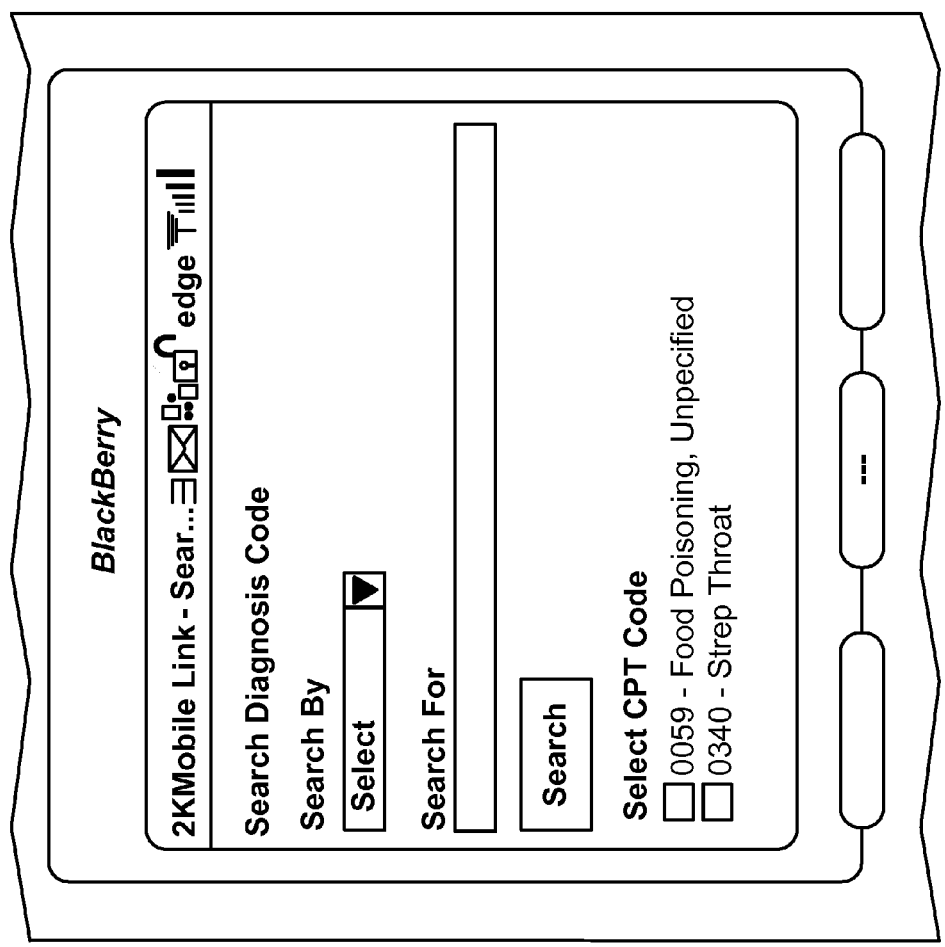
FIG. 33 shows an example of the first portion of a mobile device search Diagnosis Code screen presented to a user by Remote Access Management Systems according to a preferred embodiment of the present invention.
Figure 34:
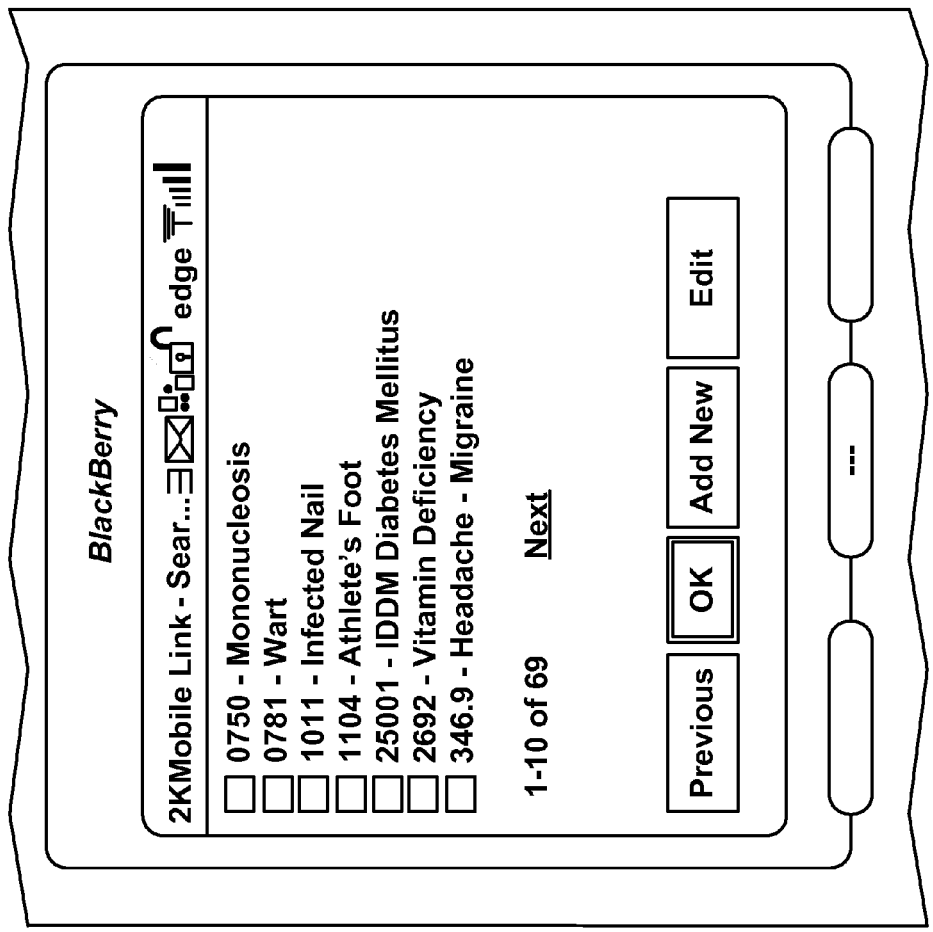
FIG. 34 shows an example of the second portion of a mobile device search Diagnosis Code screen presented to a user by Remote Access Management Systems according to a preferred embodiment of the present invention.

Referring to FIG. 33 and FIG. 34 which show examples of the mobile device search Diagnosis Code screens presented to Practitioner A 271 by Remote Access Management Systems according to a preferred embodiment of the present invention, preferably clicking on the Diagnosis Code button (as shown in FIG. 29), displays the Search Diagnosis Code page (Refer to FIG. 33 and FIG. 34). Searching and selecting Diagnosis Code (Diagnostic Code and related imformation at least embodies herein diagnostic code data) by clicking the OK button displays the Add Superbill page (as shown in FIG. 27, FIG. 28, FIG. 29, and FIG. 30) with the Diagnosis Code fields (D1, D2, D3, D4) populated with the selected Diagnosis Code from the Search Diagnosis Code page as shown in FIG. 33 and FIG. 34.

Figure 35:
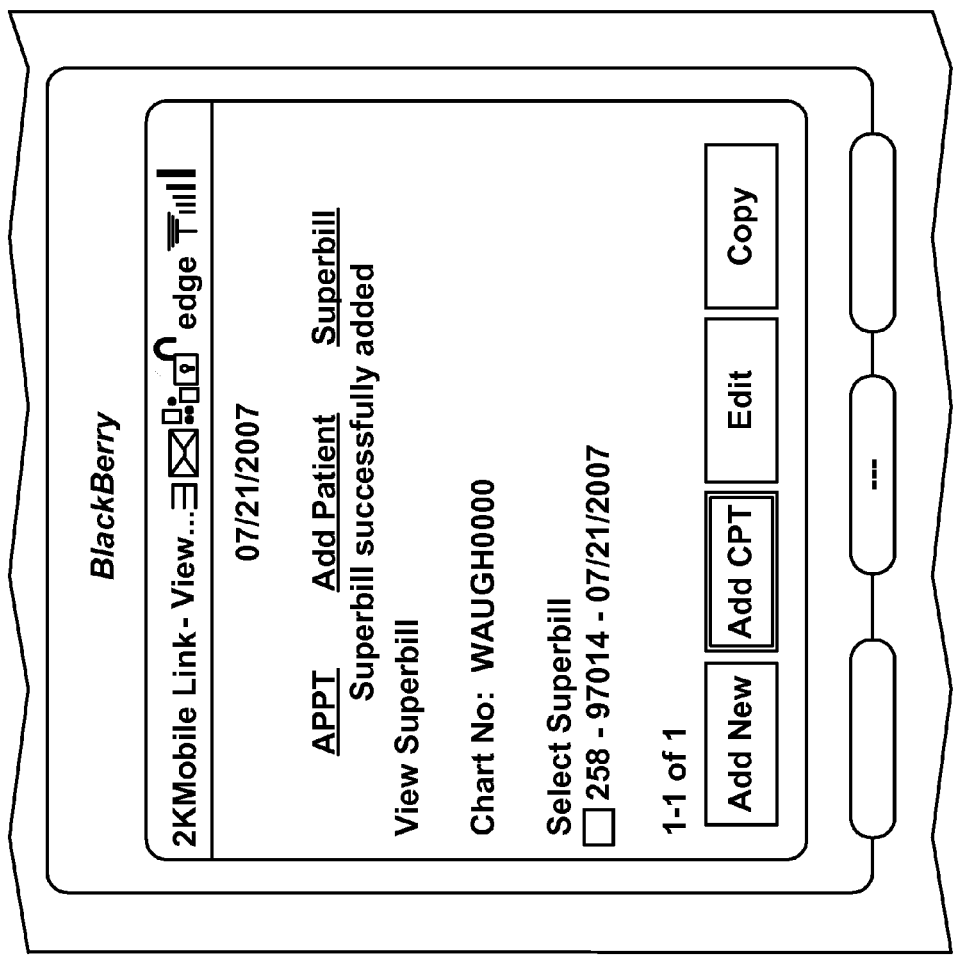
FIG. 35 shows an example of a mobile device screen displaying the Add CPT link presented to a user by Remote Access Management Systems according to a preferred embodiment of the present invention.

FIG. 35 shows an example of a mobile device screen displaying the Add CPT link presented to a user by Remote Access Management Systems according to a preferred embodiment of the present invention.

Figure 36:
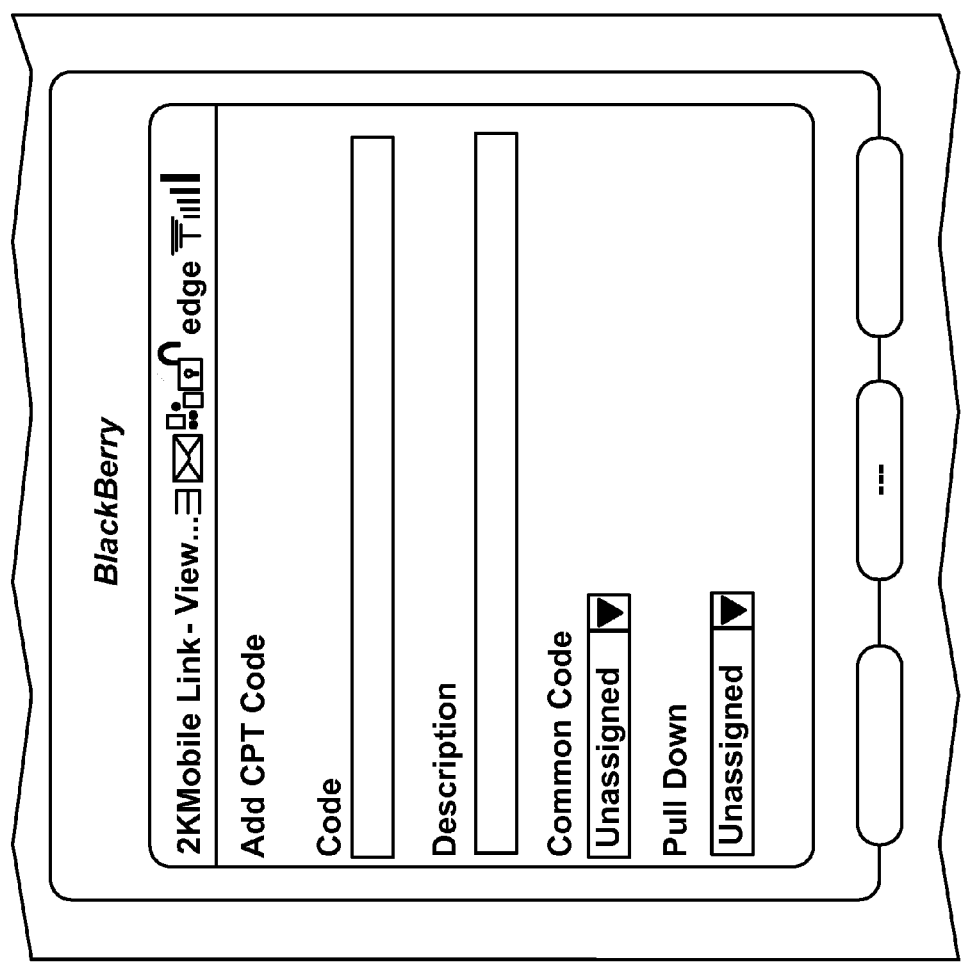
FIG. 36 shows an example of the first portion of a mobile device add CPT Code screen presented to a user by Remote Access Management Systems according to a preferred embodiment of the present invention.
Figure 37:
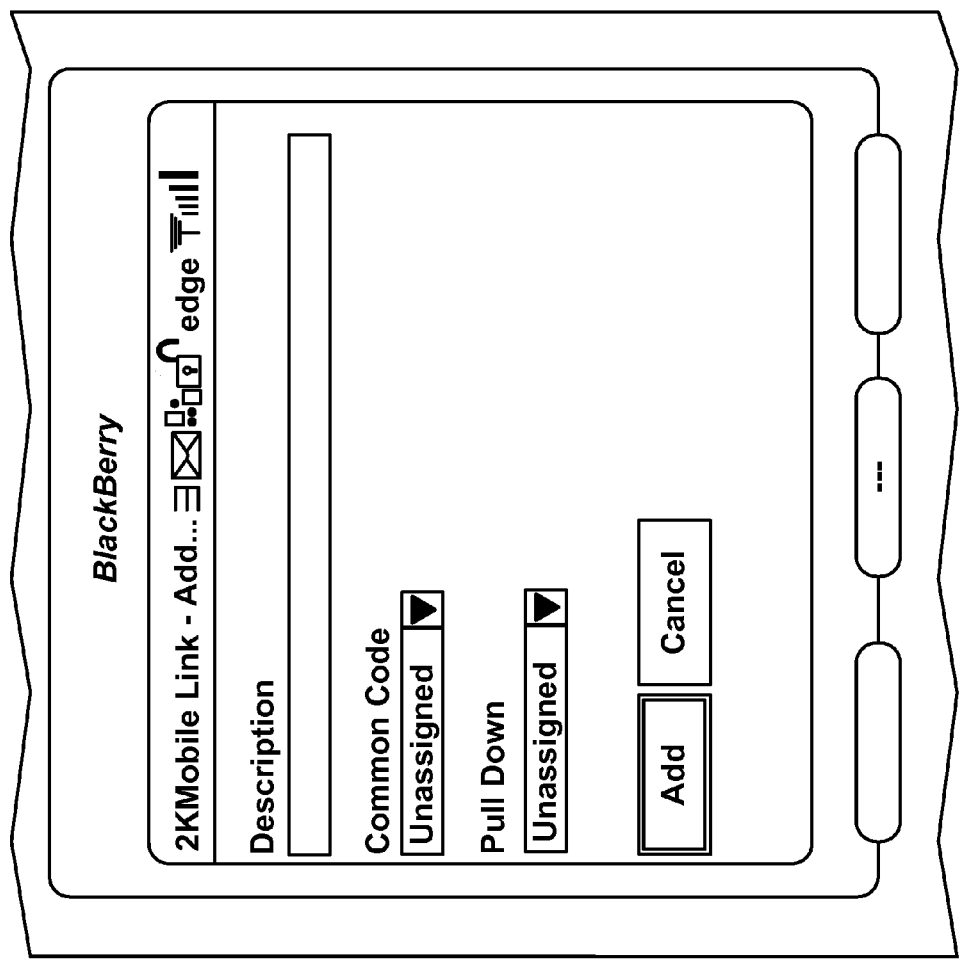
FIG. 37 shows an example of the second portion of a mobile device add CPT Code screen presented to a user by Remote Access Management Systems according to a preferred embodiment of the present invention.

Referring to FIG. 36 and FIG. 37, which show examples of the mobile device add CPT Code screen presented to Practitioner A 271 by Remote Access Management Systems according to a preferred embodiment of the present invention, preferably clicking on the Add New button on the Search CPT Code page as shown in FIG. 32 displays the Add CPT Code page (See FIG. 36). Preferably, after entering the details (CPT Code, description, Common Code) and clicking on the Add button (FIG. 37) saves the new CPT Code and displays the Search CPT Code page with the recently added CPT Code (See FIG. 38 and FIG. 39).

Figure 38:
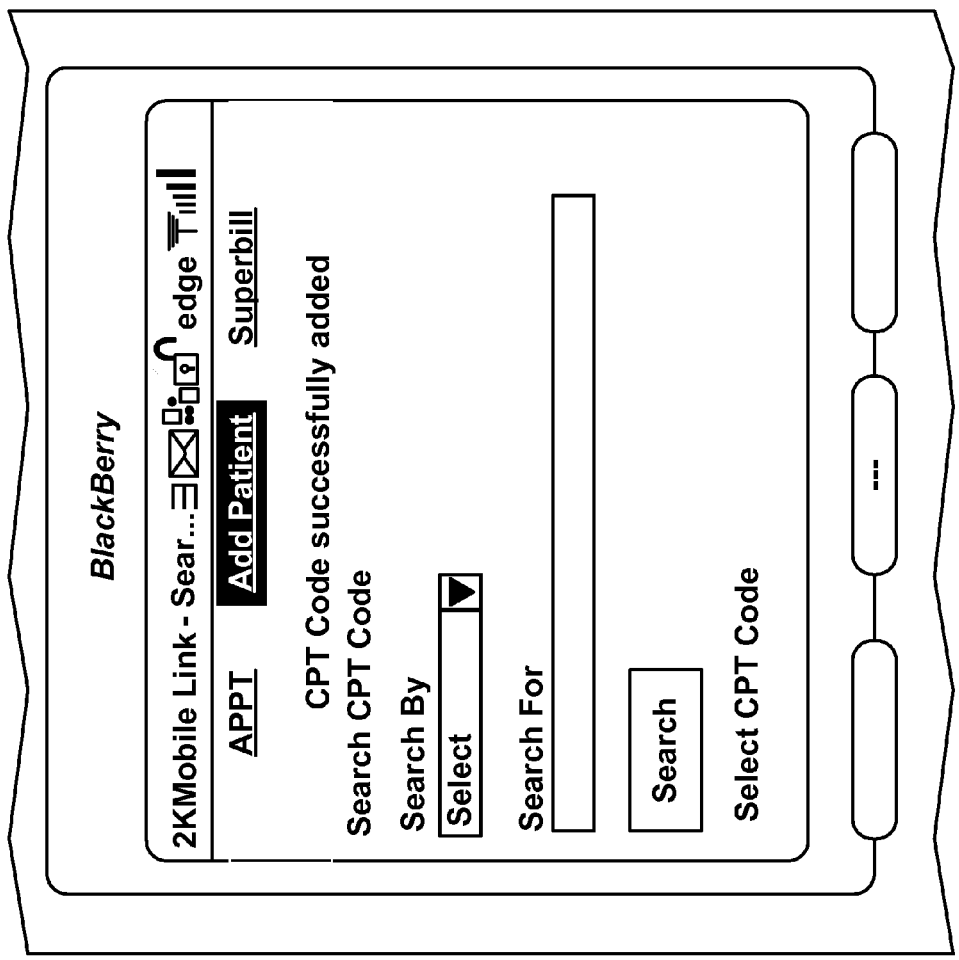
FIG. 38 shows an example of a mobile device search CPT Code screen presented to a user by Remote Access Management Systems according to a preferred embodiment of the present invention.

FIG. 38 shows an example of a mobile device search CPT Code screen presented to a user by Remote Access Management Systems according to a preferred embodiment of the present invention.

Figure 39:
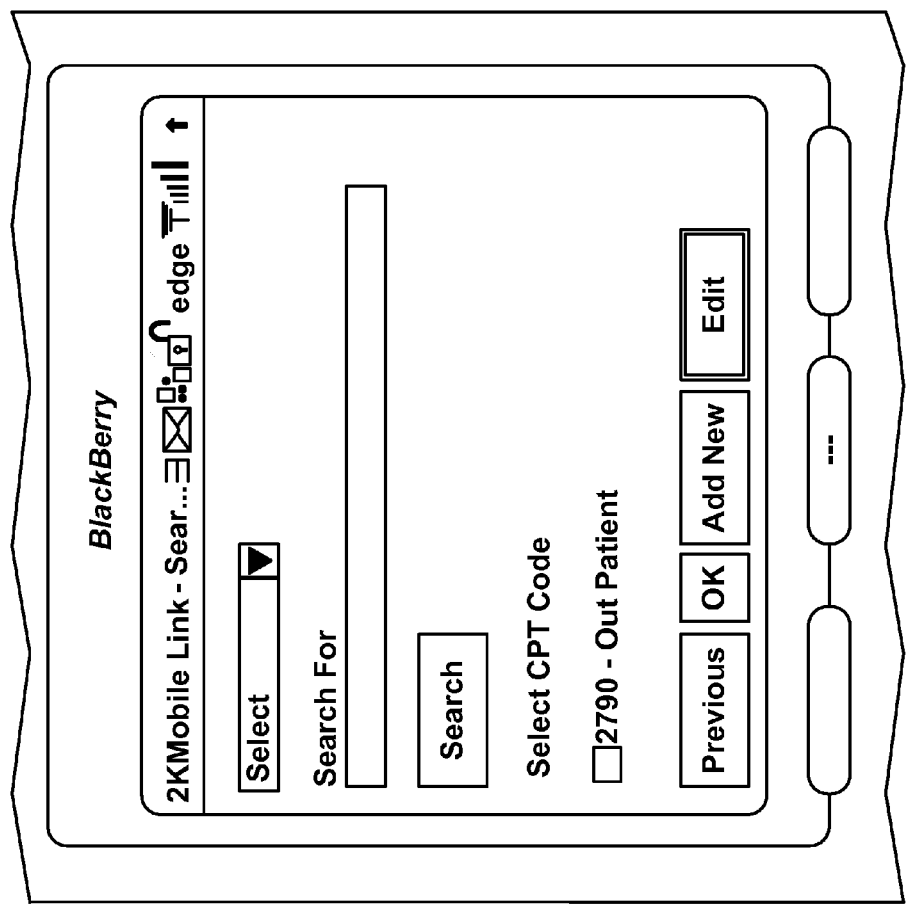
FIG. 39 shows an example of a mobile device screen, displaying selection of the Edit button to edit a CPT Code, presented to a user by Remote Access Management Systems according to a preferred embodiment of the present invention.

FIG. 39 shows an example of a mobile device screen, displaying selection of the Edit button to edit a CPT Code, presented to a user by Remote Access Management Systems according to a preferred embodiment of the present invention.

Figure 40:
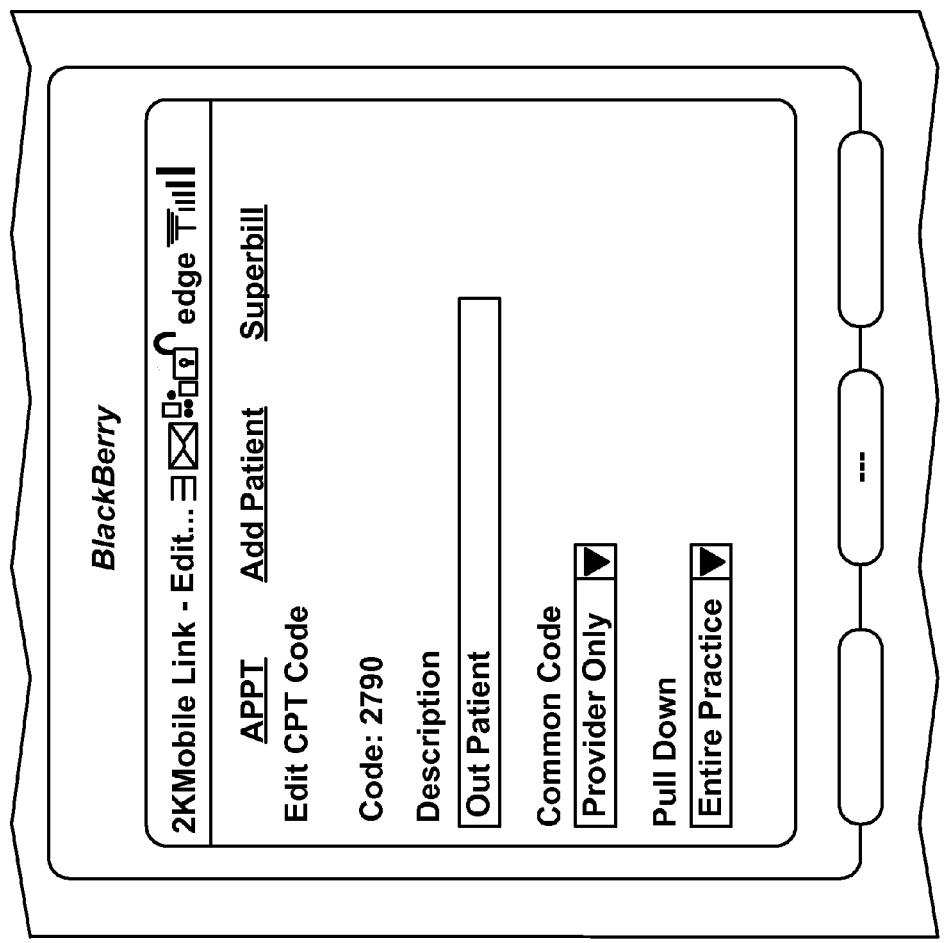
FIG. 40 shows an example of the first portion of a mobile device edit CPT Code screen presented to a user by Remote Access Management Systems according to a preferred embodiment of the present invention.
Figure 41:
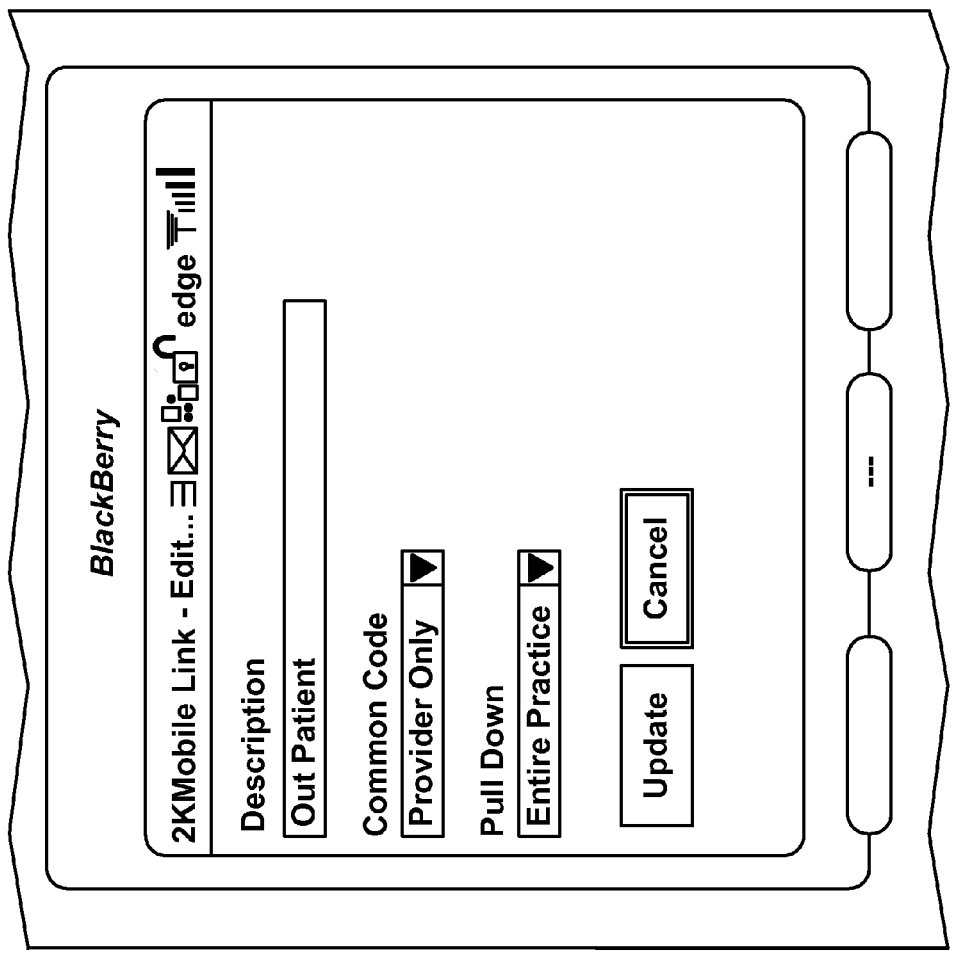
FIG. 41 shows an example of the second portion of a mobile device edit CPT Code screen presented to a user by Remote Access Management Systems according to a preferred embodiment of the present invention.

Referring to FIG. 40 and FIG. 41, which show an example of the mobile device edit CPT Code screen presented to Practitioner A 271 by Remote Access Management Systems according to a preferred embodiment of the present invention, preferably selecting a CPT code in the Search CPT Code page and clicking on the Edit button displays the Edit CPT Code page (See FIG. 40) for the selected CPT. Preferably, clicking on the Update button saves the changes and displays the Search CPT Code page with the recently updated CPT Code (See FIG. 38).

Figure 42:
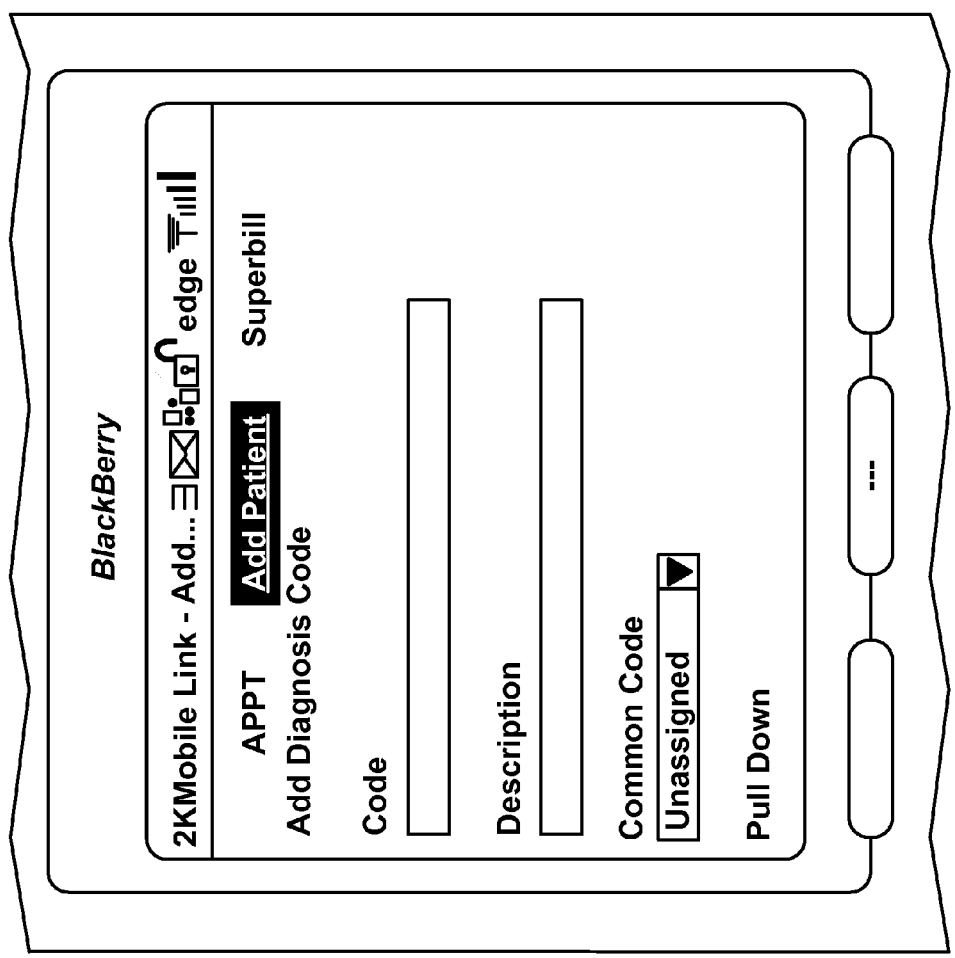
FIG. 42 shows an example of the first portion of a mobile device add Diagnosis Code screen presented to a user by Remote Access Management Systems according to a preferred embodiment of the present invention.
Figure 43:
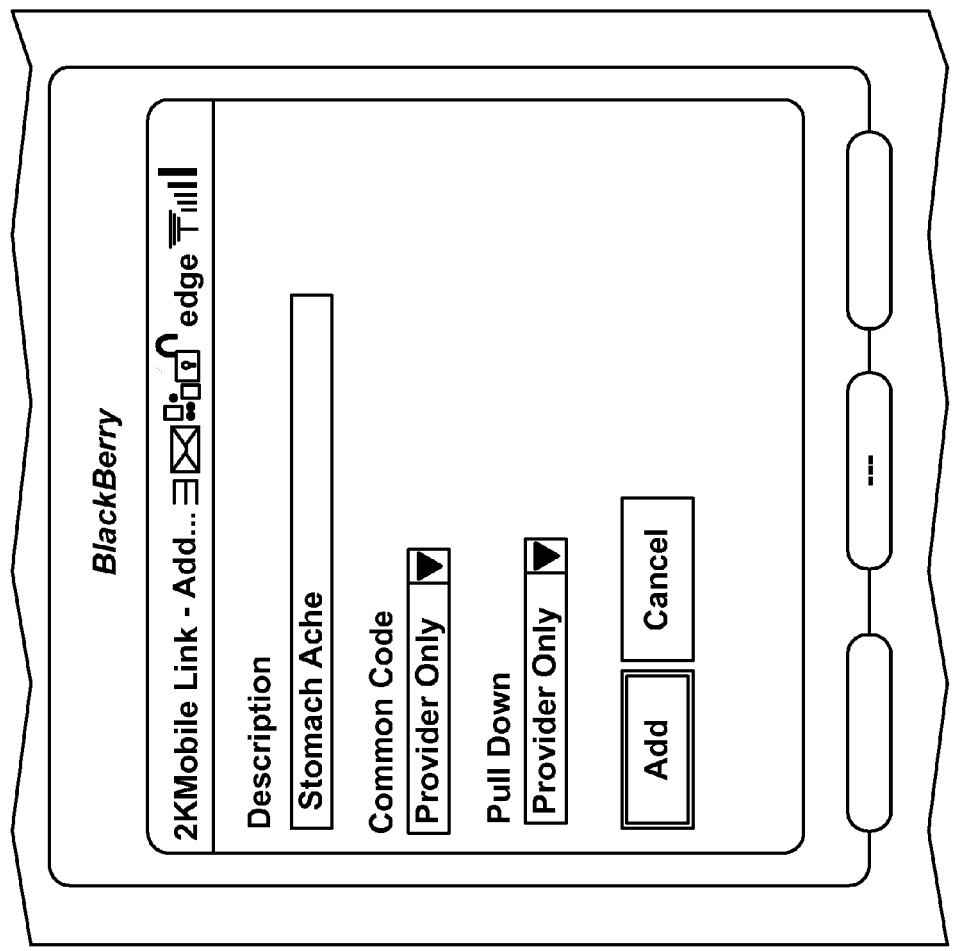
FIG. 43 shows an example of the second portion of a mobile device add Diagnosis Code screen presented to a user by Remote Access Management Systems according to a preferred embodiment of the present invention.

Referring to FIG. 42 and FIG. 43, which shows an example of the mobile device add Diagnosis Code screen presented to Practitioner A 271 by Remote Access Management Systems according to a preferred embodiment of the present invention, preferably clicking on the Add New button on the Search Diagnosis Code page as shown in FIG. 34 displays the Add Diagnosis Code page (See FIG. 42). Preferably, after entering the details (Diagnosis Code, description, Common Code), clicking on the Add button saves the new Diagnosis Code and displays the Search Diagnosis Code page with the recently added Diagnosis Code (See FIG. 33 and FIG. 34). Preferably, a success message is displayed (not shown) to communicate success in adding the desired Diagnosis Code.

Figure 44:
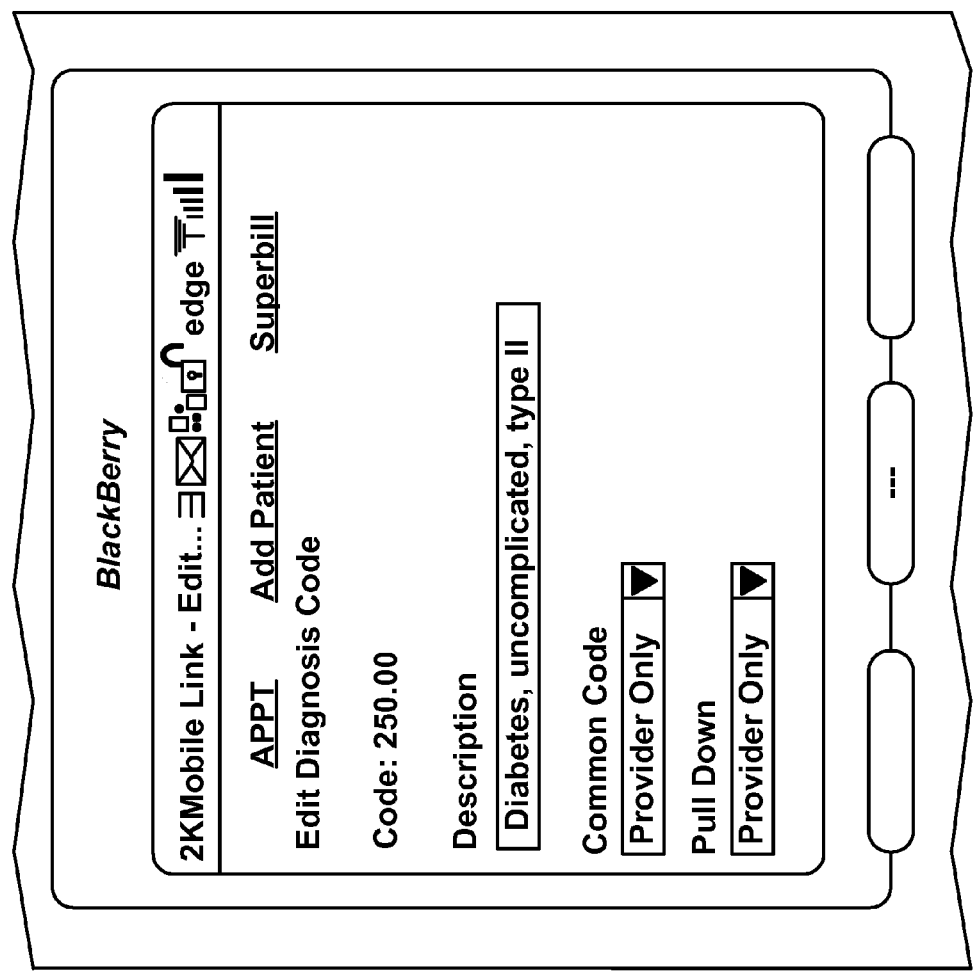
FIG. 44 shows an example of the first portion of a mobile device edit Diagnosis Code screen presented to a user by Remote Access Management Systems according to a preferred embodiment of the present invention.
Figure 45:
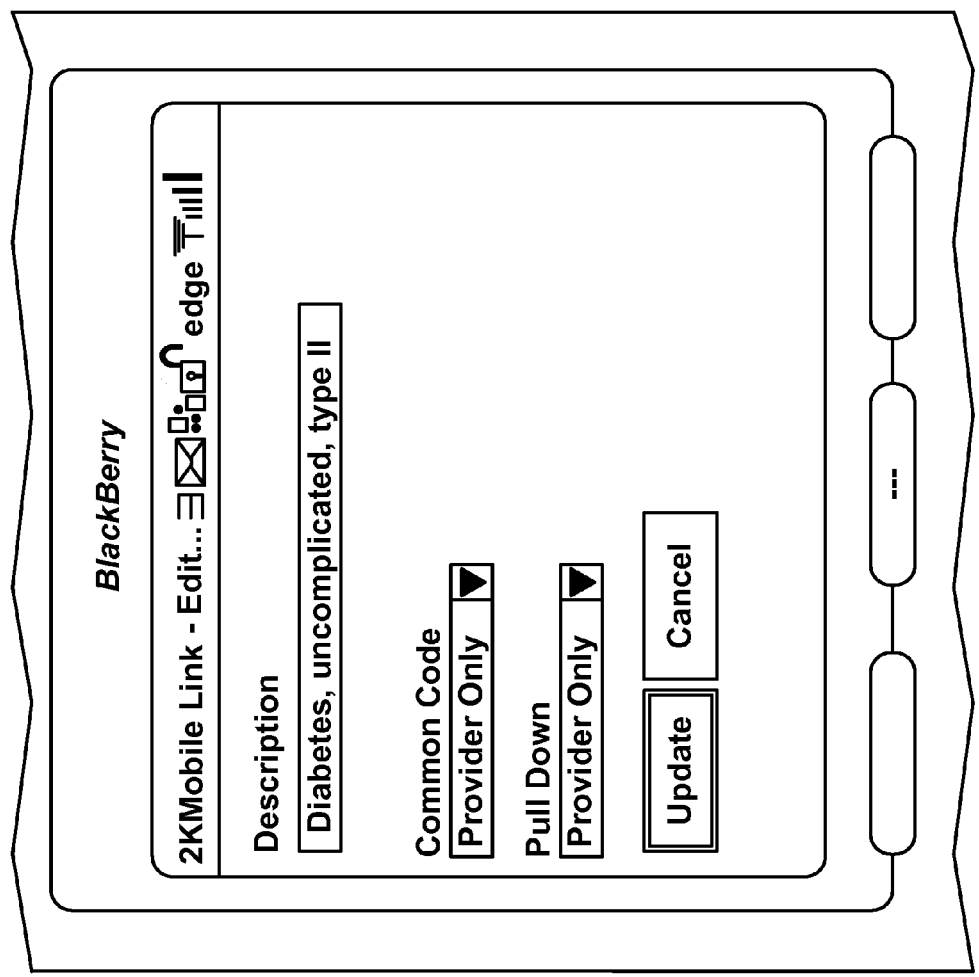
FIG. 45 shows an example of the second portion of a mobile device edit Diagnosis Code screen presented to a user by Remote Access Management Systems according to a preferred embodiment of the present invention.

Referring to FIG. 44 and FIG. 45, which show an example of the mobile device edit Diagnosis Code screen presented to Practitioner A 271 by Remote Access Management Systems according to a preferred embodiment of the present invention, preferably selecting a Diagnosis code in the Search Diagnosis Code page, as shown in FIG. 33 and FIG. 34, and clicking on the Edit button displays the Edit Diagnosis Code page for the selected Diagnosis. Preferably, clicking on the Update button (FIG. 45) saves the changes and displays the Search Diagnosis Code page, as shown in FIG. 33 and FIG. 34, with the recently updated Diagnosis Code.

Figure 46:
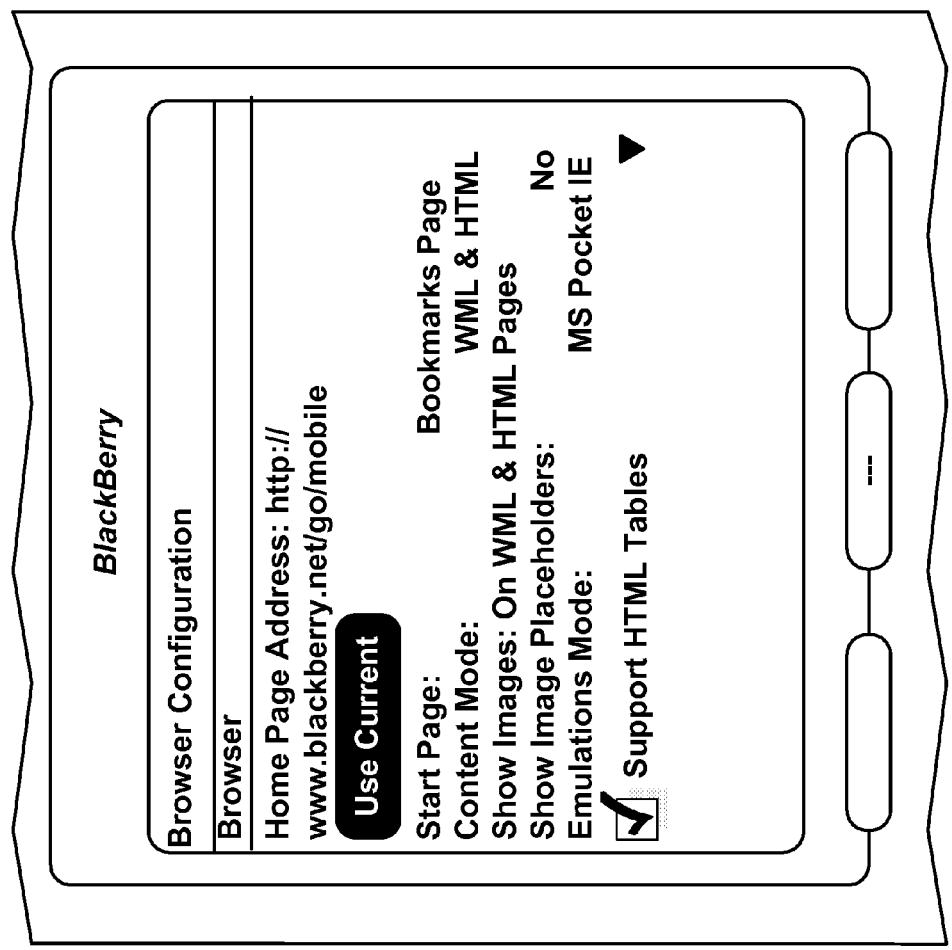
FIG. 46 shows an example of the first portion of a mobile device Browser Configuration screen with the preferred settings for the mobile device selected.
Figure 47:
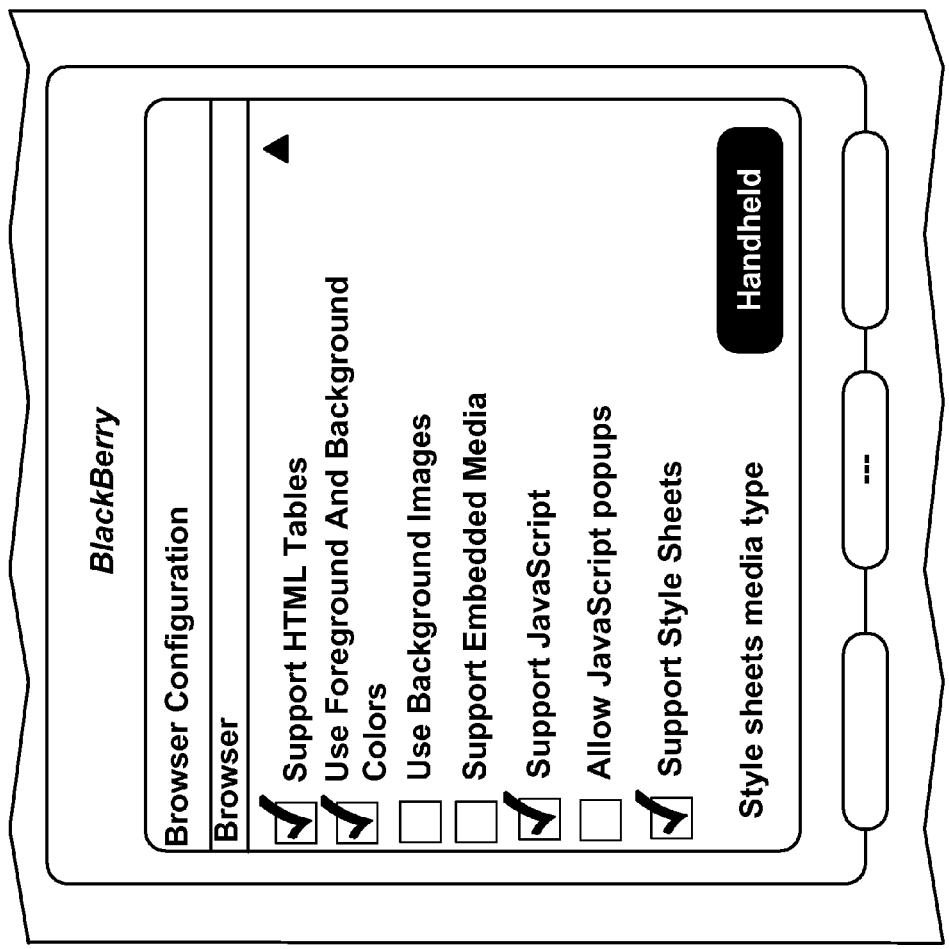
FIG. 47 shows an example of the second portion of a mobile device Browser Configuration screen with the preferred settings for the mobile device selected.

Referring to FIG. 46 and FIG. 47, which show an example of a mobile device Browser Configuration screen with the preferred settings for the mobile device selected, the preferred settings are as follows: Content Mode—WML & HTML; Emulation Mode—MS Pocket IE; Check—"Support HTML Tables", "Use foreground And Background Colors", "Support JavaScript", "Support Style Sheet".

Figure 48:
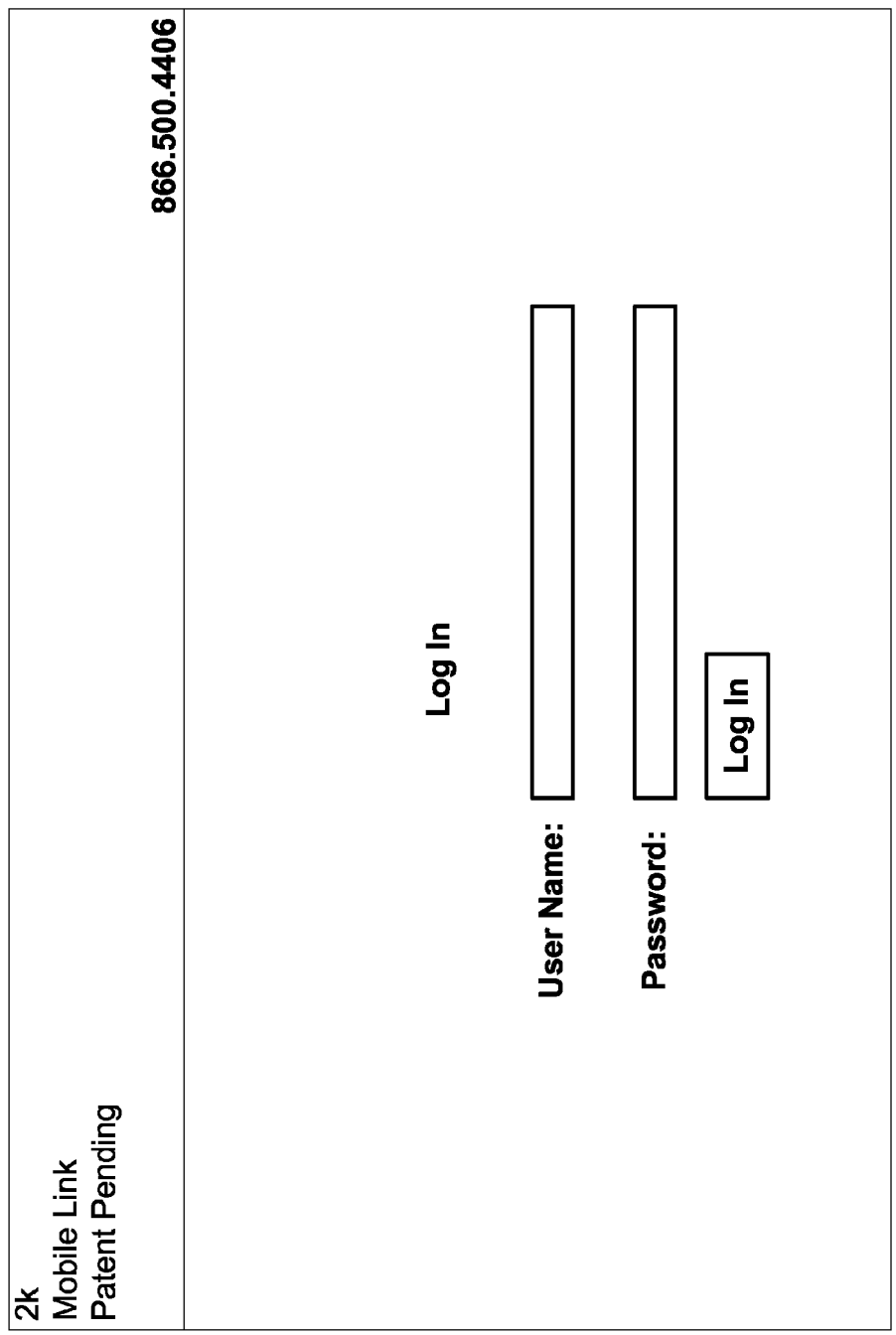
FIG. 48 shows an example of a user log in screen of an Admin Doctor Application presented to a user according to a preferred embodiment of the present invention.

FIG. 48 shows an example of a user log in screen of an Admin Doctor Application presented to a user according to a preferred embodiment of the present invention. The Application shown in FIG. 48 is preferably a web application that will allow an Admin doctor to select and view appointment schedules, appointment details and patient information. An Admin doctor will be able to create new Superbills from specialty specific CPT and Diagnosis codes and add or change patient data. Further, an Admin doctor may preferably make appointments and also set the privileges (described below) for all the doctors under the medical center.

An Admin doctor accesses the Admin Doctor Application by opening an Internet web browser (such as Microsoft Internet Explorer) and typing the appropriate URL (e.g., www.2kmedical.com) into the appropriate place. The Admin doctor will be redirected to the Login screen shown in FIG. 48. The Login page checks for the authenticated physician to make use of the 2KMobileLink application. A user name and password is required to login, as shown. After logging in, the Admin doctor will have control over the application by clicking an "Admin" Tab (not shown). Preferably, this "Admin" Tab will appear only for those who are declared as the Admin doctors in the 2KMobileLink Admin Tool (not shown). Once a user has navigated to the Admin tab, the following preferred options will appear: Control Panel; New Entries; Rule Wizard; Setup; Home; and Log Out.

The Control Panel provides two selectable options: Provider Profile and Default Profile. These Profiles will be applied for both a local Web based doctor application as well as the Mobile application (as described above). Within the Control Panel, a user may set the following features:

- Add Patient: If unchecked, a Doctor user cannot add a Patient.
- Edit Patient: If unchecked, a Doctor user cannot edit a Patient.
- Add Superbill: If unchecked, a Doctor user cannot add a Superbill.
- Edit Superbill: If unchecked, a Doctor user cannot edit a Superbill.
- Add Diagnosis Codes: If unchecked, a Doctor user cannot add Diagnosis Codes.
- Edit Diagnosis Codes: If unchecked, a Doctor user cannot edit Diagnosis Codes.
- Delete Diagnosis Codes: If unchecked, a Doctor user cannot delete Diagnosis Code.
- Add CPT Codes: If unchecked, a Doctor user cannot add CPT Codes.
- Edit CPT Codes: If unchecked, a Doctor user cannot edit CPT Codes.
- Delete CPT Codes: If unchecked, a Doctor user cannot delete CPT Codes.
- Add Appointment: If unchecked, a Doctor user cannot add an Appointment.
- Edit Appointment: If unchecked, a Doctor user cannot edit an Appointment.
- Check bill to patient and insurance companies: If unchecked, while adding a Superbill, the AutoBillPatient and PrimaryAutoBill fields in a Patient Table will be updated.
- Change a Superbill that has been billed: If unchecked, a Doctor user cannot edit a Superbill that has been billed.
- Post charge amounts if amount is entered: If unchecked, a Doctor user cannot calculate the amount for the Superbill.
- View Multiple Providers Appointments: If unchecked, a Doctor user cannot view All Providers Appointments.
- View reports: If unchecked, a Doctor user cannot view the reports and files posted online.
- Overwrite rules in Superbill: If unchecked, a Doctor user cannot overwrite rules for the Superbills if the CPT has a rule.
- Assign Insurance Company details to Patients: If unchecked, a Doctor user cannot assign insurance company details while adding/editing a patient.
- Change Charge Amount for CPT Codes: If unchecked, a Doctor user cannot edit the charge amount for the CPT Codes in the Superbill page.
- Review Patient New Entries: If checked, a Patient record added by a Doctor user will go to a database as well as to an Admin database.
- Review Appointment New Entries: If checked, a Appointment record added by a Doctor user will go to a database as well as an Admin database.

Review Superbill New Entries: If checked, a Superbill record added by a Doctor user will go to a database as well as to an Admin database.

Review CPT New Entries: If checked, a CPT record added by a Doctor user will go to a database as well as an Admin database.

Review Diagnosis New Entries: If checked, a Diagnosis record added by a Doctor user will go to a database as well as an Admin database.

Figure 49:
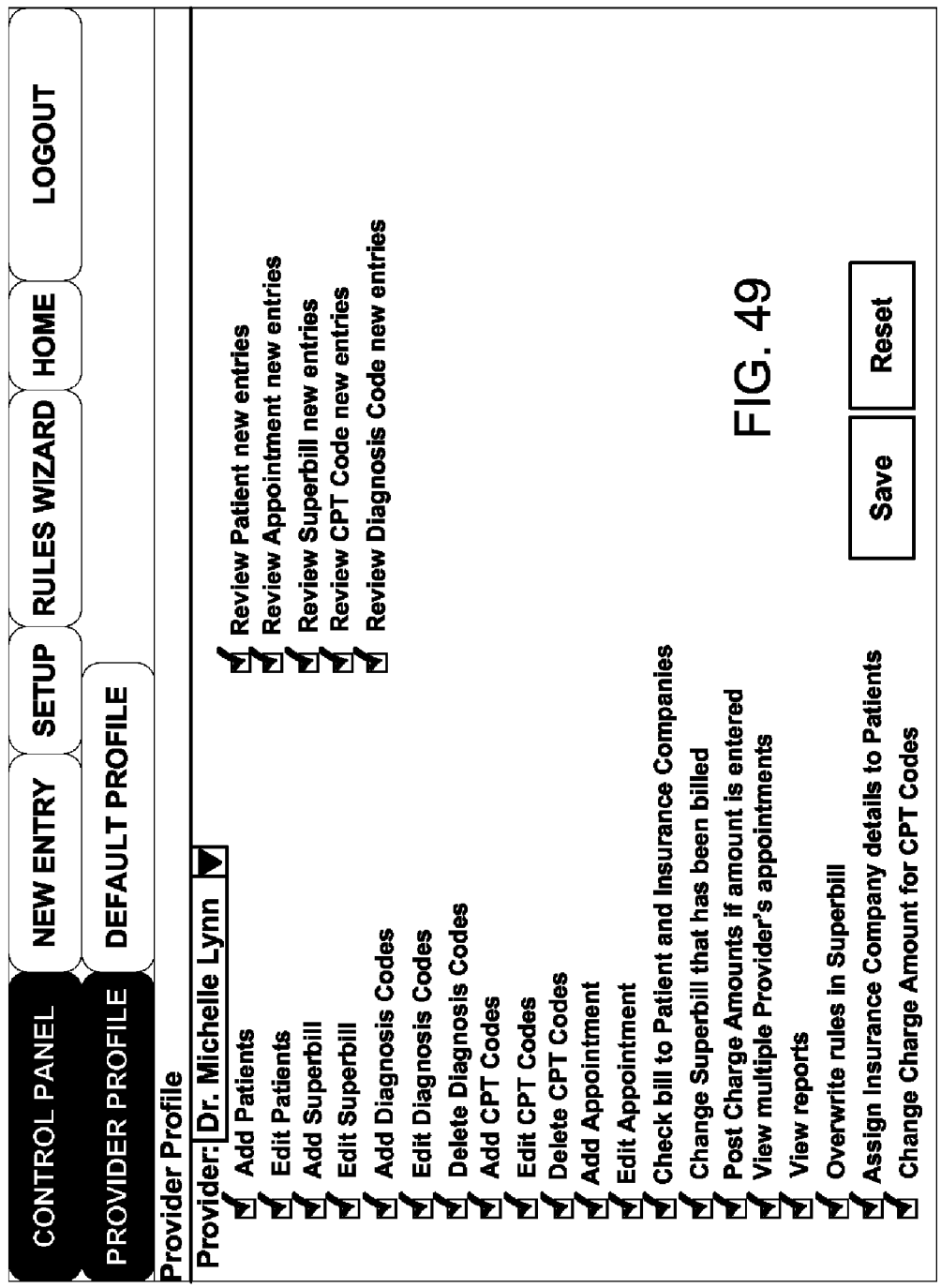
FIG. 49 shows an example of a Provider Profile screen of the Admin Doctor Application presented to a user according to a preferred embodiment of the present invention.

The above listed features may be selected by navigating to the Provide Profile tab in the Control Panel as shown in FIG. 49.

FIG. 49 shows an example of a Provider Profile screen of the Admin Doctor Application presented to a user according to a preferred embodiment of the present invention. If the default profile is desired, an Admin user preferably clicks on the Default Profile tab. If a Provider Profile for a doctor has not been created, the options in the Default Profile tab will preferably be selected.

Figure 50:
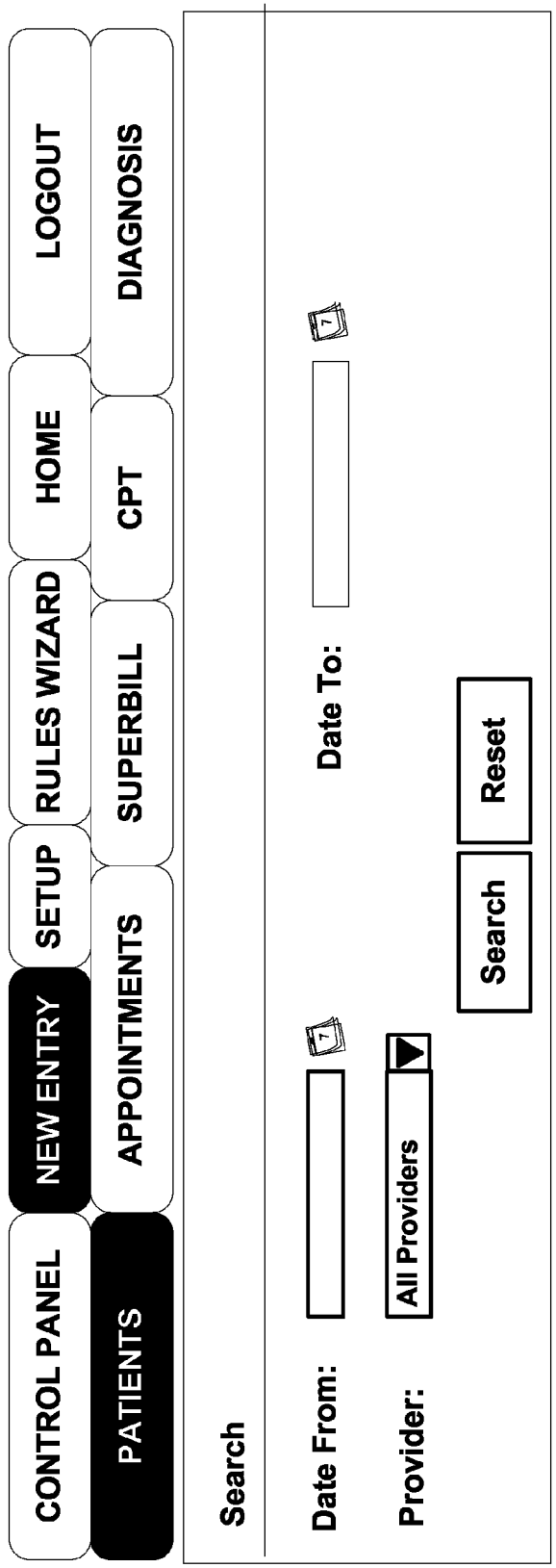
FIG. 50 shows an example of a New Entries Search screen of the Admin Doctor Application presented to a user according to a preferred embodiment of the present invention.
Figure 62:
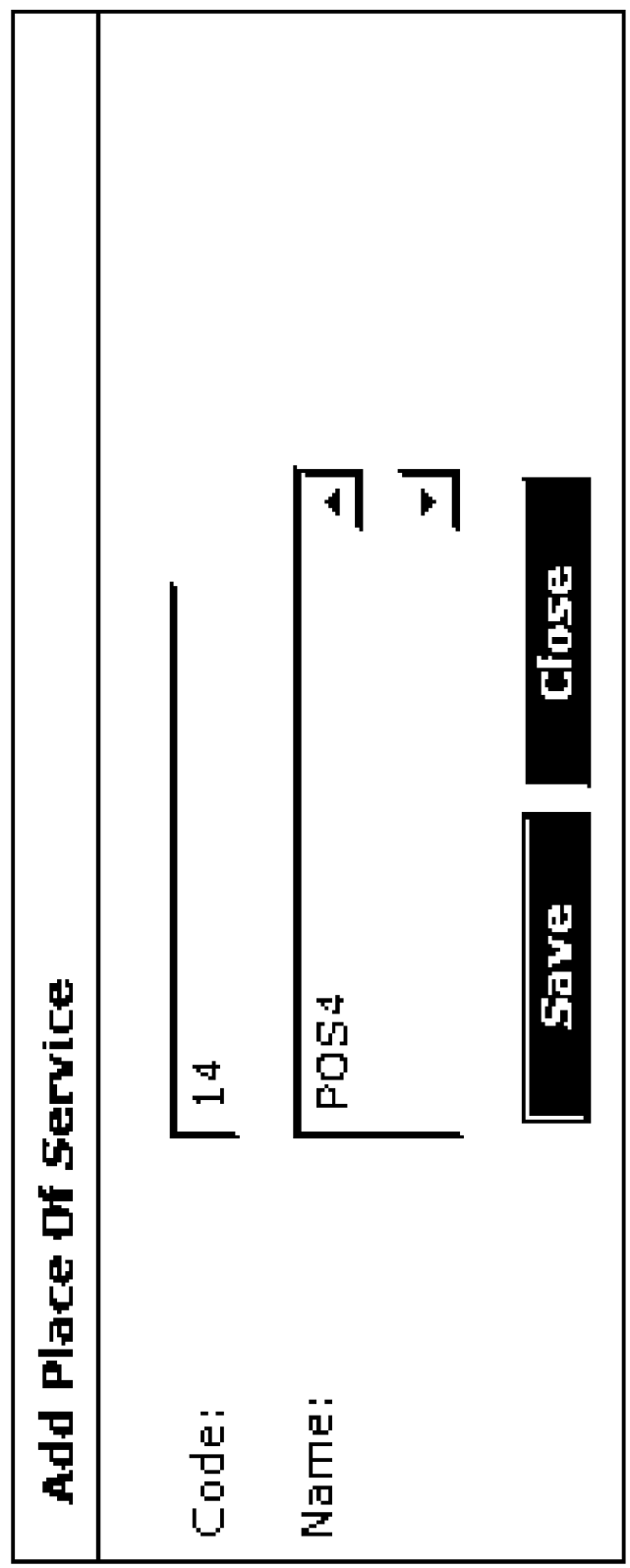
FIG. 62 shows an example of the Add Place of Service screen of the account settings of the Admin Doctor Application according to a preferred embodiment of the present invention.
Figure 64:
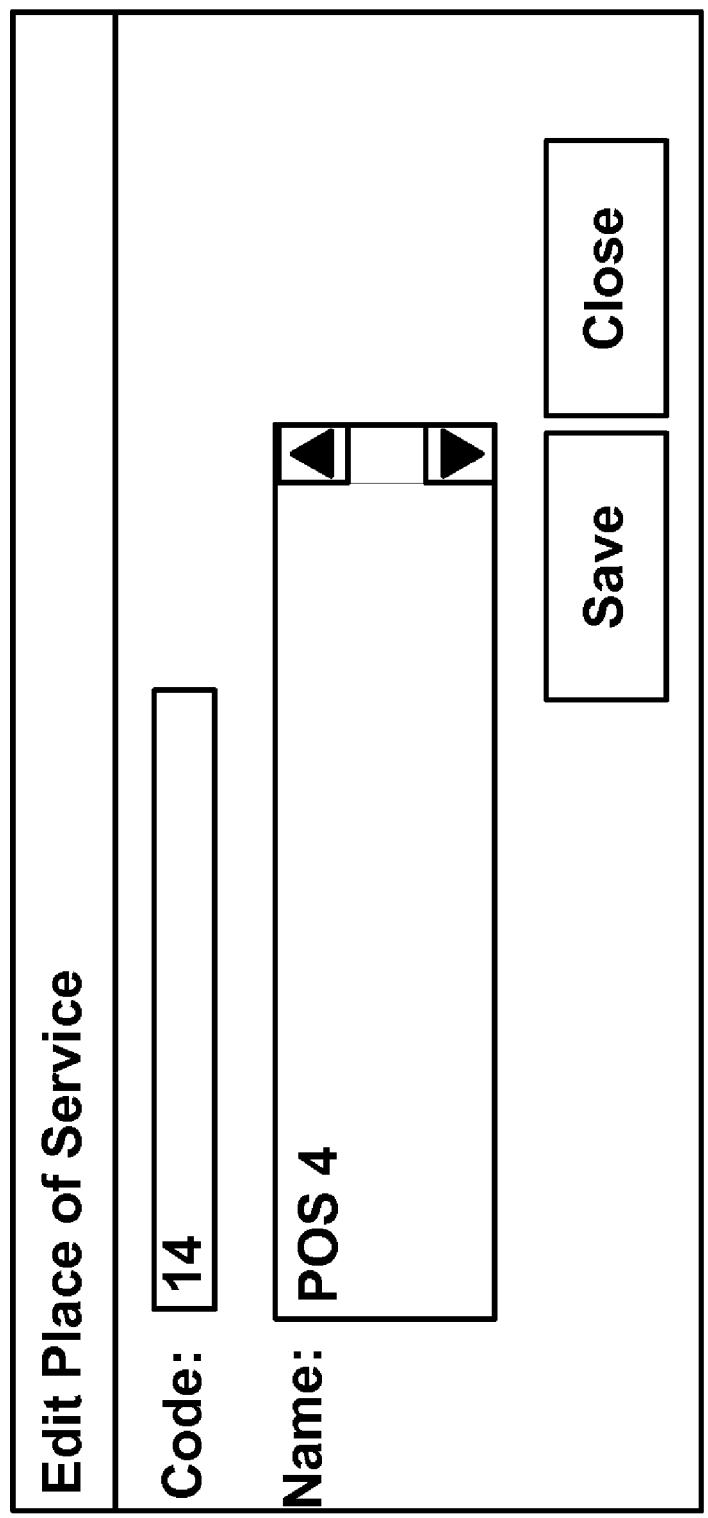
FIG. 64 shows an example of the Edit Place of Service of the account settings of the Admin Doctor Application according to a preferred embodiment of the present invention.

FIG. 50 shows an example of a New Entries Search screen of the Admin Doctor Application presented to a user according to a preferred embodiment of the present invention. FIG. 51 shows an example of the Patient New Entries Search Results screen of the Admin Doctor Application according to a preferred embodiment of the present invention. Within the New Entries Tab, all the new entries for Patient, Superbill, Appointment, CPT and Diagnosis added by doctors through use of the application will be listed for review when the "Review Patient new entries", "Review Superbill new entries", "Review Appointment new entries", "Review CPT new entries" and "Review Diagnosis new entries" are checked. Preferably, the new entries may be searched. The search option will show the search result based on the search criteria. New Entries may preferably be searched by the following search criteria: Created Date From, Created Date To, Provider. Preferably, to view all the new records, a user preferably clicks on the search button preferably without entering any search criteria. The New Entries screen provides an administrator with the capability to see what a practitioner performed while remotely accessing the system. The administrator may also edit entries made by the health care practitioner that are posted to a practice management system. This edit feature is available to correct data entry errors, improve billing efficiency, decrease claim denials, etc.

FIG. 52 shows an example of the Appointment New Entries Search Results screen of the Admin Doctor Application according to a preferred embodiment of the present invention.

FIG. 53 shows an example of the Superbill New Entries Search Results screen of the Admin Doctor Application according to a preferred embodiment of the present invention.

FIG. 54 shows an example of the CPT New Entries Search Results screen of the Admin Doctor Application according to a preferred embodiment of the present invention.

FIG. 55 shows an example of the Diagnosis New Entries Search Results screen of the Admin Doctor Application according to a preferred embodiment of the present invention.

FIG. 56 shows an example of the Rules Wizard screen of the Admin Doctor Application according to a preferred embodiment of the present invention.

Rules permits an administrator to ensure that users of the system are using the proper coding when entering new charges or new information into a patient's Superbill. For example, a rule may be created where when a specific CPT code is entered a particular POS (Place of Service, or where the doctor saw the patient) must be entered as well. For example, CPT Code 99213 may require POS 11. Within a rule, a CPT code value may be linked with a POS, Units, Diagnosis, Modifiers, as well as combinations of the above. The rules may be customized to a doctor's practice. The administrator may also give the doctor the option (through the Control Panel settings) to override the rule by entering data that does not comply with setup rules. The administrator can essentially control what sets of codes and data users are able to input which decrease incorrect codes input and improve billing efficiency. These features will lead to a decrease in the denial of claims.

FIG. 57 shows an example of the results of a CPT Code search of the Rules of the Admin Doctor Application according to a preferred embodiment of the present invention.

Figure 58:
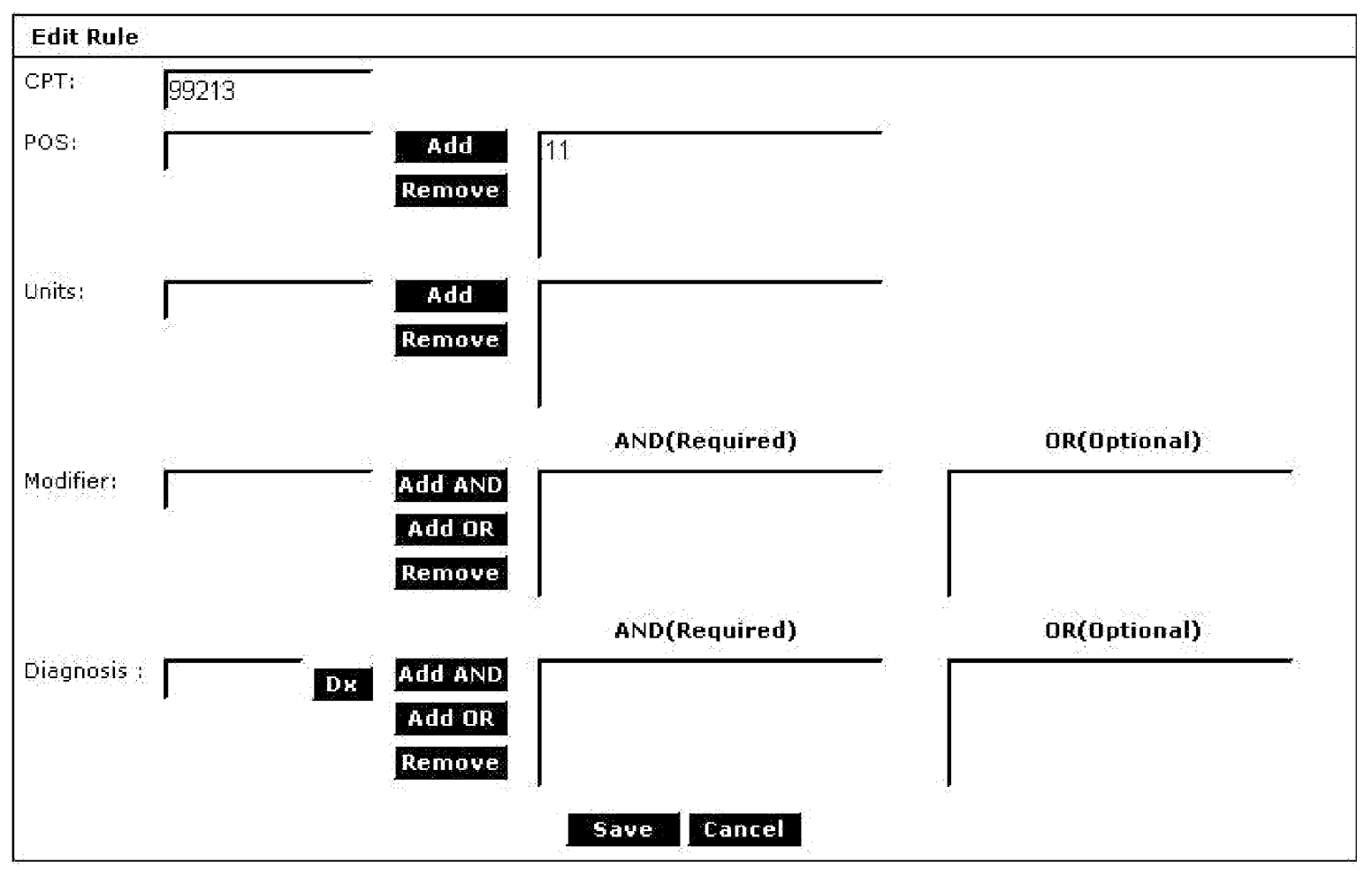

FIG. 58 shows an example of the Add Rule screen of the Admin Doctor Application according to a preferred embodiment of the present invention. POS typically refers to the place of service, or where the doctor saw and treated the patient. Units typically refer to a billing increment. For example, an anesthesiologist bills in minutes, so the units will be minutes. For other medical practices, the units may have different meaning. Modifier is a typical medical billing term. As stated, rules assist in reducing date entry errors.

To add a rule a user preferably takes the following actions:

Click on "SELECT CPT" button to select an existing CPT Code from the database or one may be entered manually.

Enter the values in the Place of Service ("POS") and Units text boxes and click on respective "Add" button to add values to the Rule. The input information may be removed by clicking on the "Remove" button to remove the values from the Rule.

Enter the values in the Modifiers and Diagnosis text boxes and click on the respective "Add AND" button to add values to the Rule. The values entered in the AND List box are required if the CPT rule is used to add a Superbill.

Enter the values in the Modifiers and Diagnosis text boxes and click on the respective "Add OR" button to add values to the Rule. The values entered in the OR List box are optional.

Diagnosis may be entered manually or by clicking on the "Dx" button where one may select the one or more Diagnosis Codes and click on the respective "Add AND" button to add values to the Rule. The values entered in the AND List box are required if the CPT rule is used to add a Superbill.

Diagnosis may be entered manually or by clicking on the "Dx" button where one can select the one or more Diagnosis Codes and click on the respective "Add OR" button to add values to the Rule. The values entered in the OR List box are optional.

Click on "Save" button to create the rule for the selected CPT Code.

The Added Rule will be applicable while Adding, Editing, Copying and Inserting a Superbill by using the respective CPT Code.

The following figures relate to the setup of the Doctor Admin Application.

FIG. 59, FIG. 60, FIG. 61, FIG. 62, FIG. 63, FIG. 64, and FIG. 65, show examples relating to the Place of Service features of the account settings of the Admin Doctor Application according to a preferred embodiment of the present invention. Preferably, searching, adding, editing and deleting a Place of Service may be done. With respect to searching a user preferably enters search criteria and clicks the Search button. The place of service according to the search criteria entered will be displayed in the search result area. By clicking on the reset button the entered search criteria is cleared. The Place of service can be searched on either of following criteria or a combination of the following criteria: Code and Name. Clicking on search button without entering any search criterion displays all the Place of Service in the database. With respect to adding a place of service, a user preferably clicks the "Add POS" button. The Add Place of Service page is displayed as shown. A user preferably clicks the "Save" button to add the desired POS. Preferably, a success message is displayed after the POS code is successfully added. With respect to editing a POS, clicking the edit button of any POS code will display the edit Place of Service popup window as shown. A user will preferably click the "Save" button to update the POS. Preferably, a success message is displayed after successful editing. With respect to deleting a POS, a user preferably clicks the delete icon button as shown.

Figure 66:
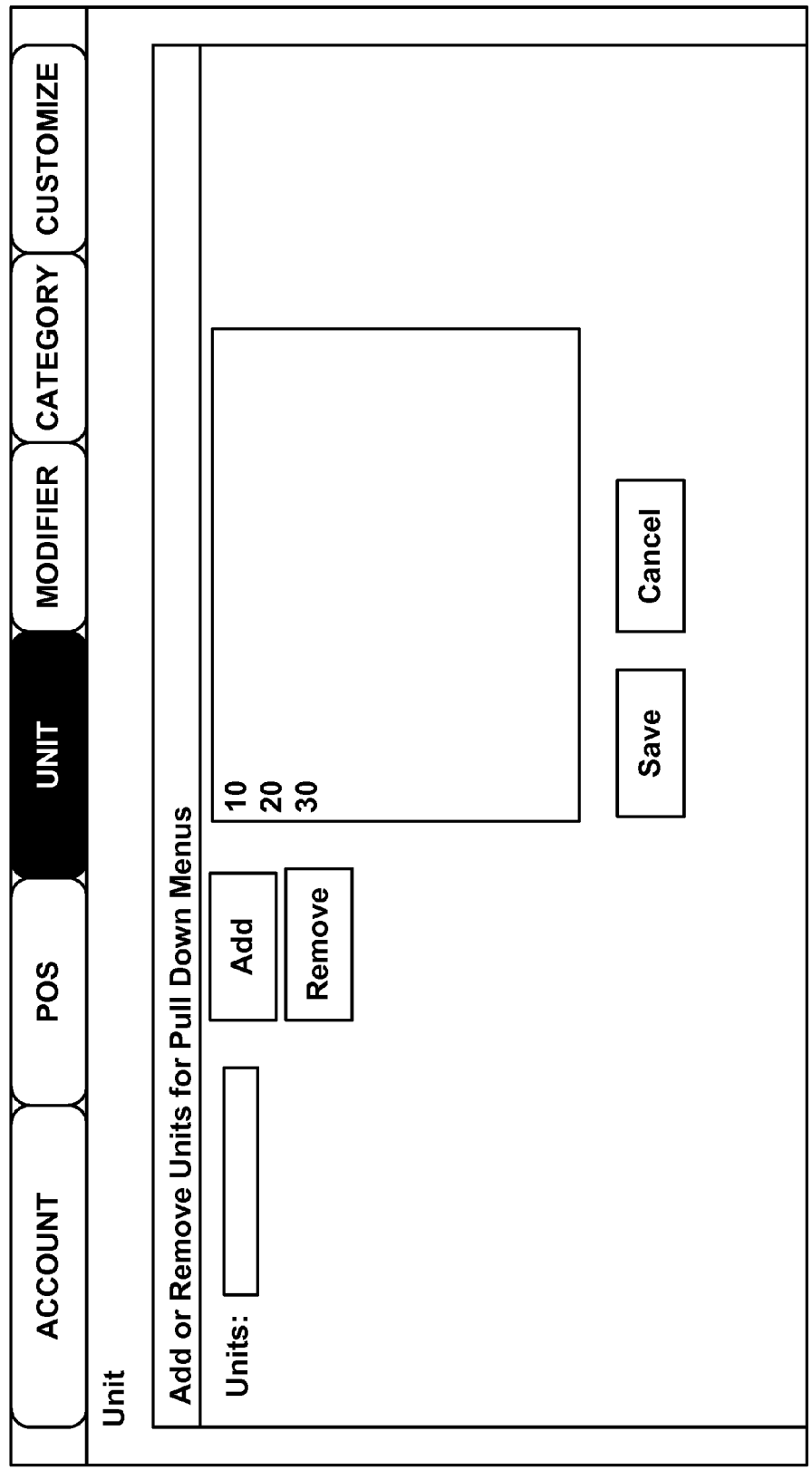
FIG. 66 shows an example of the Add-Units-to-pulldown-menus feature of the account settings of the Admin Doctor Application according to a preferred embodiment of the present invention.

FIG. 66 shows an example of the Add-Units-to-pulldown-menus feature of the account settings of the Admin Doctor Application according to a preferred embodiment of the present invention. Preferably, a user enters the values in the Units text boxes and click on "Add" button to add values to the list box. Preferably, a user may select single or multiple Units in the List box and click on "Remove" button to remove the selected values in the List Box. Preferably, a user clicks the "Save" button to save the values in the List Box and display the success message.

Figure 67:
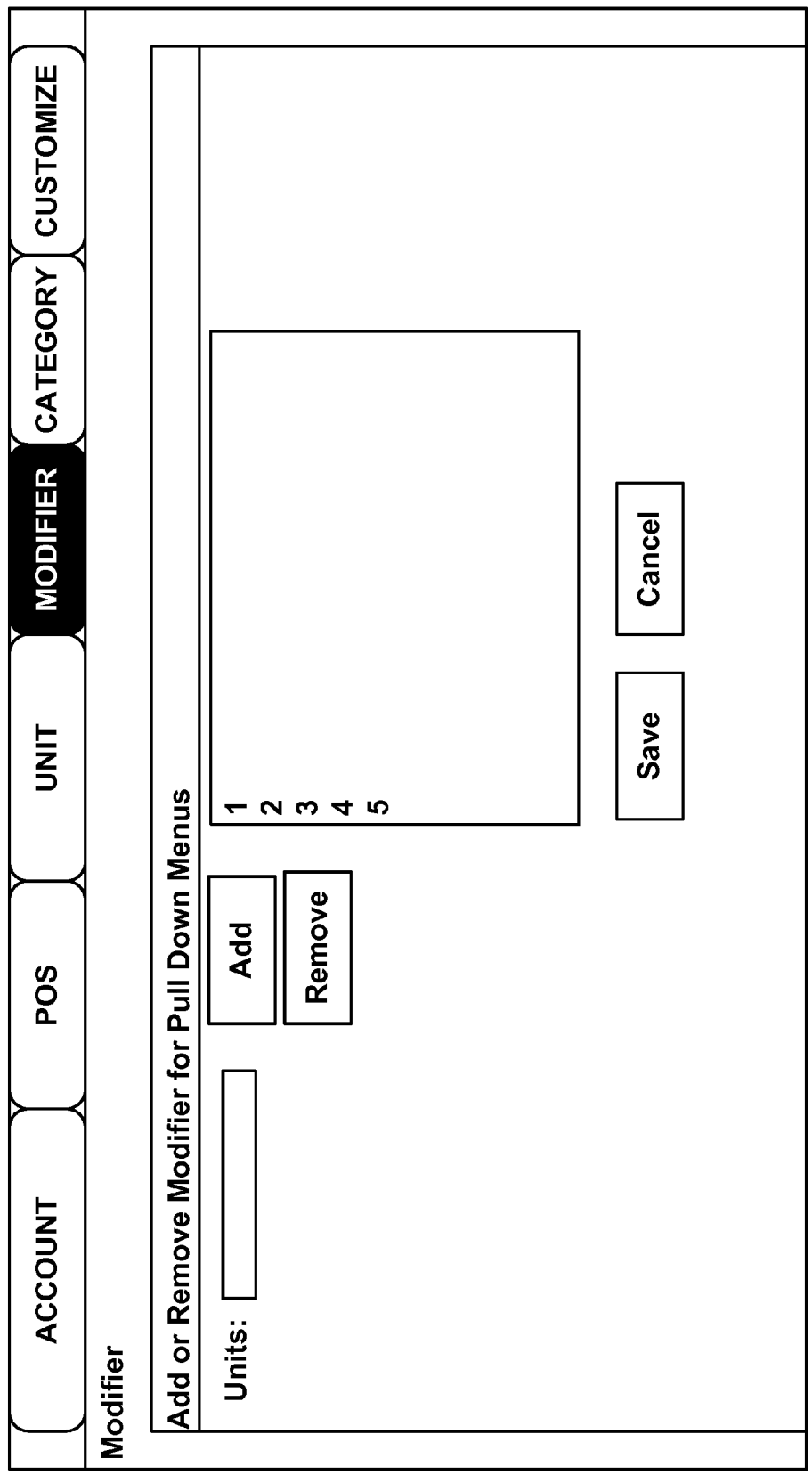
FIG. 67 shows an example of the Add or Remove Modifiers for Pull Down Menus screen of the account settings of the Admin Doctor Application according to a preferred embodiment of the present invention.

FIG. 67 shows an example of the Add or Remove Modifiers for Pull Down Menus screen of the account settings of the Admin Doctor Application according to a preferred embodiment of the present invention. Preferably, a user enters the values in the Modifier text boxes and clicks on the "Add" button to add values to the list box. Preferably, a user may select single or multiple Modifiers in the List box and clicks on "Remove" button to remove the selected values in the List Box. Preferably, a user clicks on the "Save" button to save the values in the List Box and display the success message.

FIG. 68 shows an example of the Search Patient Category feature of the account settings of the Admin Doctor Application according to a preferred embodiment of the present invention. To search Patient Categories, a user preferably enters search criteria and clicks on the Search button. The categories according to the search criteria entered will be displayed in the search result area. By clicking on reset button the entered search criteria is cleared. A category may be searched on either of following criteria or a combination of the following criteria: Category Name and Description. Clicking on search button without entering any search criteria displays all the categories in the database.

FIG. 69 shows an example of the results of a search performed with the Search Patient Category feature shown in FIG. 68.

FIG. 70 shows an example of the Add Patient Category feature of the account settings of the Admin Doctor Application according to a preferred embodiment of the present invention. To add a Category, a user preferably clicks on the "Add Category" button. The Add category page is displayed as shown. A user preferably clicks the "Save" button to add the category. Preferably, the newly added category is shown in the search result along with a success message.

Figure 71:
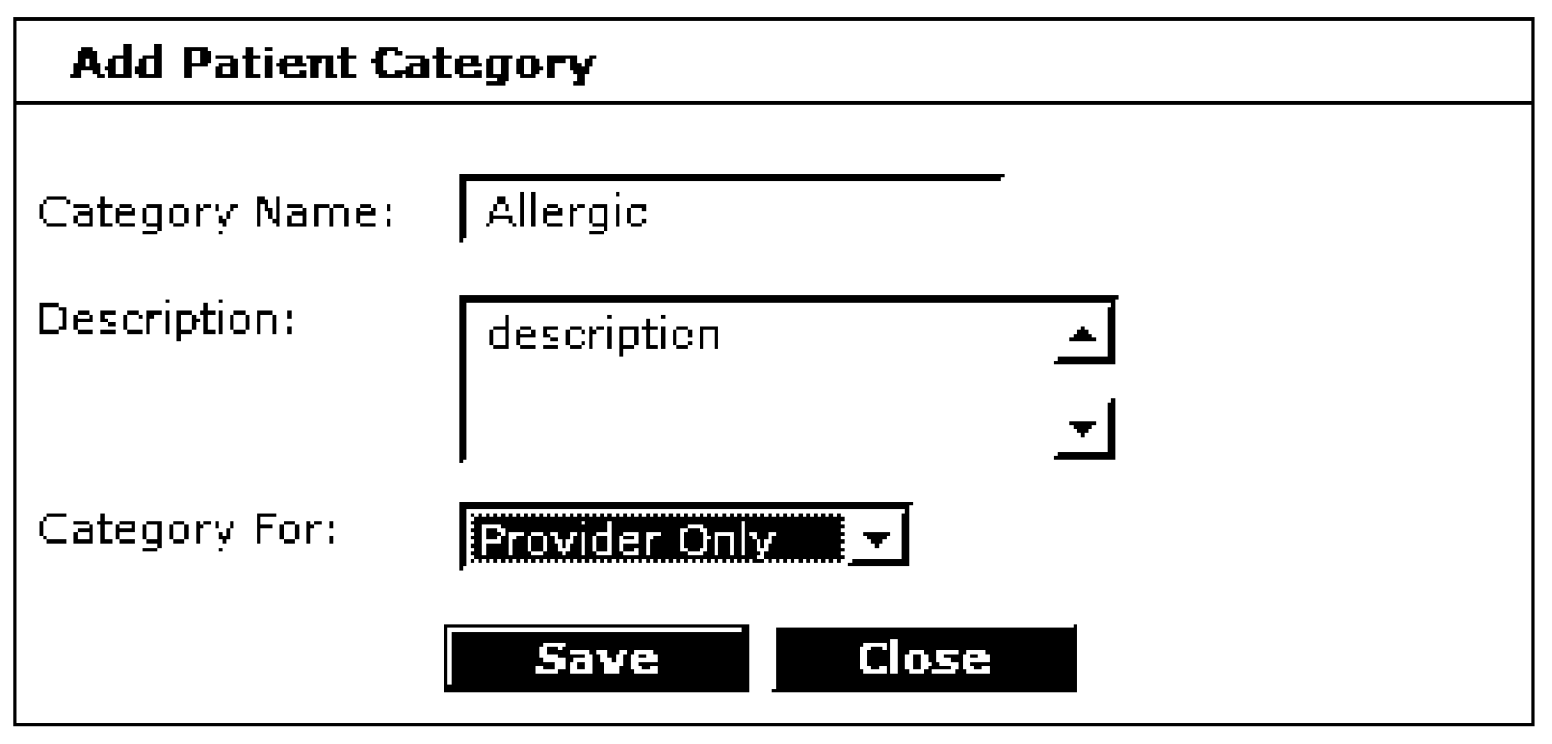

FIG. 71 shows an example of the Add Patient Category Screen of the Admin Doctor Application according to a preferred embodiment of the present invention.

FIG. 72 shows an example of the Edit Patient Category feature of the Admin Doctor Application according to a preferred embodiment of the present invention.

FIG. 73 shows an example of the Edit Patient Category Screen of the Admin Doctor Application according to a preferred embodiment of the present invention.

FIG. 74 shows an example of the Delete Patient Category feature of the Admin Doctor Application according to a preferred embodiment of the present invention.

FIG. 75 shows an example of a Customize View Superbill in Mobile screen of the Admin Doctor Application according to a preferred embodiment of the present invention. Preferably, the displayed content of a Superbill (Refer to FIG. 26 for the View Superbill screen) on the screen view of a mobile device screen may be customized as follows. Customizing the display content provides a user the ability to efficiently use the mobile device by decreasing scrolling, optimizing screen real estate, etc. A user selects the displayed content by moving the options from the left box to the right box using the appropriate transfer icon. Preferably, a CPT Code cannot be removed from the right list box. Based on the selection in the Left List box, a user preferably clicks on the right arrow button and the selected billing information will be displayed in the right List box. Preferably, four items of billing information may remain in the right List Box. Some of the selectable items preferably include the following: Location, Created Date, Copay, Facility, Insurance Company Name, Date From, Date To, Diagnosis Code 1, Diagnosis Code 2, and Billing Number (shown as "No"). Other selectable items may preferably include the following: CPT Code, Diagnosis Code 3, Diagnosis Code 4, Amount of CPT codes, Patient Portion of Bill, Insurance Portion of Bill, Billing balance, Account balance, Modifier 1, Modifier 2, Modifier 3, Modifier 4, Type of Service, and Billing Notes. A user preferably clicks the save button. On clicking the save button, the selected billing information will be displayed in the View Superbill page of the Mobile device. To increase the number of transaction lines, a numeric value (shown as five) may be modified. Increasing the number increases the number of transaction lines. Decreasing the number decreases the number of transaction lines.

Preferably 4 selected fields are displayed per line in the View Superbill Screen (FIG. 26). This feature allows doctors to choose what information they wish to see on their mobile device so that the doctors may bill efficiently.

Other features available in the Customize View Superbill in Mobile screen preferably include the following:
  Turn on CPT pull downs: If unchecked and the save button is clicked, a Doctor user will not be able to view the CPT Pull down in the Add/Edit/Add CPT Superbill page of both the web and mobile applications.
  Turn on Diagnosis pull downs: If unchecked and the save button is clicked, a Doctor user will not able to view the Diagnosis Pull down in the Add/Edit/Add CPT/Copy Superbill page of both the web and mobile applications.
  Turn on POS pull downs: If unchecked and the save button is clicked, a Doctor user will not be able to view the POS Pull down in the Add/Edit/Add CPT/Copy Superbill page of both the web and mobile applications.
  Turn on POS pull downs: If unchecked and the save button is clicked, a Doctor user will not be able to view the POS Pull down in the Add/Edit/Add CPT/Copy Superbill page of both the web and mobile applications.
  Turn on Units pull downs: If unchecked and the save button is clicked, a Doctor user will not be able to view the Units Pull down in the Add/Edit/Add CPT/Copy Superbill page of both the web and mobile applications.
  Turn on Modifier pull downs: If unchecked and the save button is clicked, a Doctor user will not be able to view the Modifiers Pull down in the Add/Edit/Add CPT/Copy Superbill page of both the web and mobile applications.
  Automatically add Diagnosis Codes from Patient to Superbill: If unchecked and the save button is clicked, a Doctor user will not be able to view the Diagnosis Codes assigned to Patient in the Add/Edit Superbill page of both the web and mobile applications.

Figure 76:
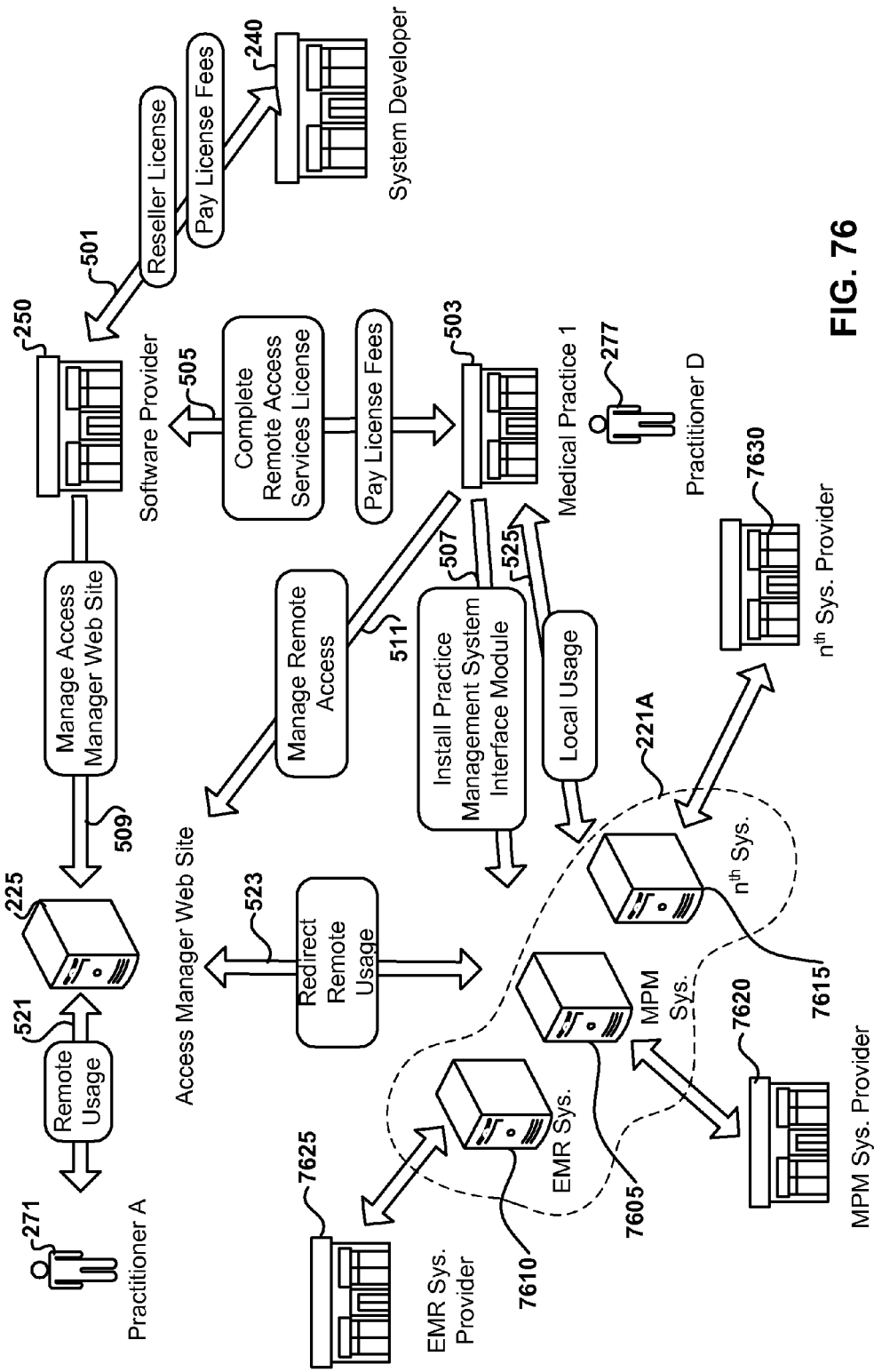
FIG. 76 shows an example of a schematic illustration of a preferred business method relating to licensing, implementation, and use of the Remote Access Management System used with more than one software system according to a preferred embodiment of the present invention.

FIG. 76 shows an example of a schematic illustration of a preferred business method relating to licensing, implementation, and use of the Remote Access Management System used with more than one medical practice support system according to a preferred embodiment of the present invention. The preferred processes and methods of FIG. 76 are substantially similar to those in FIG. 4 except for the following exceptions. Alternately, preferably Practice 1 Data Center 221A comprises at least one medical practice management system 7605 (MPM Sys.) and at least one electronic medical records system 7610 (EMR Sys.). Practice 1 Data Center 221A may also preferably comprise at least one related $n^{th}$ system 7615 ($n^{th}$ Sys.), as shown. Several choices for medical practice management system 7605, electronic medical records system 7610, and $n^{th}$ system 7615 may exist. Preferably, medical practice management system 7610 is provided by at least one medical practice management software provider 7620, as shown. Preferably, electronic medical records system 7605 is provided by at least one electronic medical records system provider 7625 (EMR Sys. Provider), as shown. Preferably, electronic medical records system 7610, medical practice management system 7605, and $n^{th}$ system 7615 are not otherwise web-enabled. System Developer 240 preferably web-enables such systems as disclosed herein. The electronic medical records system may include laboratory connectivity features (to view laboratory results of a patient), electronic prescription writing, as well as the ability to write to a patient's medical records. Preferably, as shown, a practitioner (Practitioner A) will access the features of the electronic medical records system (laboratory connectivity, electronic prescription writing, write to a patient's medical records).

Preferably, $n^{th}$ system 7615 ($n^{th}$ Sys.) is provided by at least one $n^{th}$ system provider 7630 ($n^{th}$ Sys. Provider), as shown. Preferably, the Remote Access Management System provided to Medical Practice 1 provides, quickly and easily, a practitioner with secure, remote access to the medical support system operated by Medical Practice 1 (such arrangement at least embodying herein wherein such at least one medical practice support system comprises at least one electronic medical record management system). Preferably, system developer develops a remote access management system that integrates at least a medical practice management system and an electronic medical records system so that a practitioner may access a single remote access management system (by way of Access Manager Website) to complete a variety of real-time interactions with the Medical Practice Support Management System operated on behalf of Medical Practice 1 503, as shown by Remote Usage Process 521. Preferably, all remote interactions by Practitioner A 271 with the Practice Management System are redirected from Access Manager Web Site 225 to Practice 1 Data Center 221 as depicted by Redirect Remote Usage Process 523. Preferably, all remote interactions are accepted and managed by Medical Practice Support System Interface Module 453 which receives the request, prepares and sends the appropriate request to the appropriate system (medical practice management system 7605, electronic medical records system 7610, or $n^{th}$ system 7615 Practice Management System), receives the appropriate response and then formats the output for the type of remote device (laptop, cell phone or PDA, etc.) used by Practitioner A 271 and sends it back to the remote device being used by Practitioner A 271. Further, a request may be sent to multiple systems, for example, a single request may be sent simultaneously to medical practice management system 7605 and electronic medical records system 7610). The result is a seamless integration of practitioner activities to multiple medical practice support systems using a single system developed by a software developer.

Although applicant has described applicant's preferred embodiments of this invention, it will be understood that the broadest scope of this invention includes modifications. Such scope is limited only by the below claims as read in connection with the above specification. Further, many other advantages of applicant's invention will be apparent to those skilled in the art from the above descriptions and the below claims.

What is claimed is:

1. A method comprising the steps of:
a) offering, by at least one computer software provider, relating to at least one medical practice support computer system having at least one computer processor, at least one web-browser-based communications computer software system to at least one user of at least one wireless-access-protocol-enabled cellular-based device;
b) wherein said at least one web-browser-based communications computer software system enables real-time computer communications between such at least one wireless-access-protocol-enabled cellular-based device and such at least one medical practice support computer system;
c) communicatively coupling such at least one web-browser-based communications computer software system to such at least one medical practice support computer system;
d) permitting access to such at least one web-browser-based communications computer software system by such at least one user;
e) wherein such at least one web-browser-based communications computer software system receives at least one function request from such at least one wireless-access-protocol-enabled cellular-based device to be processed by such at least one medical practice support computer system;
f) wherein such at least one web-browser-based communications software system transmits such at least one function request to such at least one medical practice support computer system;
g) wherein such at least one medical practice support computer system generates at least one result and such at least one result is received by such at least one web-browser-based communications computer software system;
h) wherein such generated result of such at least one function request is transmitted to such at least one wireless-access-protocol-enabled cellular-based device;
i)
j)
k)
l) wherein such at least one web-browser-based communications software system assists display of such generated results of such at least one function request on such at least one wireless-access-protocol-enabled cellular-based device;
m) wherein such at least one function request from such at least one wireless-access-protocol-enabled cellular-based device received by such at least one web-browser-based communications computer software system for computer processing by such at least one medical practice support computer system comprises
i) at least one search request relating to patient information data wherein such requested at least one search relating to patient information data is processed by such at least one medical practice support computer system; and ii) at least one view request relating to such patient information data wherein such requested at least one view of such patient information data is processed by such at least one medical practice support computer system;

iii) at least one modification request relating to such patient information data wherein such requested at least one modification relating to such patient information data is processed by such at least one medical practice support computer system;

iv) at least one add request relating to such patient information data wherein such at least one medical practice support computer system processes such at least one add request relating to such patient information data; and v)

vi)

vii) at least one view request relating to patient appointment data wherein such requested at least one view relating to such patient appointment data is processed by such at least one medical practice support computer system;

viii) at least one modification request relating to such patient appointment data wherein such requested at least one modification relating to such patient appointment data is processed by such at least one medical practice support computer system;

ix) at least one add request relating to such patient appointment data wherein such at least one medical practice support computer system processes such at least one add request relating to such patient appointment data;

x)

xi)

xii) at least one view request relating to patient-related diagnostic and procedure code data wherein such requested at least one view relating to patient-related diagnostic and procedure code data is processed by such at least one medical practice support computer system;

xiii) at least one modification request relating to such patient-related diagnostic and procedure code data wherein such requested at least one modification relating to patient-related diagnostic and procedure code data is processed by such at least one medical practice support computer system;

xiv) at least one add request relating to such patient-related diagnostic and procedure code data wherein such at least one medical practice support computer system processes such at least one add request relating to such patient-related diagnostic and procedure code data; and xv)

xvi) at least one search request relating to procedure code data wherein such requested at least one search relating to procedure code data is processed by such at least one medical practice support computer system; and xvii) at least one view request relating to such procedure code data wherein such requested at least one view relating to such procedure code data is processed by such at least one medical practice support computer system;

xviii) at least one modification request relating to such procedure code data wherein such requested at least one modification relating to such procedure code data is processed by such at least one medical practice support computer system;

xix) at least one add request relating to such procedure code data wherein such at least one medical practice support computer system processes such at least one add request relating to such procedure code data; and xx)

xxi) at least one search request relating to diagnostic code data wherein such requested at least one search relating to diagnostic code data is processed by such at least one medical practice support computer system; and xxii) at least one view request relating to such diagnostic code data wherein such requested at least one view relating to such diagnostic code data is processed by such at least one medical practice support computer system;

xxiii) at least one modification request relating to such diagnostic code data wherein such requested at least one modification relating to such diagnostic code data is processed by such at least one medical practice support computer system;

xxiv) at least one add request relating to such diagnostic code data wherein such at least one medical practice support computer system processes such requested at least one add request relating to such diagnostic code data; and xxv).

2. The method according to claim 1, wherein said at least one medical practice support computer system comprises at least one electronic medical record management computer system having at least one computer processor.

* * * * *